(12) United States Patent
Arav-Boger et al.

(10) Patent No.: US 8,883,765 B2
(45) Date of Patent: Nov. 11, 2014

(54) ANTI-CYTOMEGALOVIRUS ACTIVITY OF ARTEMISININ-DERIVED DIMERS

(75) Inventors: Ravit Arav-Boger, Baltimore, MD (US); Gary Posner, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 27 days.

(21) Appl. No.: 13/514,645

(22) PCT Filed: Dec. 8, 2010

(86) PCT No.: PCT/US2010/059390
§ 371 (c)(1),
(2), (4) Date: Jan. 15, 2013

(87) PCT Pub. No.: WO2011/071981
PCT Pub. Date: Jun. 16, 2011

(65) Prior Publication Data
US 2013/0109654 A1    May 2, 2013

Related U.S. Application Data

(60) Provisional application No. 61/267,555, filed on Dec. 8, 2009, provisional application No. 61/356,869, filed on Jun. 21, 2010.

(51) Int. Cl.
*A61K 31/357* (2006.01)
*C07D 493/18* (2006.01)
*C07F 9/6561* (2006.01)
*A61K 31/683* (2006.01)
*A61K 45/06* (2006.01)

(52) U.S. Cl.
CPC ............. *A61K 31/357* (2013.01); *A61K 31/683* (2013.01); *A61K 45/06* (2013.01); *C07D 493/18* (2013.01); *C07F 9/6561* (2013.01)
USPC ............. 514/86; 435/375; 514/450; 514/100; 514/263.31; 514/120

(58) Field of Classification Search
None
See application file for complete search history.

(56) References Cited

U.S. PATENT DOCUMENTS

2006/0142377 A1* 6/2006 Posner et al. ............. 514/452
2007/0142459 A1* 6/2007 Schlegel et al. ............. 514/452
2009/0082426 A1* 3/2009 Commercon et al. ......... 514/450

OTHER PUBLICATIONS

Griffiths, P., et al., "Betaherpesviruses in transplant recipients" J Antimicrob Chemother. 2000;45(Suppl T3):29-34.
Matthews, T., et al., "Antiviral activity and mechanism of action of ganciclovir" Rev Infect Dis. 1988;10(Suppl 3): S490-S494.
Chrisp, P., et al., "Foscarnet. A review of its antiviral activity, pharmacokinetic properties and therapeutic use in immunocompromised patients with cytomegalovirus retinitis" Drugs. 1991;41:104-129.
Neyts, J., et al., "Selective inhibition of human cytomegalovirus DNA synthesis by (S)-1-(3-hydroxy-2-phosphonylmethoxypropyl)cytosine [(S)-HPMPC] and 9-(1,3-dihydroxy-2-propoxymethyl)guanine (DHPG)" Virology. 1990;179:41-50.
Schreiber, A., et al., "Antiviral treatment of cytomegalovirus infection and resistant strains" Expert Opin Pharmacother. 2009;10:191-209.
Biron, K., et al., "Antiviral drugs for cytomegalovirus diseases" Antiviral Res. 2006;71:154-163.
Chou S., "Antiviral drug resistance in human cytomegalovirus" Transpl Infect Dis. 1999;1:105-114.
Adjuik, M., et al., "Artesunate combinations for treatment of malaria: meta-analysis" Lancet. 2004;363:9-17.
Efferth, T., et al., "The anti-malarial artesunate is also active against cancer" Int J Oncol. 2001;18:767-773.
Kaptein, S., et al., "The anti-malaria drug artesunate inhibits replication of cytomegalovirus in vitro and in vivo" Antiviral Res. 2006;69:60-69.
Efferth, T., et al., "Antiviral activity of artesunate towards wild-type, recombinant, and ganciclovir-resistant human cytomegaloviruses" J Mol Med. 2002;80:233-242.
Posner, G., et al., "Orally active, antimalarial, anticancer, artemisinin-derived trioxane dimers with high stability and efficacy" J Med Chem. 2003;46:1060-1065.
Alagbala, A., et al., "Biological mechanisms of action of novel C-10 non-acetal trioxane dimers in prostate cancer cell lines" J Med Chem. 2006;49:7836-7842.
Ahn, J., et al., "Disruption of PML-associated nuclear bodies by IE1 correlates with efficient early stages of viral gene expression and DNA replication in human cytomegalovirus infection" Virology. 2000;274:39-55.
Woodard, L., et al., "Malaria-Infected Mice Live until at Least Day 30 after a New Monomeric Trioxane Combined with Mefloquine Are Administered Together in a Single Low Oral Dose" J Med Chem. 2009;52:7458-7462.
Rosenthal, A., et al., "Malaria-infected mice are cured by a single oral dose of new dimeric trioxane sulfones which are also selectively and powerfully cytotoxic to cancer cells" J Med Chem. 2009;52:1198-1203.
Tanaka, Y., et al., "Monitoring cytomegalovirus infection by antigenemia assay and two distinct plasma real-time PCR methods after hematopoietic stem cell transplantation" Bone Marrow Transplant. 2002;30:315-319.

(Continued)

*Primary Examiner* — Dennis Heyer
(74) *Attorney, Agent, or Firm* — John Hopkins Technology Transfer

(57) ABSTRACT

Artemisinin-derived monomers and artemisinin dimers are shown to exhibit in-vitro anti-cytomegalovirus (CMV) activity. Artemisinin dimers effectively inhibited CMV replication in human foreskin fibroblasts and human embryonic lung fibroblasts with no cytotoxicity at concentrations required for complete CMV inhibition. Artemisinin dimers were found to be potent and non-cytotoxic inhibitors of CMV replication, which indicates their use as therapeutic agents for the treatment of CMV infection in humans.

48 Claims, 9 Drawing Sheets

(56) References Cited

OTHER PUBLICATIONS

Jones-Brando, L., et al., "In vitro inhibition of *Toxoplasma gondii* by four new derivatives of artemisinin" Antimicrob Agents Chemother. 2006;50:4206-4208.

Stinski, M., "Sequence of protein synthesis in cells infected by human cytomegalovirus: early and late virus-induced polypeptides" J Virol. 1978;26:686-701.

Sia, I., et al., "New strategies for prevention and therapy of cytomegalovirus infection and disease in solid-organ transplant recipients" Clin Microbiol Rev. 2000;13:83-121.

Yust, I., et al., "Retinal and extraocular cytomegalovirus end-organ disease in HIV-infected patients in Europe: a EuroSIDA study" 1994-2001. Eur J Clin Microbiol Infect Dis. 2004;23:550-559.

Krosky, P., et al., "The human cytomegalovirus UL97 protein kinase, an antiviral drug target, is required at the stage of nuclear egress" J Virol. 2003;77:905-914.

Williams, S., et al., "In vitro activities of benzimidazole D- and L-ribonucleosides against herpesviruses" Antimicrob Agents Chemother. 2003;47:2186-2192.

Winston, D., et al., "Maribavir prophylaxis for prevention of cytomegalovirus infection in allogeneic stem cell transplant recipients: a multicenter, randomized, double-blind, placebo-controlled, dose-ranging study" Blood. 2008;111:5403-5410.

Schang, L., et al., "Five years of progress on cyclin-dependent kinases and other cellular proteins as potential targets for antiviral drugs" Antivir Chem Chemother. 2006;17:293-320.

Chou, S., et al., "Effect of cell culture conditions on the anticytomegalovirus activity of maribavir" Antimicrob Agents Chemother. 2006;50:2557-2559.

Posner, G., et al., "Antimalarial, antiproliferative, and antitumor activities of artemisinin-derived, chemically robust, trioxane dimers" J Med Chem. 1999;42:4275-4280.

Firestone, G., et al., "Anticancer activities of artemisinin and its bioactive derivatives" Expert Rev Mol Med. 2009;11:e32.

Efferth, T., et al., "The antiviral activities of artemisinin and artesunate" Clin Infect Dis. 2008;47:804-811.

Shapira, M., et al., "Artesunate as a potent antiviral agent in a patient with late drug-resistant cytomegalovirus infection after hematopoietic stem cell transplantation" Clin Infect Dis. 2008;46:1455-1457.

\* cited by examiner

ANTI-CYTOMEGALOVIRUS ACTIVITY OF ARTEMISININ-DERIVED DIMERS

CROSS-REFERENCE TO RELATED APPLICATIONS

This application is a 35 U.S.C. §371 U.S. National Stage entry of International Application PCT/US2010/059390, having an international filing date of Dec. 8, 2010, which claims the benefit of U.S. Provisional Application Nos. 61/267,555, filed Dec. 8, 2009, and 61/356,869, filed Jun. 21, 2010, each of which is incorporated herein by reference in its entirety.

FEDERALLY SPONSORED RESEARCH OR DEVELOPMENT

This invention was made in part with United States Government support under AI 34885 awarded by the National Institutes of Health (NIH). The U.S. Government has certain rights in the invention.

BACKGROUND

Infection with cytomegalovirus (CMV) is common in humans and is usually asymptomatic. Weller T H. The cytomegaloviruses: ubiquitous agents with protean clinical manifestations. II. *N Engl J Med.* 1971; 285:267-274; Weller T H. The cytomegaloviruses: ubiquitous agents with protean clinical manifestations. I. *N Engl J Med.* 1971; 285:203-214. In immunocompromised hosts, such as transplant recipients and patients with AIDS, CMV infection is associated with significant morbidity and mortality. Griffiths P D, Clark D A, Emery V C. Betaherpesviruses in transplant recipients. *J Antimicrob Chemother.* 2000; 45(Suppl T3):29-34; Kovacs A, Schluchter M, Easley K, Demmler G, Shearer W, et al. Cytomegalovirus infection and HIV-1 disease progression in infants born to HIV-1-infected women. Pediatric Pulmonary and Cardiovascular Complications of Vertically Transmitted HIV Infection Study Group. *N Engl J Med.* 1999; 341:77-84. Cytomegalovirus infection also is the most common congenitally-acquired infection and the leading infectious agent causing mental retardation and deafness in congenitally infected children. Demmler G J. Infectious Diseases Society of America and Centers for Disease Control. Summary of a workshop on surveillance for congenital cytomegalovirus disease. *Rev Infect Dis.* 1991; 13:315-329.

In recent years, CMV has been associated with a variety of syndromes including hypertension, severe pulmonary complications in patients in intensive care-units, and with a specific brain tumor, glioblastoma multiforme. Osawa R, Singh N. Cytomegalovirus infection in critically ill patients: a systematic review. *Crit Care.* 2009; 13:R68; Limaye A P, Kirby K A, Rubenfeld G D, Leisenring W M, Bulger E M, et al. Cytomegalovirus reactivation in critically ill immunocompetent patients. *JAMA.* 2008; 300:413-422; Cheng J, Ke Q, Jin Z, Wang H, Kocher O, et al. Cytomegalovirus infection causes an increase of arterial blood pressure. *PLoS Pathog.* 2009; 5: e1000427; Mitchell D A, Xie W, Schmittling R, Learn C, Friedman A, et al. Sensitive detection of human cytomegalovirus in tumors and peripheral blood of patients diagnosed with glioblastoma. *Neuro Oncol.* 2008; 10:10-18. Although the exact role of CMV in these syndromes is unclear, CMV replication appears to affect the natural history and outcome of disease processes in immunocompetent individuals, as well.

Despite significant ongoing research effort, no CMV vaccine is approved for universal or targeted use. Available anti-CMV drugs, e.g., ganciclovir (GCV), cidofovir and foscarnet, effectively inhibit virus replication by targeting the viral DNA polymerase. Matthews T, Boehme R. Antiviral activity and mechanism of action of ganciclovir. *Rev Infect Dis.* 1988; 10(Suppl 3):S490-S494; Chrisp P, Clissold S P. Foscarnet. A review of its antiviral activity, pharmacokinetic properties and therapeutic use in immunocompromised patients with cytomegalovirus retinitis. *Drugs.* 1991; 41:104-129; Neyts J, Snoeck R, Schols D, Balzarini J, De C E. Selective inhibition of human cytomegalovirus DNA synthesis by (S)-1-(3-hydroxy-2-phosphonylmethoxypropyl)cytosine [(S)-HPMPC] and 9-(1,3-dihydroxy-2-propoxymethyl)guanine (DHPG). *Virology.* 1990; 179:41-50.

Use of these drugs, however, is associated with considerable side effects, such as bone marrow toxicity (GCV) and nephrotoxicity (foscarnet and cidofovir). Schreiber A, Harter G, Schubert A, Bunjes D, Mertens T, et al. Antiviral treatment of cytomegalovirus infection and resistant strains. *Expert Opin Pharmacother.* 2009; 10:191-209; Biron K K. Antiviral drugs for cytomegalovirus diseases. *Antiviral Res.* 2006; 71:154-163. Oral valganciclovir has good bioavailability and is used in bone marrow and organ transplant recipients for CMV prophylaxis and treatment. Valganciclovir has not been approved yet for the treatment of infants with congenital CMV infection; a phase III clinical trial comparing six weeks to six months of valganciclovir therapy is actively enrolling infants. Preliminary data from this trial reveal that GCV-resistant variants emerge during therapy. Drug resistance also develops during prolonged or repeated treatment in the transplant population. Chou S. Antiviral drug resistance in human cytomegalovirus. *Transpl Infect Dis.* 1999; 1:105-114. Accordingly, because of the problems associated with currently available anti-CMV compounds, very limited treatment options for congenital CMV infection exist.

SUMMARY

In one aspect, the presently disclosed subject matter provides a method for treating a cytomegalovirus (CMV) infection in a subject in need of treatment thereof, the method comprising administering to the subject a therapeutically-effective amount of a compound selected from the group consisting of:

(a)

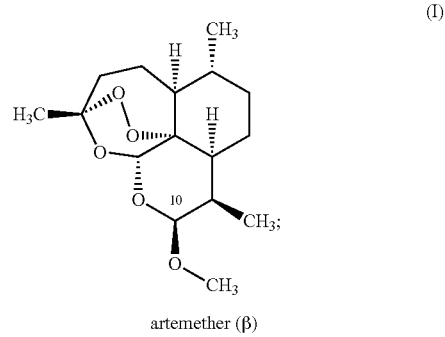

artemether (β)

(b)

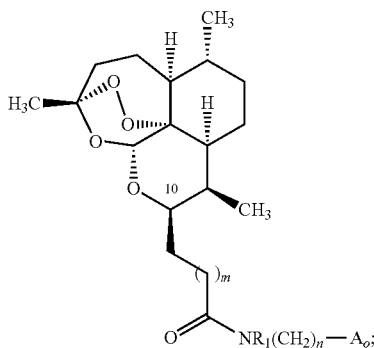

(II)

wherein:
m is an integer from 0 to 3;
n is an integer from 0 to 4;
p is an integer from 1 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
$A_O$ is selected from the group consisting of a halogen-substituted phenyl; substituted or unsubstituted heteroaryl; and —Si$(R_2)_3$, wherein each $R_2$ is independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

(c)

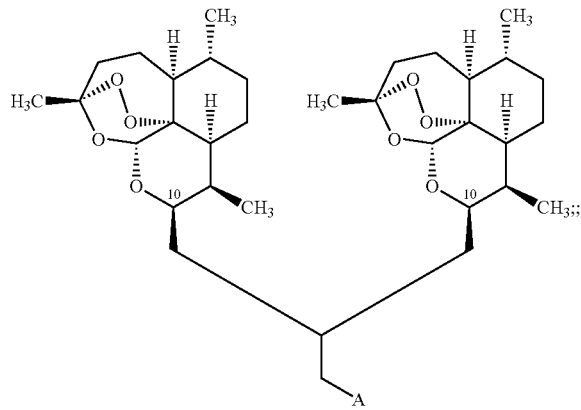

(III)

wherein:
A is —OH or S(O)$_n$—$R_1$,
n is independently an integer from 0 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein $R_1$ is optionally substituted with 1 to 5 $R_2$ groups;

each $R_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$OR$_3$, —(CH$_2$)$_q$O(CH$_2$)$_t$O—(CH$_2$)$_u$O(CH$_2$)$_j$OR$_3$, —(CH$_2$)$_j$C(O)R$_3$, —(CH$_2$)$_j$OC(O)OR$_3$, —(CH$_2$)$_j$OC(O)R$_3$, —(CH$_2$)$_j$NR$_4$R$_5$, —(CH$_2$)$_j$C(O)NR$_4$R$_5$, —(CH$_2$)$_j$OC(O)NR$_4$R$_5$, —(CH$_2$)$_j$NR$_6$C(O)R$_3$, —(CH$_2$)$_j$NR$_6$C(O)OR$_3$, —(CH$_2$)$_j$NR$_6$C(O)NR$_4$R$_5$, —(CH$_2$)$_j$S(O)$_m$R$_7$, —(CH$_2$)$_j$S(O)$_2$NR$_4$R$_5$, —(CH$_2$)$_j$NR$_6$S(O)$_2$R$_7$, or —(CH$_2$)$_j$OP(O)(OR$_7$)$_2$, wherein q is independently an integer from 0 to 20, and j, t, and u are each independently an integer from 0 to 6, and each m is independently an integer from 0 to 2, wherein $R_2$ is optionally independently substituted with 1 to 5 $R_8$ groups;

$R_3$, $R_4$, $R_5$, $R_6$, and $R_7$ are each independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or $R_3$, $R_6$, and $R_7$ are as described above, and $R_4$ and $R_5$, together with the N atom to which they are attached, form substituted or unsubstituted heterocycloalkyl, or substituted or unsubstituted heteroaryl, wherein $R_3$, $R_4$, $R_5$, $R_6$, and $R_7$ are each optionally independently substituted with 1 to 5 $R_8$ groups: and $R_8$ is independently selected from the group consisting of halogen, hydroxyl, cyano, nitro, alkyl, perfluoroalkyl, oxo, NH$_2$, NH(alkyl), N(alkyl)$_2$, O-alkyl, S-alkyl, aryl, arylalkyl, heteroaryl, and heteroarylalkyl;

(d)

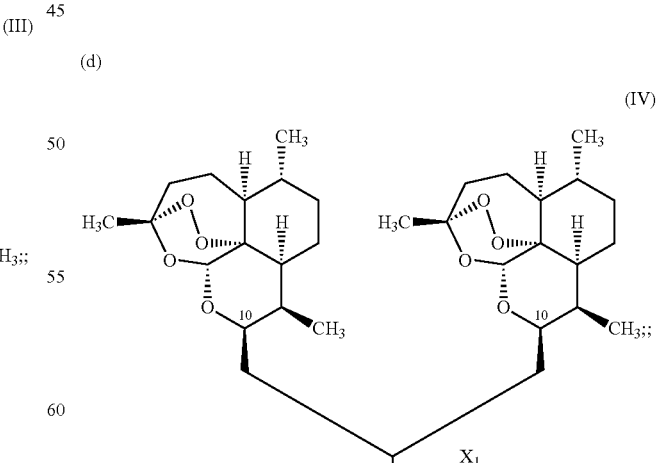

(IV)

wherein:

L is a linking group selected from (=N)— or —(CH$_2$)$_m$—, wherein m is an integer from 0 to 3;

X$_1$ is O or S;

A$_1$ and A$_2$ can be the same or different and are each independently selected from the group consisting of hydrogen, substituted or unsubstituted cycloalkyl, substituted or unsubstituted aryl, and substituted or unsubstituted heteroaryl, or A$_1$ and A$_2$ together form a substituted or unsubstituted biphenyl moiety; and (e)

(V)

wherein:

q is an integer from 0 to 5;

each occurrence of R$_{3d}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl; or an enantiomer, diastereomer, racemate or pharmaceutically acceptable salt, prodrug, or solvate thereof.

In further aspects, the presently disclosed subject matter provides a method for inhibiting cytomegalovirus (CMV) replication in a cell, the method comprising contacting the cell with a compound of Formula (I-V).

In yet further aspects, the presently disclosed subject matter provides a compound of Formula (IV) or Formula (V).

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
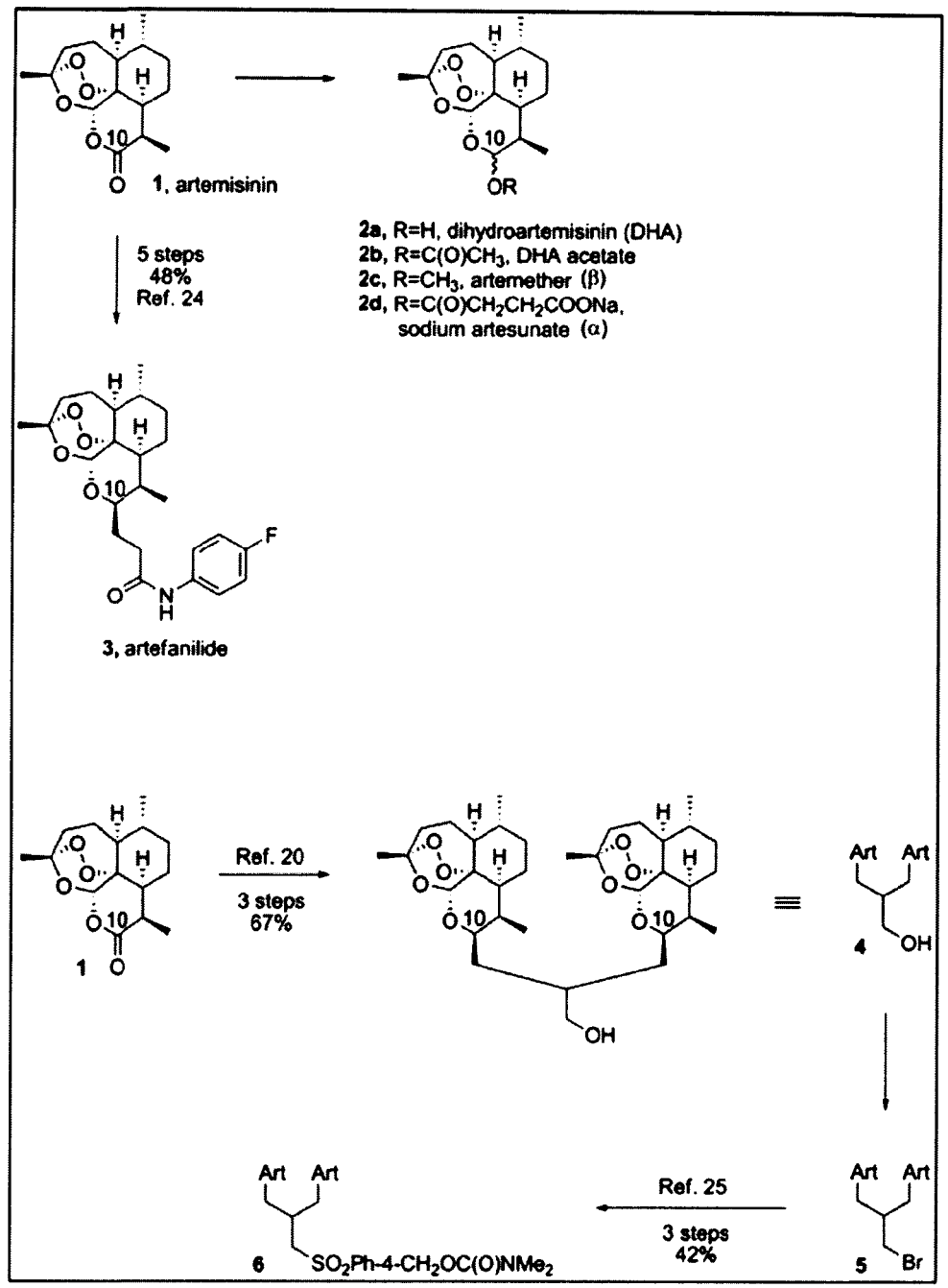
Figure 2:
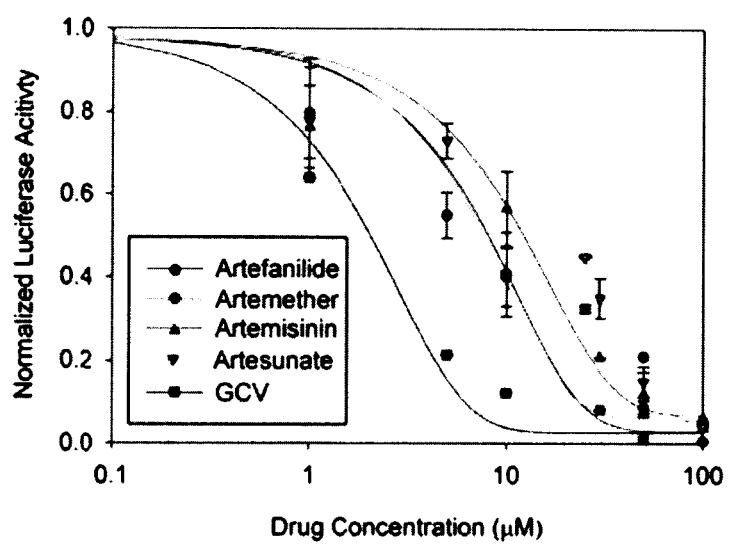
Figure 3:
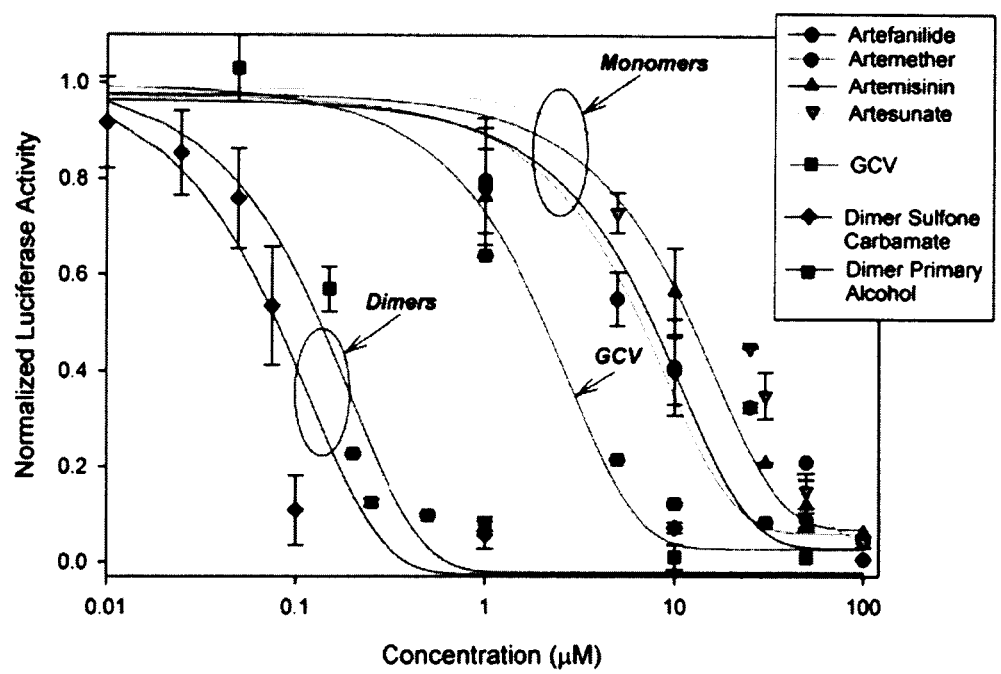
Figure 4:
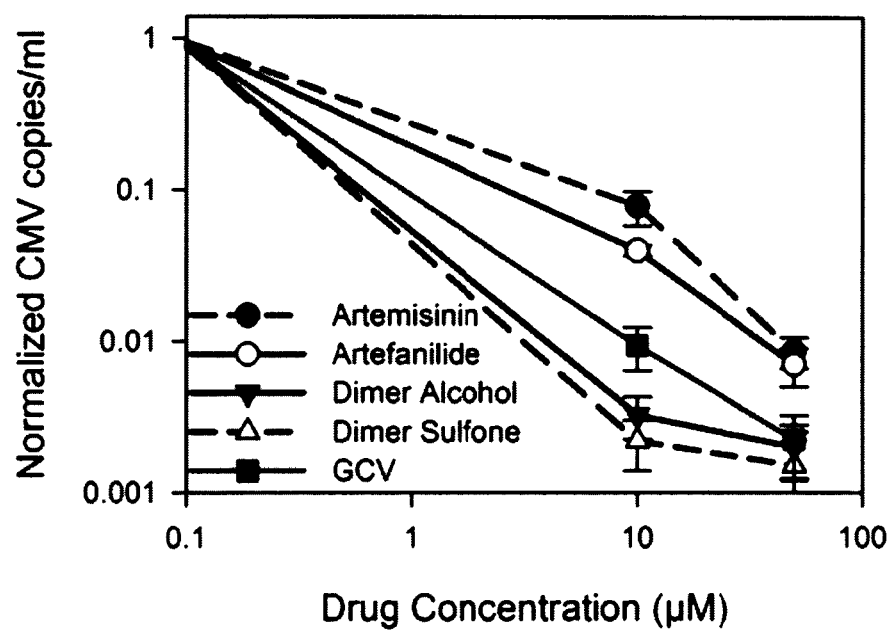
Figure 5:
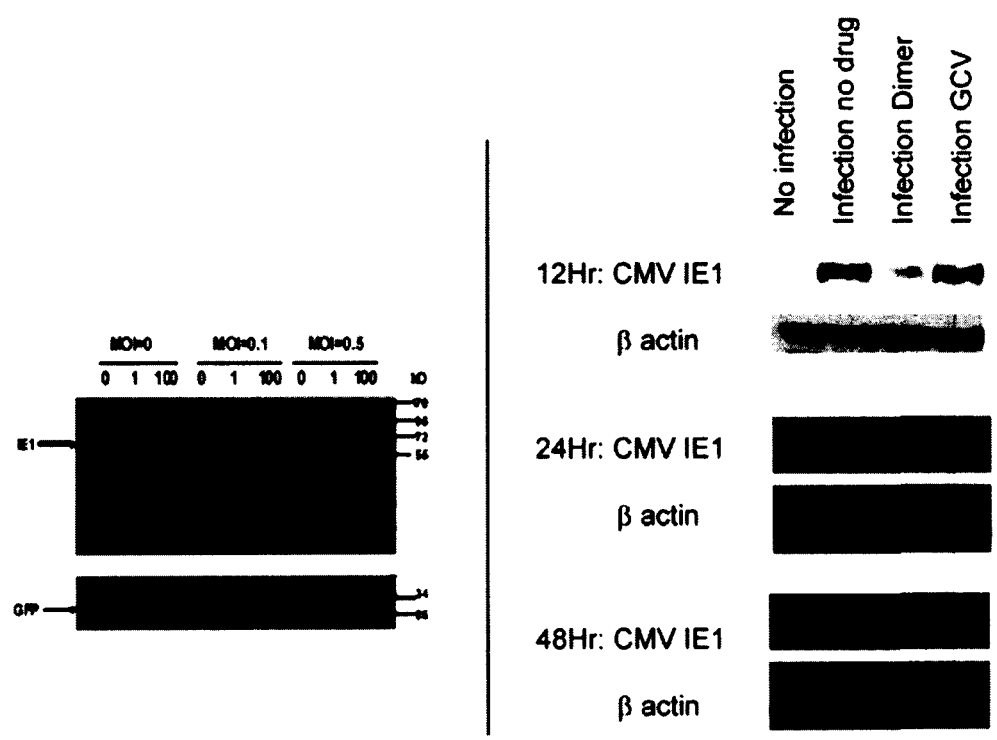
Figure 6:
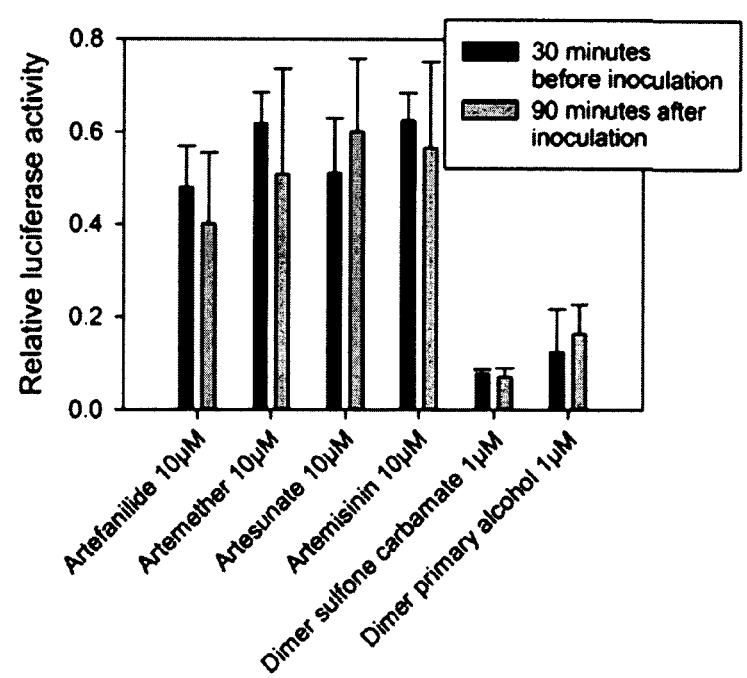

Having thus described the presently disclosed subject matter in general terms, reference will now be made to the accompanying Drawings, which are not necessarily drawn to scale, and wherein:

FIG. 1 provides representative artemisinin-derived monomers (top) and artemisinin-derived dimers (bottom) suitable for use with the presently disclosed methods;

FIG. 2 shows relative luciferase activity in CMV-infected HFF treated with artemisinin and three artemisinin-derived monomers;

FIG. 3 shows the effect of artemisinin-derived monomers and artemisinin-derived dimers on luciferase expression in CMV-infected HFF;

FIG. 4 provides CMV copies/mL at 10 days post infection in the presence of artemisinin-derived monomers and artemisinin-derived dimers;

FIG. 5 shows Western blots for IE1, GFP and 3 actin in artemisinin treated CMV infected cells;

FIG. 6 shows a comparison of CMV inhibition with artemisinin-derived monomers and artemisinin-derived dimers before infection and 90 minutes after virus inoculation.

Figure 7:
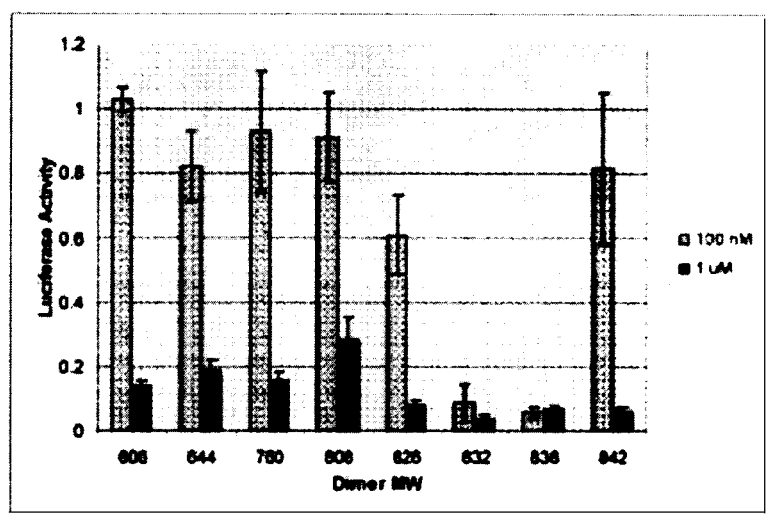
Figure 8:
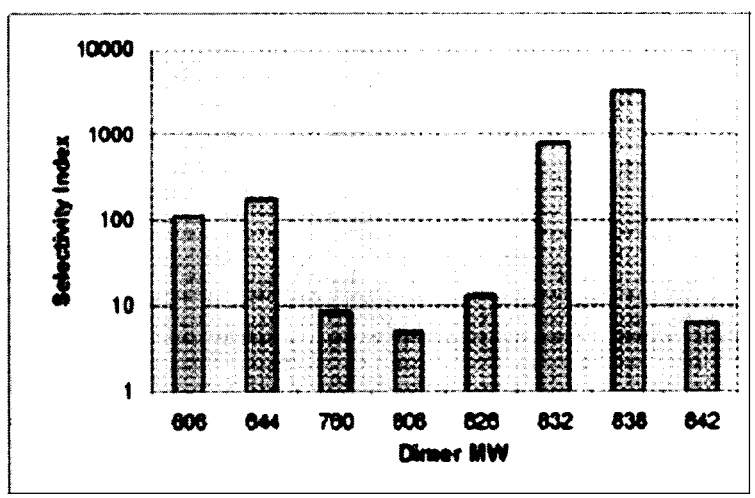
Figure 9:
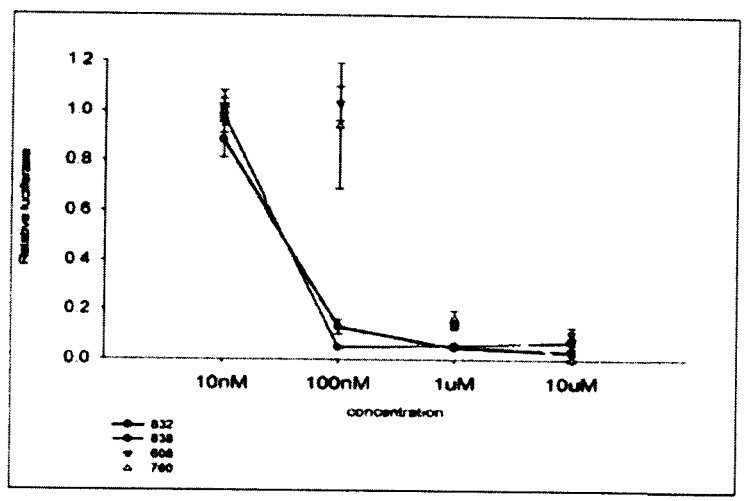

FIG. 7 shows Luciferase activity in CMV infected cells treated with eight representative presently disclosed artemisinin-derived dimers;

FIG. 8 shows a selectivity index of eight representative presently disclosed artemisinin-derived dimers; and FIG. 9 compares of the anti-CMV activity of ASR isobu-SO$_2$PhCH$_2$OC(O)NMe$_2$ (molecular weight (MW)=832), dimer isobu-OP(O)(OPh)$_2$ (MW=838), as well as their parent compounds ASR isobu-SO$_2$PhCH$_2$OH (MW=760) and dimer primary alcohol (MW=606), respectively.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

I. ANTI-CYTOMEGALOVIRUS ACTIVITY OF ARTEMISININ-DERIVED MONOMERS AND ARTEMISININ-DERIVED DIMERS

The antimalarial compound, sodium artesunate (FIG. 1 2d), a semisynthetic derivative of artemisinin (FIG. 1, 1), has good tolerability, and lacks significant adverse side effects. Adjuik M, Babiker A, Garner P, Olliaro P, Taylor W, et al. Artesunate combinations for treatment of malaria: meta-analysis. *Lancet.* 2004; 363:9-17. In addition to its antimalarial activity, artesunate is cytotoxic to several cancer cell lines. Efferth T, Dunstan H, Sauerbrey A, Miyachi H, Chitambar C R. The anti-malarial artesunate is also active against cancer. *Int J Oncol.* 2001; 18:767-773. Recently, artesunate was reported to inhibit CMV replication in-vitro and in a rat CMV model, exhibiting similar antiviral activity (same micromolar range) to ganciclovir, while demonstrating no cytotoxicity. Kaptein S J, Efferth T, Leis M, Rechter S, Auerochs S, et al. The anti-malaria drug artesunate inhibits replication of cytomegalovirus in vitro and in vivo. *Antiviral*

Res. 2006; 69:60-69; Efferth T, Marschall M, Wang X, Huong S M, Hauber I, et al. Antiviral activity of artesunate towards wild-type, recombinant, and ganciclovir-resistant human cytomegaloviruses. *J Mol Med.* 2002; 80:233-242. The in-vitro inhibition of clinical isolates ranged from 50-80% using 11.1 µM of artesunate. Efferth T, Marschall M, Wang X, Huong S M, Hauber I, et al. Antiviral activity of artesunate towards wild-type, recombinant, and ganciclovir-resistant human cytomegaloviruses. *J Mol Med.* 2002; 80:233-242. The parent substance, artemisinin, had lower anti-CMV activity compared to artesunate.

Dihydroartemisinin (FIG. 1 2a, DHA), artemether (2c) and artesunate (2d) were originally prepared in China in the 1970s. These derivatives and others, including artemisone, arteether and artelinic acid, are known as monomeric artemisinins. Artemisinin dimers were later synthesized for use as a single dose therapy for malaria to improve compliance. These orally active compounds display potent antimalarial and anticancer activities. Posner G H, Paik I H, Sur S, McRiner A J, Borstnik K, et al. Orally active, antimalarial, anticancer, artemisinin-derived trioxane dimers with high stability and efficacy. *J Med Chem.* 2003; 46:1060-1065; Alagbala A A, McRiner A J, Borstnik K, Labonte T, Chang W, et al. Biological mechanisms of action of novel C-10 non-acetal trioxane dimers in prostate cancer cell lines. *J Med Chem.* 2006; 49:7836-7842. Other than artemisinin and artesunate, artemisinin-derived monomers and artemisinin-derived dimers have not been tested as potential anti-CMV compounds.

The presently disclosed subject matter demonstrates the in-vitro anti-CMV activity of four artemisinin monomers: artemisinin (1), artesunate (2d), artemether (2c), and artefanilide (3) and representative artemisinin-derived dimers. More particularly, the presently disclosed subject matter demonstrates that, based on the concentration required for complete inhibition of CMV replication, artemisinin-derived dimers have up to 500-fold higher activity against CMV replication than the artemisinin monomers.

Accordingly, the presently disclosed subject matter demonstrates that artemisinin-derived dimers are potent inhibitors of CMV replication in-vitro with no significant cytotoxicity. CMV inhibition by artemisinin-derived dimers was up to 500-fold higher as compared to the four artemisinin monomers tested: artemisinin, artesunate, artemether and artefanilide. The presently disclosed results were comparable using several anti-viral assays and different viral strains, including a laboratory adapted strain (Towne) and a clinical isolate.

CMV is an important pathogen in solid organ transplantation, Sia I G, Patel R. New strategies for prevention and therapy of cytomegalovirus infection and disease in solid-organ transplant recipients. *Clin Microbiol Rev.* 2000; 13:83-121, in patients with AIDS, Yust I, Fox Z, Burke M, Johnson A, Turner D, et al. Retinal and extraocular cytomegalovirus end-organ disease in HIV-infected patients in Europe: a EuroSIDA study, 1994-2001. *Eur J Clin Microbiol Infect Dis.* 2004; 23:550-559, and when transmitted during pregnancy from mother to fetus. Demmler G J. Infectious Diseases Society of America and Centers for Disease Control. Summary of a workshop on surveillance for congenital cytomegalovirus disease. *Rev Infect Dis.* 1991; 13:315-329. In addition to these well-documented syndromes, CMV replication has been recently reported in immunocompetent individuals requiring medical care in intensive care units, and in patients with glioblastoma multiforme. Limaye A P, Kirby K A, Rubenfeld G D, Leisenring W M, Bulger E M, et al. Cytomegalovirus reactivation in critically ill immunocompetent patients. *JAMA.* 2008; 300:413-422; Mitchell D A, Xie W, Schmittling R, Learn C, Friedman A, et al. Sensitive detection of human cytomegalovirus in tumors and peripheral blood of patients diagnosed with glioblastoma. *Neuro Oncol.* 2008; 10:10-18. Thus, the target population for CMV therapeutics may be growing.

Drugs currently licensed in the US to treat CMV target the viral DNA polymerase and block elongation of the viral DNA chain. They are highly effective in prevention and treatment of CMV disease. Toxicities, development of drug resistance and inhibition of the host's immune response to CMV, however, are major limitations to their use. New anti-CMV drugs have been developed to overcome these drawbacks. Maribavir, targeting the UL97 kinase, Krosky P M, Baek M C, Coen D M. The human cytomegalovirus UL97 protein kinase, an antiviral drug target, is required at the stage of nuclear egress. *J Virol.* 2003; 77:905-914, is a potent inhibitor of laboratory and clinical isolates of CMV. Williams S L, Hartline C B, Kushner N L, Harden E A, Bidanset D J, et al. In vitro activities of benzimidazole D- and L-ribonucleosides against herpes viruses. *Antimicrob Agents Chemother.* 2003; 47:2186-2192. Despite promising results of phase II multicenter, randomized, double-blind, placebo-controlled study, Winston D J, Young J A, Pullarkat V, Papanicolaou G A, Vij R, et al. Maribavir prophylaxis for prevention of cytomegalovirus infection in allogeneic stem cell transplant recipients: a multicenter, randomized, double-blind, placebo-controlled, dose-ranging study. *Blood.* 2008; 111:5403-5410, a recent multicenter phase III study in bone marrow transplant recipients showed no statistically significant difference between maribavir and placebo in reducing the rate of CMV disease. In addition to compounds that directly inhibit viral targets, there is a growing interest in compounds that may affect host cell functions required for efficient virus replication. Schang L M, St Vincent M R, Lacasse J J. Five years of progress on cyclin-dependent kinases and other cellular proteins as potential targets for antiviral drugs. *Antivir Chem Chemother.* 2006; 17:293-320.

Artesunate (2d), a semisynthetic derivative of artemisinin (1), the active compound of the Chinese herb *Artemisia annua*, is highly active against malaria parasites. It is available orally, has good tolerability, and lacks significant side effects. Adjuik M, Babiker A, Garner P, Olliaro P, Taylor W, et al. Artesunate combinations for treatment of malaria: meta-analysis. *Lancet.* 2004; 363:9-17.

Artesunate was first reported to inhibit CMV replication in-vitro similar to GCV. Efferth T, Marschall M, Wang X, Huong S M, Hauber I, et al. Antiviral activity of artesunate towards wild-type, recombinant, and ganciclovir-resistant human cytomegaloviruses. *J Mol Med.* 2002; 80:233-242. A subsequent study performed in a rat CMV model revealed that the parent compound, artemisinin, had lower anti-CMV activity compared to artesunate. Kaptein S J, Efferth T, Leis M, Rechter S, Auerochs S, et al. The anti-malaria drug artesunate inhibits replication of cytomegalovirus in vitro and in vivo. *Antiviral Res.* 2006; 69:60-69. In the first report by Efferth, Efferth T, Marschall M, Wang X, Huong S M, Hauber I, et al. Antiviral activity of artesunate towards wild-type, recombinant, and ganciclovir-resistant human cytomegaloviruses. *J Mol Med.* 2002; 80:233-242, artesunate was shown to inhibit several laboratory adapted strains and clinical isolates with the most significant inhibition observed in HEL cells infected with Towne virus. In CMV infected HFF, however, inhibition with artesunate was modest. The effect of cell culture conditions on the activity of anti-CMV activity also has been reported for maribavir, Chou S, Van Wechel L C, Marousek G I. Effect of cell culture conditions on the anticytomegalovirus activity of maribavir. *Antimicrob Agents Chemother.* 2006; 50:2557-2559, with more effective suppression of viral growth observed in HEL (lung fibroblasts) than in HFF (foreskin fibroblasts). The presently disclosed subject matter demonstrates that, in both HFF and HEL cells, artemisinin-derived dimers were significantly more effective in CMV inhibition than monomers.

Artemisinin-derived dimers were originally synthesized to provide a single dose regimen for malaria. Although the first generation of dimers was unstable, the second-generation proved to be thermally and hydrolytically stable. Posner G H, Ploypradith P, Parker M H, O'Dowd H, Woo S H, et al. Antimalarial, antiproliferative, and antitumor activities of artemisinin-derived, chemically robust, trioxane dimers. *J Med Chem*. 1999; 42:4275-4280. These orally active compounds display potent antimalarial and anticancer activities, Posner G H, Paik I H, Sur S, McRiner A J, Borstnik K, et al. Orally active, antimalarial, anticancer, artemisinin-derived trioxane dimers with high stability and efficacy. *J Med Chem*. 2003; 46:1060-1065, but they do not have an advantage over artemisinin monomers in clearing malaria parasites as observed in CMV inhibition. Multiple mechanisms may contribute to the anti-cancer activities of artemisinins, Firestone G L, Sundar S N. Anticancer activities of artemisinin and its bioactive derivatives. *Expert Rev Mol Med*. 2009; 11:e32, including inhibition of cell proliferation, induction of $G_0/G_1$ cell cycle arrest and promotion of apoptosis. Alagbala A A, McRiner A J, Borstnik K, Labonte T, Chang W, et al. Biological mechanisms of action of novel C-10 non-acetal trioxane dimers in prostate cancer cell lines. *J Med Chem*. 2006; 49:7836-7842.

New dimeric sulfones were reported to cure malaria infected mice with a single oral dose and to be selectively and powerfully cytotoxic to cancer cells. Rosenthal A S, Chen X, Liu J O, West D C, Hergenrother P J, et al. Malaria-infected mice are cured by a single oral dose of new dimeric trioxane sulfones which also are selectively and powerfully cytotoxic to cancer cells. *J Med Chem*. 2009; 52:1198-1203. The concentrations effective in cancer cells are similar to those that inhibit CMV replication.

In CMV infected cells it appears that dimers do have an enhanced CMV inhibition over monomers. These inhibitory effects appear early during virus replication cycle as evidenced by decreased expression of CMV IE1 protein, in agreement with prior work. Efferth T, Marschall M, Wang X, Huong S M, Hauber I, et al. Antiviral activity of artesunate towards wild-type, recombinant, and ganciclovir-resistant human cytomegaloviruses. *J Mol Med* 2002; 80:233-242. Decreased expression of IE1 will prevent all subsequent steps in the virus replication cycle as shown by decreased DNA synthesis (by real-time PCR) and decreased expression of late CMV proteins (pp 28-luciferase assay).

A suggested mechanism of action of artesunate in CMV infection is the inhibition of cellular pathways that play an essential role in viral replication. Efferth T, Romero M R, Wolf D G, Stamminger T, Marin J J, et al. The antiviral activities of artemisinin and artesunate. *Clin Infect Dis*. 2008; 47:804-811. In artesunate-treated infected cells, Sp1 and NF-κB as well as cellular signaling kinase phosphoinositide 3-kinase (PI3K), required for the activation of Sp1 and NF-κB, were markedly reduced. Efferth T, Marschall M, Wang X, Huong S M, Hauber I, et al. Antiviral activity of artesunate towards wild-type, recombinant, and ganciclovir-resistant human cytomegaloviruses. *J Mol Med*. 2002; 80:233-242. Although at this time the mechanism of CMV inhibition is largely unknown, better understanding of it will have important clinical implications. The presently disclosed data suggest that inhibition of CMV replication does not occur at the time of binding of CMV to the cellular receptors, because the compounds are effective even after infection. Without wishing to be bound to any one particular theory, the presently disclosed artemisinin-derived dimers are significantly more potent than monomers suggests improved binding to their specific target than the monomers.

In summary, the presently disclosed subject matter demonstrates that artemisinin-derived dimers are more inhibitory to CMV replication than artemisinin monomers, without associated cytotoxicity. Artemisinin-derived dimers, although containing only two artemisinin units, are shown herein to be much more than twice potent as anti-CMV agents than the corresponding monomeric artemisinins. The antiviral activity was observed with a laboratory adapted strain and a clinical isolate of CMV. Although experience in humans with artemisinins in CMV disease is not yet available, artesunate was successfully used to treat a child with ganciclovir-resistant CMV following bone marrow transplantation. Shapira M Y, Resnick I B, Chou S, Neumann A U, Lurain N S, et al. Artesunate as a potent antiviral agent in a patient with late drug-resistant cytomegalovirus infection after hematopoietic stem cell transplantation. *Clin Infect Dis*. 2008; 46:1455-1457.

II. METHODS OF TREATING A CYTOMEGALOVIRUS (CMV) INFECTION IN A SUBJECT OR INHIBITING CMV REPLICATION IN A CELL

Accordingly, in some embodiments, the presently disclosed subject matter provides a method for treating a herpes virus, e.g., a cytomegalovirus (CMV) or an HHV8, infection in a subject in need of treatment thereof and/or inhibiting CMV replication in a cell, the method comprising administering to the subject and/or contacting a cell with a therapeutically-effective amount of a compound selected from the group consisting of:

(a)

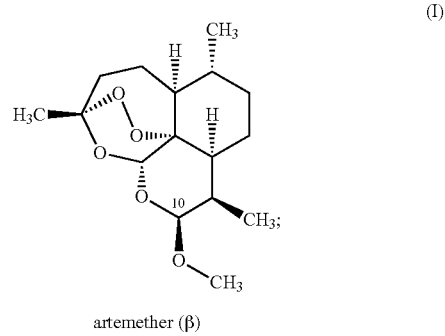

artemether (β)

(b)

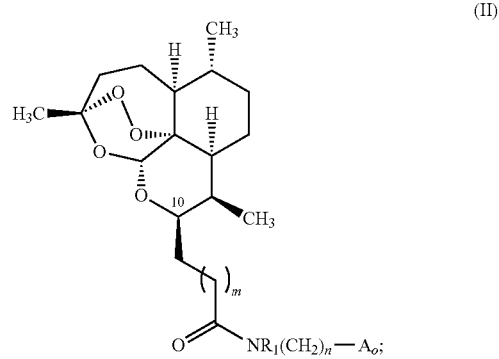

wherein:
m is an integer from 0 to 3;
n is an integer from 0 to 4;
p is an integer from 1 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

$A_0$ is selected from the group consisting of a halogen-substituted phenyl; substituted or unsubstituted heteroaryl; and —Si($R_2$)$_3$, wherein each $R_2$ is independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl; wherein such compounds and methods of preparation thereof are disclosed in International PCT Patent Publication No. WO/2010/135427 for Trioxane Monomers and Dimers, which is incorporated herein by reference in its entirety;

(c)

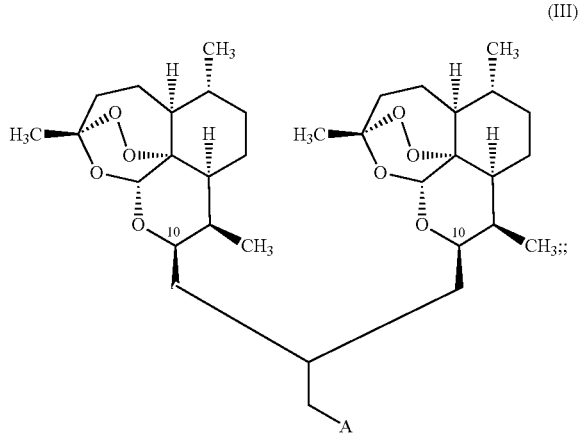

(III)

wherein:

A is —OH or S(O)$_n$—$R_1$;

n is independently an integer from 0 to 2;

$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein $R_1$ is optionally substituted with 1 to 5 $R_2$ groups;

each $R_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$OR$_3$, —(CH$_2$)$_q$O(CH$_2$)$_t$O(CH$_2$)$_u$O(CH$_2$)$_j$OR$_3$, —(CH$_2$)$_j$C(O)R$_3$, —(CH$_2$)$_j$C(O)OR$_3$, —(CH$_2$)$_j$OC(O)R$_3$, —(CH$_2$)$_j$NR$_4$R$_5$, —(CH$_2$)$_j$C(O)NR$_4$R$_5$, —(CH$_2$)$_j$OC(O)NR$_4$R$_5$, —(CH$_2$)$_j$NR$_6$C(O)R$_3$, —(CH$_2$)$_j$NR$_6$C(O)OR$_3$, —(CH$_2$)$_j$NR$_6$C(O)NR$_4$R$_5$, —(CH$_2$)$_j$S(O)$_m$R$_7$, —(CH$_2$)$_j$S(O)$_2$NR$_4$R$_5$, —(CH$_2$)$_j$NR$_6$S(O)$_2$R$_7$, or —(CH$_2$)$_j$OP(O)(OR$_7$)$_2$, wherein q is independently an integer from 0 to 20, and j, t, and u are each independently an integer from 0 to 6, and each m is independently an integer from 0 to 2, wherein $R_2$ is optionally independently substituted with 1 to 5 $R_8$ groups;

$R_3$, $R_4$, $R_5$, $R_6$, and $R_7$ are each independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or $R_3$, $R_6$, and $R_7$ are as described above, and $R_4$ and $R_5$, together with the N atom to which they are attached, form substituted or unsubstituted heterocycloalkyl, or substituted or unsubstituted heteroaryl, wherein $R_3$, $R_4$, $R_5$, $R_6$, and $R_7$ are each optionally independently substituted with 1 to 5 $R_8$ groups; and $R_8$ is independently selected from the group consisting of halogen, hydroxyl, cyano, nitro, alkyl, perfluoroalkyl, oxo. NH$_2$, NH(alkyl), N(alkyl)$_2$, O-alkyl, S-alkyl, aryl, arylalkyl, heteroaryl, and heteroarylalkyl; wherein such compounds and method of their preparation are disclosed in International PCT Patent Publication No. WO/2010/009428 for Trioxane Dimer Sulfur Compounds, which is incorporated herein by reference in its entirety.

(d)

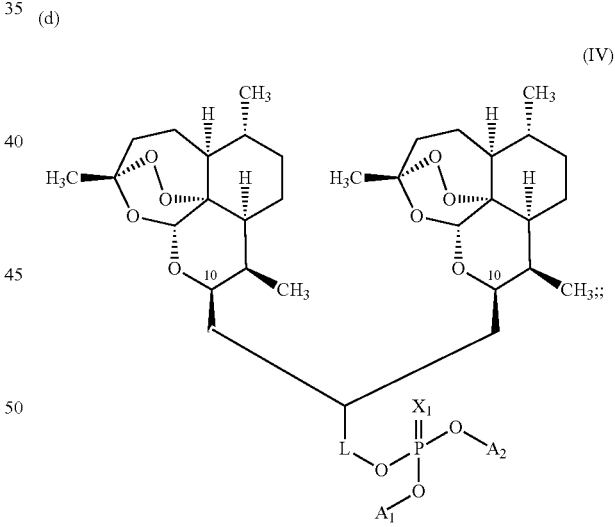

(IV)

wherein:

L is a linking group selected from (═N)— or —(CH$_2$)$_m$—, wherein m is an integer from 0 to 3;

$X_1$ is O or S;

$A_1$ and $A_2$ can be the same or different and are each independently selected from the group consisting of hydrogen, substituted or unsubstituted cycloalkyl, substituted or unsubstituted aryl, and substituted or unsubstituted heteroaryl, or $A_1$ and $A_2$ together form a substituted or unsubstituted biphenyl moiety; and (e)

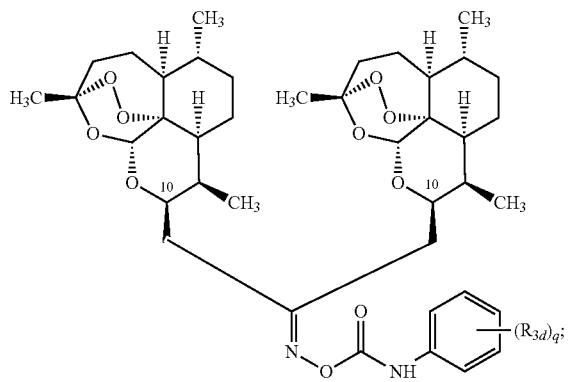

(V)

wherein:
q is an integer from 0 to 5;
each occurrence of $R_{3d}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl; or
an enantiomer, diastereomer, racemate or pharmaceutically acceptable salt, prodrug, or solvate thereof.

In some embodiments, the compound is a compound of Formula (II) and $A_0$ is a halogen-substituted phenyl:

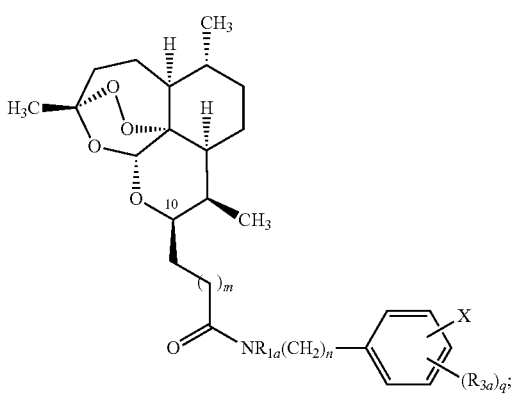

wherein:
m is an integer from 0 to 3;
n is an integer from 0 to 4;
q is an integer from 0 to 4;
X is halogen;
$R_{1a}$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl; and
each occurrence of $R_{3a}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

In some embodiments, the compound of Formula (II) is selected from the group consisting of:

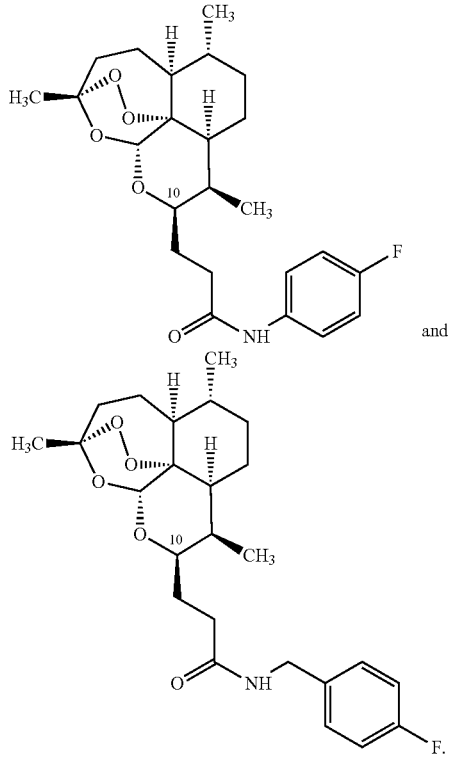

In other embodiments of the presently disclosed method, the compound is a compound of Formula (II) and $A_0$ is selected from the group consisting of 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, the compound of Formula (II) is selected from the group consisting of:

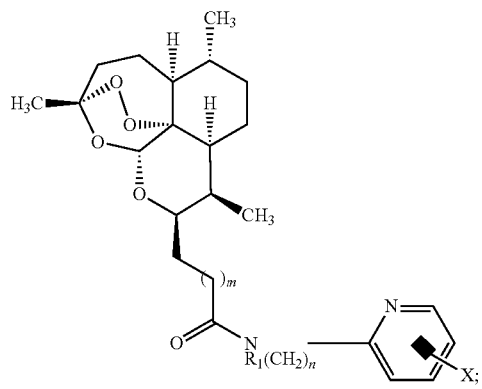

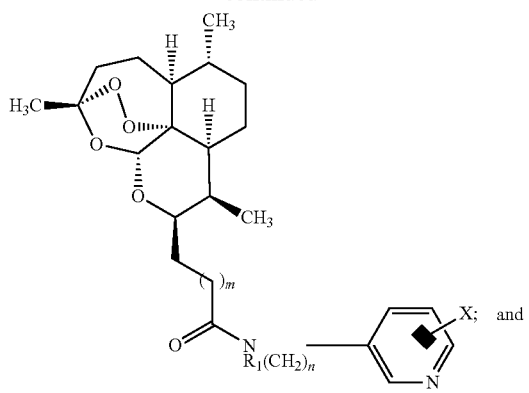
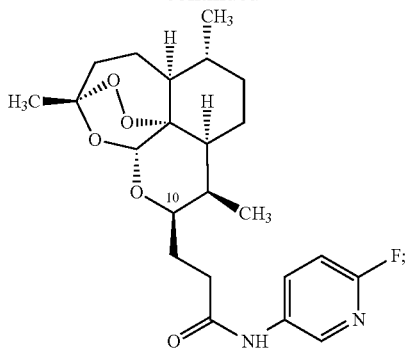
wherein X is halogen.
In some embodiments, the compound of Formula (II) is selected from the group consisting of:
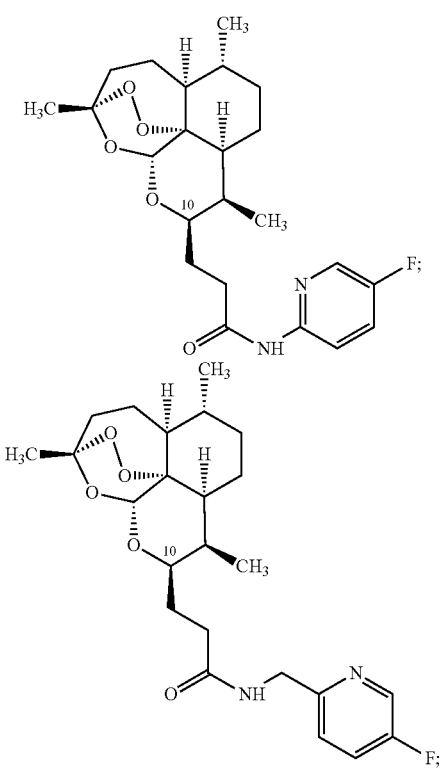
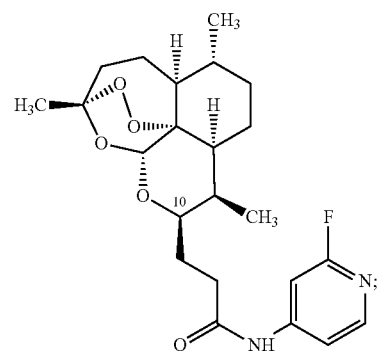
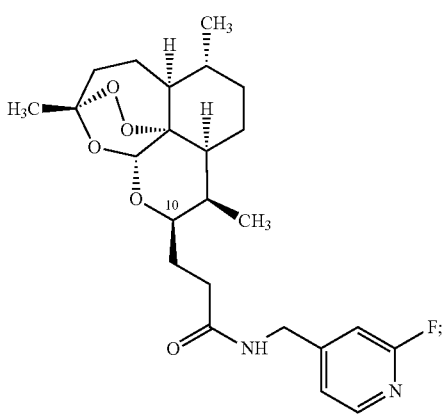

-continued

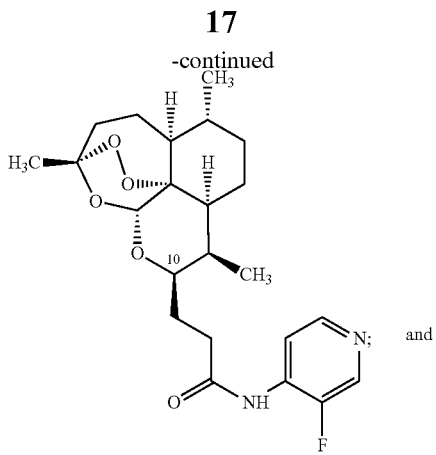 and

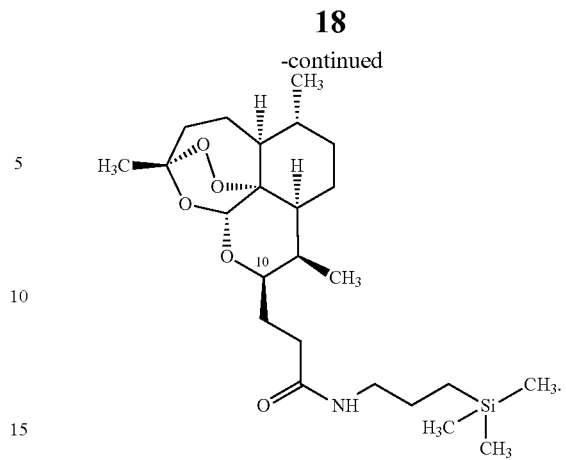

In some embodiments, the compound is a compound of Formula (II) and $A_0$ is $—Si(R_2)_3$:

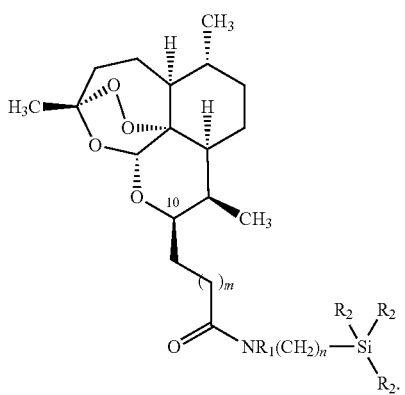

In some embodiments, the compound of Formula (II) is selected from the group consisting of:

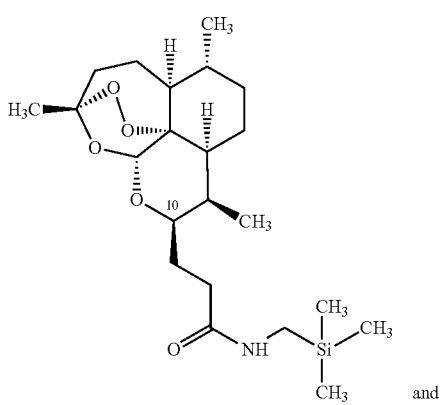 and

In yet other embodiments, the compound of Formula (III) has the following structure:

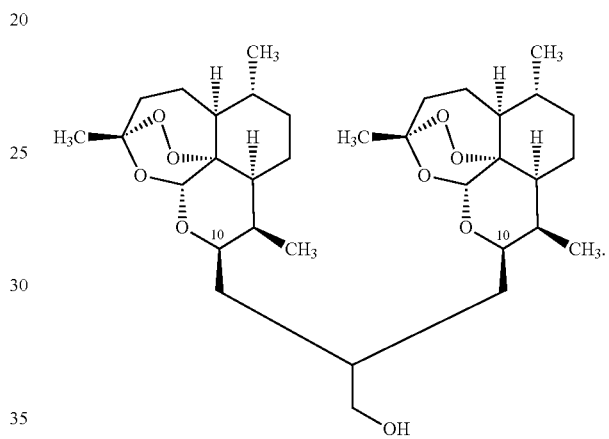

In some embodiments, the compound of Formula (III) has the following structure:

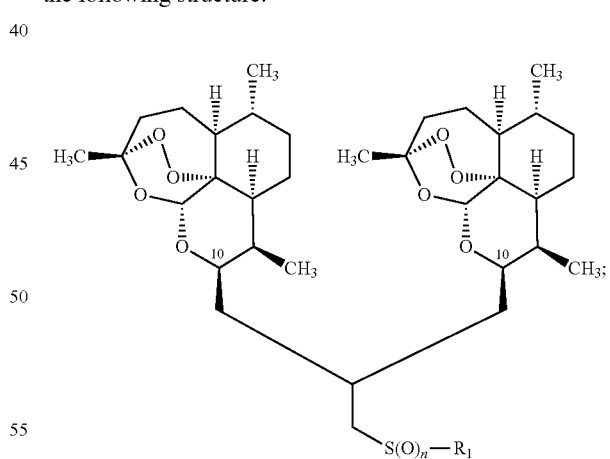

wherein:
n is independently an integer from 0 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein $R_1$ is optionally substituted with 1 to 5 $R_2$ groups;

each $R_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —$(CH_2)_jCN$, —$(CH_2)_jOR_3$, —$(CH_2)_qO(CH_2)_jOR_3$, —$(CH_2)_qO(CH_2)_tO(CH_2)_jOR_3$, —$(CH_2)_qO(CH_2)_tO(CH_2)_uO(CH_2)_jOR_3$, —$(CH_2)_jC(O)R_3$, —$(CH_2)_jC(O)OR_3$, —$(CH_2)_jOC(O)R_3$, —$(CH_2)_jNR_4R_5$, —$(CH_2)_jC(O)NR_4R_5$, —$(CH_2)_jOC(O)NR_4R_5$, —$(CH_2)_jNR_6C(O)R_3$, —$(CH_2)_jNR_6C(O)OR_3$, —$(CH_2)_jNR_6C(O)NR_4R_5$, —$(CH_2)_jS(O)_mR_7$, —$(CH_2)_jS(O)_2NR_4R_5$, —$(CH_2)_jNR_6S(O)_2R_7$, or —$(CH_2)_jOP(O)(OR_7)_2$, wherein q is independently an integer from 0 to 20, and j, t, and u are each independently an integer from 0 to 6, and each m is independently an integer from 0 to 2, wherein $R_2$ is optionally independently substituted with 1 to 5 $R_8$ groups;

$R_3$, $R_4$, $R_5$, $R_6$, and $R_7$ are each independently selected from the group 24 consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or $R_3$, $R_6$, and $R_7$ are as described above, and $R_4$ and $R_5$, together with the N atom to which they are attached, form substituted or unsubstituted heterocycloalkyl, or substituted or unsubstituted heteroaryl, wherein $R_3$, $R_4$, $R_5$, $R_6$, and $R_7$ are each optionally independently substituted with 1 to 5 $R_8$ groups; and $R_8$ is independently selected from the group consisting of halogen, hydroxyl, cyano, nitro, alkyl, perfluoroalkyl, oxo, $NH_2$, NH(alkyl), N(alkyl)$_2$, O-alkyl, S-alkyl, aryl, arylalkyl, heteroaryl, and heteroarylalkyl.

In some embodiments, n is 2; $R_1$ is independently selected from the group consisting of substituted or unsubstituted $(C_1-C_{20})$alkyl, substituted or unsubstituted $(C_1-C_{20})$heteroalkyl, substituted or unsubstituted $(C_3-C_7)$cycloalkyl, substituted or unsubstituted $(C_3-C_7)$heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl;

each $R_2$ is independently selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, substituted or unsubstituted $(C_3-C_7)$heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, substituted or unsubstituted quinoxalinyl, —$(CH_2)_jCN$, —$(CH_2)_jOR_3$, —$(CH_2)_qO(CH_2)_jOR_3$, —$(CH_2)_qO(CH_2)_tO(CH_2)_jOR_3$, —$(CH_2)_qO(CH_2)_tO(CH_2)_uO(CH_2)_jOR_3$, —$(CH_2)_jC(O)R_3$, —$(CH_2)_jC(O)OR_3$, —$(CH_2)_jOC(O)R_3$, —$(CH_2)_jNR_4R_5$, —$(CH_2)_jC(O)NR_4R_5$, —$(CH_2)_jOC(O)NR_4R_5$, —$(CH_2)_jNR_6C(O)R_3$, —$(CH_2)_3NR_6C(O)OR_3$, —$(CH_2)_jNR_6C(O)NR_4R_5$, —$(CH_2)_jS(O)_mR_7$, —$(CH_2)_jS(O)_2NR_4R_5$, —$(CH_2)_jNR_6S(O)_2R_7$, or —$(CH_2)_jOP(O)(OR_7)_2$;

$R_3$, $R_4$, $R_5$, $R_6$, and $R_7$ are each independently selected from the group consisting of hydrogen, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, substituted or unsubstituted $(C_3-C_7)$heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl, or $R_3$, $R_6$, and $R_7$ are as described above, and $R_4$ and $R_5$, together with the N atom to which they are attached, form substituted or unsubstituted pyrrolidinyl, substituted or unsubstituted imidazolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl; and each $R_8$ is independently selected from the group consisting of halogen, hydroxyl, cyano, nitro, perfluoroalkyl, oxo, $NH_2$, NH(($C_1-C_6$)alkyl), N(($C_1-C_6$)alkyl)$_2$, O($C_1-C_6$)alkyl, S($C_1-C_6$)alkyl, phenyl, biphenyl, naphthyl, benzyl, pyrrolyl, pyrazolyl, imidazolyl, furyl, thienyl, oxazolyl, isooxazolyl, thiazolyl, pyridinyl, pyridazinyl, pyrimidinyl, pyrazinyl, indolyl, indazolyl, benzimidazolyl, benzofuryl, benzothienyl, benzoxazolyl, benzoisooxazolyl, benzthiazolyl, quinolinyl, isoquinolinyl, phthalazinyl, quinazolinyl, and quinoxalinyl.

In some embodiments, $R_1$ is substituted or unsubstituted $(C_1-C_{20})$alkyl; and $R_2$ is selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, and substituted or unsubstituted $(C_3-C_7)$heterocycloalkyl.

In some embodiments, $R_1$ is substituted or unsubstituted $(C_1-C_{20})$alkyl; and each $R_2$ is independently selected from the group consisting of substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl.

In some embodiments, $R_1$ is substituted or unsubstituted $(C_1-C_{20})$alkyl; and each $R_2$ is independently selected from the group consisting
of —$(CH_2)_j$CN, —$(CH_2)_j$OR$_3$, —$(CH_2)_q$O$(CH_2)_j$OR$_3$, —$(CH_2)_q$O$(CH_2)_t$O$(CH_2)_j$OR$_3$, —$(CH_2)_q$O$(CH_2)_t$O$(CH_2)_u$O$(CH_2)_j$OR$_3$, —$(CH_2)_j$C(O)R$_3$, —$(CH_2)_j$C(O)OR$_3$, —$(CH_2)_j$OC(O)R$_3$, —$(CH_2)_j$NR$_4$R$_5$, —$(CH_2)_j$C(O)NR$_4$R$_5$, —$(CH_2)_j$OC(O)NR$_4$R$_5$, —$(CH_2)_j$NR$_6$C(O)R$_3$, —$(CH_2)_j$NR$_6$C(O)OR$_3$, —$(CH_2)_j$NR$_6$C(O)NR$_4$R$_5$, —$(CH_2)_j$S(O)$_m$R$^7$, —$(CH_2)_j$S(O)$_2$NR$_4$R$_5$, —$(CH_2)_j$NR$_6$S(O)$_2$R$_7$, or —$(CH_2)_j$OP(O)(OR$_7$)$_2$.

In some embodiments, each $R_2$ is independently selected from the group consisting of —$(CH_2)_j$OR, —$(CH_2)_q$O$(CH_2)_j$OR$_3$, —$(CH_2)_q$O$(CH_2)_t$O$(CH_2)_j$OR$_3$, and —$(CH_2)_q$O$(CH_2)_t$O$(CH_2)_u$O$(CH_2)_j$OR$_3$. In some embodiments. $R_3$ is hydrogen.

In some embodiments, $R_1$ is substituted or unsubstituted phenyl; and each $R_1$ is independently selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, and substituted or unsubstituted $(C_3-C_7)$heterocycloalkyl.

In some embodiments, $R_1$ is substituted or unsubstituted phenyl; and each $R_2$ is independently selected from the group consisting of substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl.

In some embodiments, $R_1$ is substituted or unsubstituted phenyl; and each $R_2$ is independently selected from the group consisting
of —$(CH_2)_j$CN, —$(CH_2)_j$OR$_3$, —$(CH_2)_q$O$(CH_2)_j$OR$_3$, —$(CH_2)_q$O$(CH_2)_t$O$(CH_2)_j$OR$_3$, —$(CH_2)_q$O$(CH_2)_t$O$(CH_2)_u$O$(CH_2)_j$OR$^3$, —$(CH_2)_j$C(O)R$^3$, —$(CH_2)_j$C(O)OR$_3$, —$(CH_2)_j$OC(O)R$_3$, —$(CH_2)_j$NR$_4$R$_5$, —$(CH_2)_j$C(O)NR$_4$R$_5$, —$(CH_2)_j$OC(O)NR$_4$R$_5$, —$(CH_2)_j$NR$_6$C(O)R$_3$, —$(CH_2)_j$NR$_6$C(O)OR$_3$, —$(CH_2)_j$NR$_6$C(O)NR$_4$R$_5$, —$(CH_2)_j$S(O)$_m$R$_7$, —$(CH_2)_j$S(O)$_2$NR$_4$R$_5$, —$(CH_2)_j$NR$_6$S(O)$_2$R$_7$, or —$(CH_2)_j$OP(O)(OR$_7$)$_2$.

In some embodiments, each $R_2$ is independently selected from the group consisting of —$(CH_2)_j$OR$_3$, —$(CH_2)_q$O$(CH_2)_j$OR$_3$, —$(CH_2)_q$O$(CH_2)_t$O$(CH_2)_j$OR$_3$, and —$(CH_2)_q$O$(CH_2)_t$O$(CH_2)_u$O$(CH_2)_j$OR$_3$. In some embodiments, $R_3$ is hydrogen; $R_4$ and $R_5$ are $(C_1-C_6)$alkyl; and $R_7$ is $(C_1-C_6)$alkyl or phenyl. In some embodiments, each $R_2$ is independently selected from the group consisting of —$(CH_2)_j$OR$_3$; $R_3$ is arylalkyl; and $R_8$ is halogen. In some embodiments, the compound has the following chemical structure:

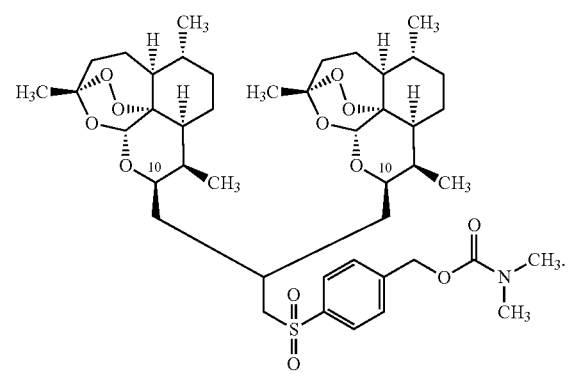

In yet other embodiments of the presently disclosed methods, the compound is a compound of Formula (IV), wherein $A_1$ and $A_2$ are each independently selected from the group consisting of hydrogen, substituted or unsubstituted cyclohexyl, substituted or unsubstituted phenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzthiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl or $A_1$ and $A_2$ together form a substituted or unsubstituted biphenyl moiety.

In some embodiments, $A_1$ and $A_2$ are each independently substituted or unsubstituted phenyl or $A_1$ and $A_2$ together form a substituted or unsubstituted biphenyl moiety and the compound of Formula (IV) has the following chemical structure:

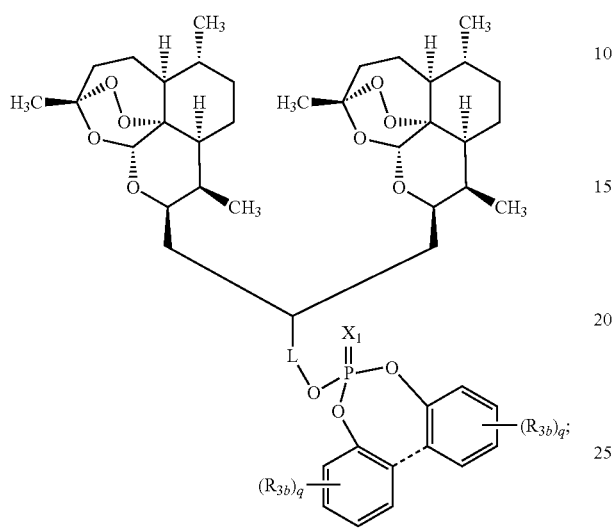

wherein:

each q is independently an integer from 0 to 5, provided that at least one occurrence of q is not 0;

the dashed line is a bond that can be present or absent; and each occurrence of $R_3$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

In some embodiments, $R_3$ is halogen or alkyl. In some embodiments, $A_1$ and $A_2$ together form a biphenyl moiety. In particular embodiments, the compound of Formula (IV) is selected from the group consisting of:

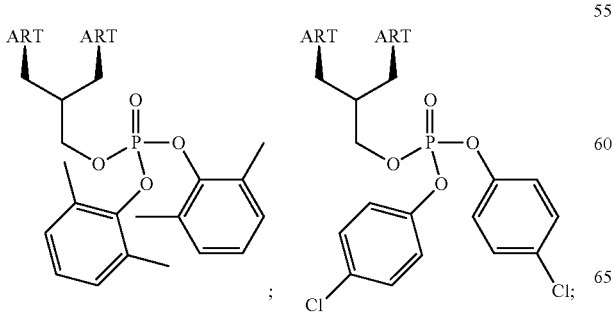

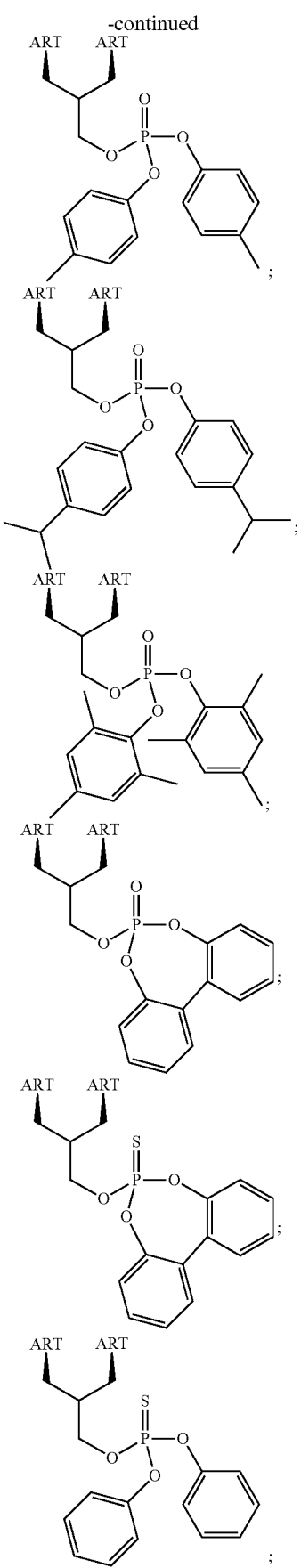

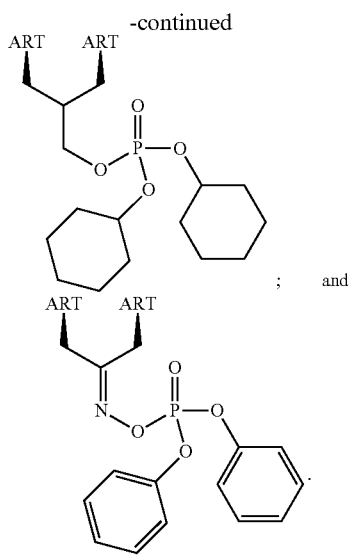

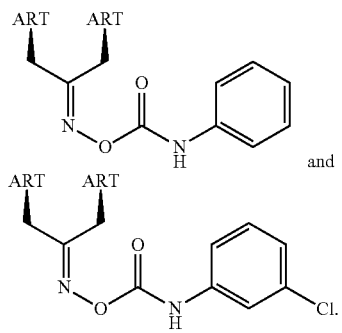

In yet other embodiments of the presently disclosed methods the compound is a compound of Formula (V), and the compound of Formula (V) is selected from the group consisting of:

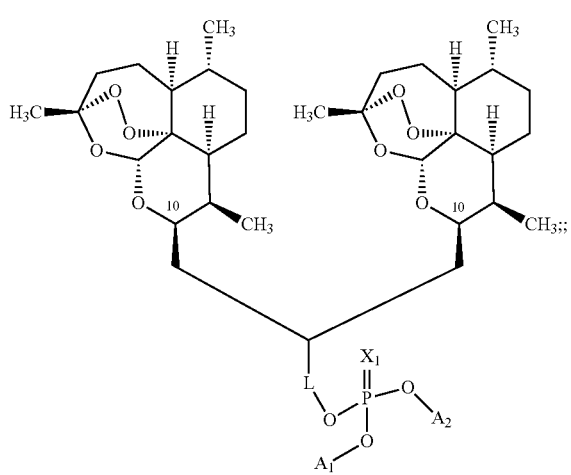

In some embodiments, the treating comprises a prophylactic treatment.

III. DIMER DIARYL OR DICYCLOALKYL PHOSPHATE ESTERS OR DIMER DIARYL OR DICYCLOALKYL THIOPHOSPHATE ESTERS OF FORMULA (IV)

In some embodiments, the presently disclosed subject matter provides a compound of Formula (IV):

(IV)

wherein:
L is a linking group selected from (=N)— or —(CH$_2$)$_m$—, wherein m is an integer from 0 to 3;
X$_1$ is O or S;
A$_1$ and A$_2$ can be the same or different and are each independently selected from the group consisting of hydrogen, substituted or unsubstituted cycloalkyl, substituted or unsubstituted aryl, and substituted or unsubstituted heteroaryl, or A$_1$ and A$_2$ together form a substituted or unsubstituted biphenyl moiety;
or an enantiomer, diastereomer, racemate or pharmaceutically acceptable salt, prodrug, or solvate thereof.

In some embodiments, A$_1$ and A$_2$ are each independently selected from the group consisting of substituted or unsubstituted cyclohexyl, substituted or unsubstituted phenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl or A$_1$ and A$_2$ together form a substituted or unsubstituted biphenyl moiety.

In some embodiments, A$_1$ and A$_2$ are each independently substituted or unsubstituted phenyl or A$_1$ and A$_2$ together form a substituted or unsubstituted biphenyl moiety and the compound of Formula (IV) has the following chemical structure:

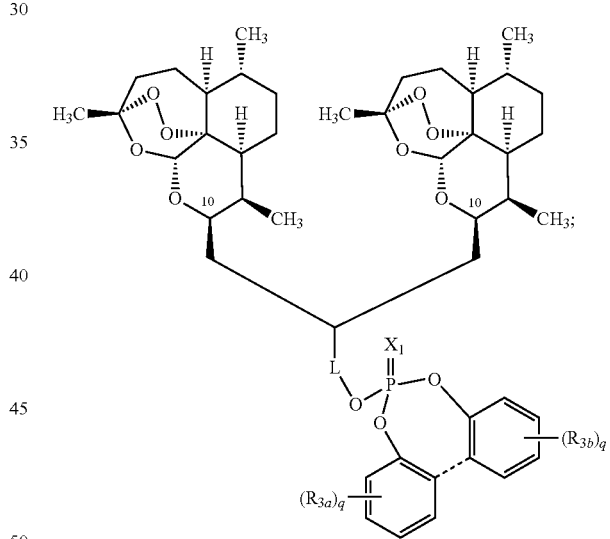

wherein:
each q is independently an integer from 0 to 5, provided that at least one occurrence of q is not 0;
the dashed line is a bond that can be present or absent; and
each occurrence of R$_3$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

In some embodiments, R$_3$ is halogen or alkyl. In other embodiments, A$_2$ together form a biphenyl moiety.

In some embodiments, the compound of Formula (IV) is selected from the group consisting of:

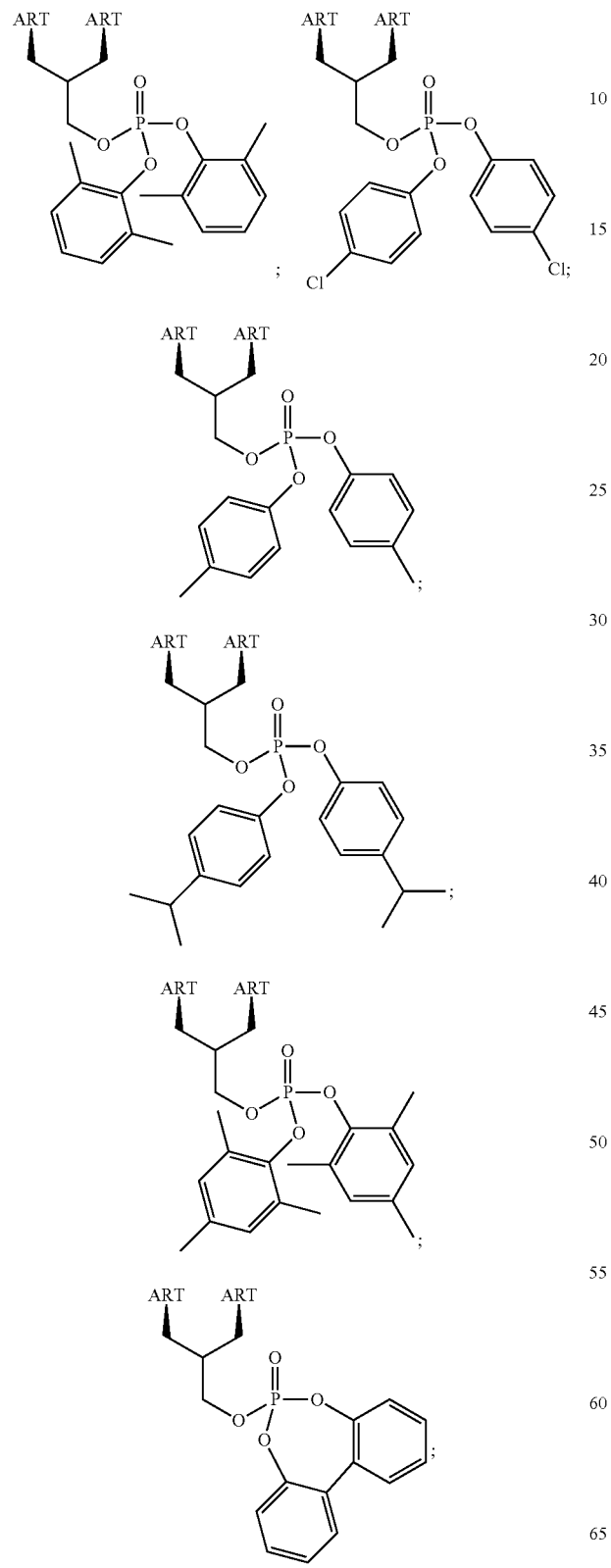

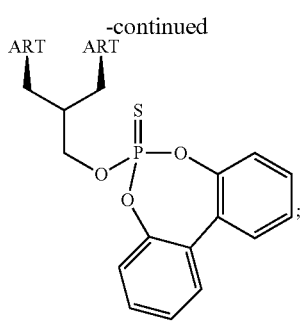

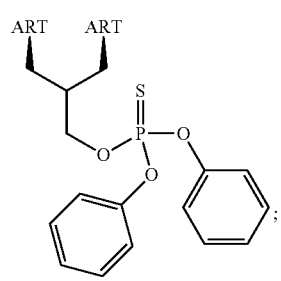

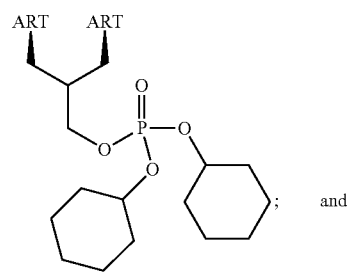

and

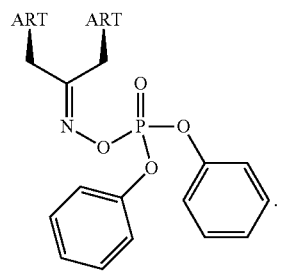

The presently disclosed subject matter also includes metabolites, e.g., mono- and/or bis-hydrolysis products of compounds of Formula (IV). In such embodiments, either A$_1$ or A$_2$, or both, are hydrogen.

In yet other embodiments, the compounds of Formula (IV) can be prepared as a salt, e.g., any pharmaceutically acceptable salt as provided hereinbelow, wherein either A$_1$ or A$_2$, or both, are replaced by a suitable metal ion.

IV. COMPOUNDS OF FORMULA (V)

In some embodiments, the presently disclosed subject matter provides a compound of Formula (V):

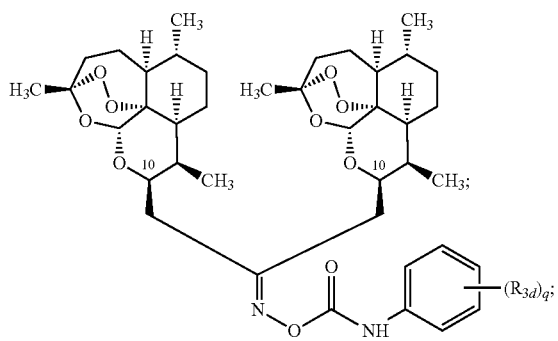

(V)

wherein:

q is an integer from 0 to 5;

each occurrence of $R_3$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl; or an enantiomer, diastereomer, racemate or pharmaceutically acceptable salt, prodrug, or solvate thereof.

In some embodiments, the compound of Formula (V) is selected from the group consisting of:

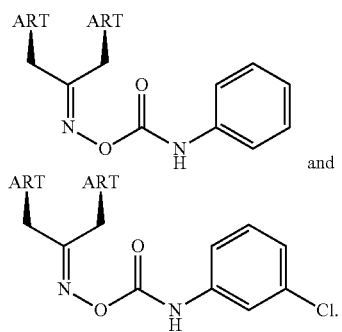

and

V. PHARMACEUTICAL COMPOSITIONS AND ADMINISTRATION

In some embodiments, the presently disclosed subject matter provides a pharmaceutical composition including one or more presently disclosed artemisinin-derived monomers or artemisinin-derived dimers alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20th ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20th ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

VI. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to the presently disclosed compounds are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{25}$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$C≡CCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

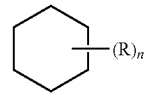

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

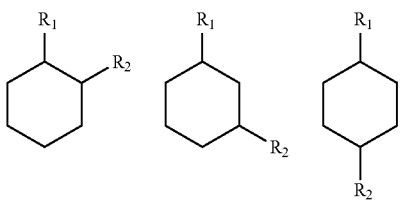

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol (〰〰) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"OR'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"OR'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids like arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

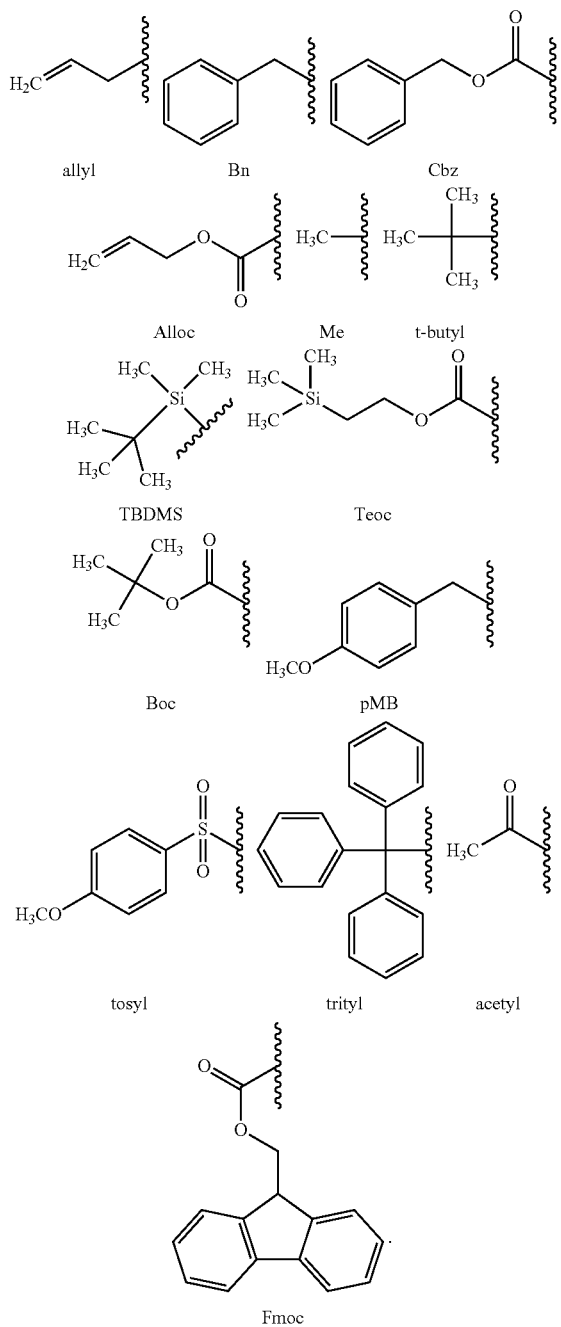

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Cells and Viruses

Human Foreskin Fibroblasts (HFF) passage 12-16 and human lung fibroblasts (HEL) passage 8-12 (from ATCC) were maintained in DMEM containing 10% fetal bovine serum and used for infections with the viruses. Cells in concentrations of $5 \times 10^4$ and $1 \times 10^4$ were seeded 24 hours prior to infection on each well of 24- and 96-well plates respectively.

The CMV strains used for infections were the highly-passaged Towne virus, and a clinical isolate obtained from the urine of a neonate with congenital CMV infection (SB) and passaged once in tissue culture. Experiments were performed with multiplicity of infection (MOI) of 0.1, 0.5, 1, and 3. Initial experiments were performed using a recombinant human CMV-green fluorescent protein (GFP) virus, derived from Towne strain. This virus has a 9-kb deletion from the dispensable unique short (US) region from US1 to US12, and instead contains the bacterial artificial chromosome sequences and a GFP expression cassette. Marchini A, Liu H, Zhu H. Human cytomegalovirus with IE-2 (UL122) deleted fails to express early lytic genes. *J Virol.* 2001; 75:1870-1878.

Based on pilot experiments using Towne-GFP, a more sensitive luciferase reporter system was selected to evaluate potential differences in CMV inhibition by various artemisinin derivatives. A recombinant virus expressing luciferase reporter gene under the control of UL99 (pp 28) late promoter was generated by insertion of the reporter gene between the US9 and US10 ORFs in the Towne genome. This extragenic reporter gene displays authentic late transcription characteristics after infection of HFF. Ahn J H, Hayward G S. Disruption of PML-associated nuclear bodies by IE1 correlates with efficient early stages of viral gene expression and DNA replication in human cytomegalovirus infection. *Virology.* 2000; 274:39-55. Pp 28-luciferase expression is strongly activated at 48-72 hours and is almost completely inhibited in the presence of DNA synthesis inhibitors (GCV).

Example 2

Antiviral Assays

Towne-GFP, Towne-luciferase, and SB viruses were used in these assays. HFF or HEL were grown to subconfluent monolayers and infected with the CMV viruses at MOI 0.1 to 3. Based on previously reported methods, cells were treated with artemisinin derivatives at various concentrations and infected with CMV 30 min thereafter. Efferth T, Marschall M, Wang X, Huong S M, Hauber I, et al. Antiviral activity of artesunate towards wild-type, recombinant, and ganciclovir-resistant human cytomegaloviruses. *J Mol Med.* 2002; 80:233-242. The concentration of each compound was calculated and adjusted by volume such that it was constant throughout the experiment. Following 90 minute incubation, media was replaced with fresh media containing the drug used. Infected and treated cells were incubated at 37° C. in a 5% $CO_2$ atmosphere for 3-10 days depending on the virus and the anti-viral assay. The recombinant luciferase-expressing virus was incubated for 72 hours, the GFP virus was incubated for 5 days, and the clinical isolate for 10 days. All experiments were subsequently repeated with compounds added to wells just after viral inoculation.

For luciferase assay, Wizard® SV Lysis Buffer (Promega, Madison, Wis.) was added to each well, incubated for 10 minutes at 37° C., followed by 10 minutes of freezing at −80° C. and incubation at 37° C. for 10 minutes. Luciferase activity was determined in cell extracts using an automated luminescent assay (Promega, Madison, Wis.). The dynamic range of the luciferase assay is 6-7 logs, and data obtained with it highly correlates with real-time PCR and with plaque reduction assay (manuscript in preparation). Cellular cytotoxicity was determined using CellTiter-Glo® Luminescent Cell Viability Assay (Promega, Madison, Wis.). The assay determines the number of viable cells in culture based on quantification of the ATP present.

For plaque reduction assay, human embryonic lung cells were seeded into six-well plates and incubated at 37° C. one day prior to infection with the recombinant luciferase-expressing CMV. Serial dilutions of GCV, artesunate and artefanilide were used. The virus was diluted to a desired concentration which gave 50-60 plaques per well. Medium was aspirated from the wells, and 0.2 ml of virus suspension was added to each well in triplicates. Plates were incubated for 90 minutes with shaking every 10 min, thereafter drugs were added and a methylcellulose overlay applied to each well. After incubation for 10 days, cells were stained with crystal violet. The stain was aspirated, wells were washed with phosphate-buffered saline, and plaques were counted.

Example 3

Western Blot for IE-1 and IE-2

Monoclonal antibodies to CMV immediate early proteins IE-1 and IE-2 (MAb810) and to cellular β-actin were purchased from Millipore (Billerica, Mass.). Confluent cells were infected with CMV in the presence of artemisinin compounds. At the indicated times cells were harvested in sample buffer (RIPA buffer, Tris 50 mM, Nacl 150 mM, SDS 0.1%, Na Deoxycholate 0.5%, NP40 1%, and protease inhibitor cocktail), boiled and loaded onto SDS-PAGE. Proteins were separated by electrophoresis and transferred to nitrocellulose membrane. After blocking, blots were probed with primary antibody (1:3,000) overnight at 4° C. in phosphate-buffered saline, and Tween. After washing 3 times, blots were probed with HRP-conjugated anti-mouse (Sigma), 1:5,000 for 1 hour at room temperature. Blots were washed three times in phosphate-buffered saline/Tween, and then developed by enhanced chemiluminescence according to manufacturer protocol.

Example 4

CMV US17 Real-Time PCR Assay

To determine the inhibitory effects of artemisinins on DNA copy number of SB clinical CMV isolate, real-time PCR was performed. DNA was isolated from infected cells 10 days post infection using Wizard® SV Genomic DNA Purification System (Promega, Madison, Wis.). The real-time PCR is based on detection of the highly conserved US17 gene. Tanaka Y, Kanda Y, Kami M, Mori S, Hamaki T, et al. Monitoring cytomegalovirus infection by antigenemia assay and two distinct plasma real-time PCR methods after hematopoietic stem cell transplantation. *Bone Marrow Transplant.* 2002; 30:315-319. The primers and probe for US17 are: forward-5' GCGTGCTTTTTAGCCTCTGCA-3', reverse 5'-AAAAGTTTGTGCCCCAACGGTA-3' and US17 probe FAM-5' TGATCGGGCGTTATCGCGTTCT-3'. The limit of detection is 10 copies/reaction (100 copies/mL) and the dynamic range of the assay is 2.4-8.0 $\log_{10}$ copies/mL.

Example 5

Compounds

Ganciclovir (GCV) was obtained from Roche, USA and stock was prepared in aqueous solution. Artemisinin (1) was obtained from Sigma-Aldrich. Artesunate (2d), artemether (2C), artefanilde (3), dimer primary alcohol (4) and dimer sulfone dimethyl carbamate (6) were synthesized at Johns Hopkins University (GHP). Rosenthal A S, Chen X, Liu J O, West D C, Hergenrother P J, et al. Malaria-infected mice are cured by a single oral dose of new dimeric trioxane sulfones which are also selectively and powerfully cytotoxic to cancer cells. *J Med Chem.* 2009; 52:1198-1203. Stocks of artemisinin monomers and dimers were prepared in dimethyl sulfoxide (DMSO) and stored in −20° C. Synthetic compounds were at least 98% pure based on high performance liquid chromatography. The DMSO itself was tested in CMV-infected cells and it did not have any anti-viral activity. FIG. 1 depicts the monomers and dimers used in this study.

Example 6

Results

Pretreatment of human foreskin fibroblasts (HFF) with different concentrations of artemisinin (1) followed by infection with GFP-tagged CMV resulted in dose-dependent reduction in CMV replication (data not shown). To better quantify the extent of reduction and to compare the degree of CMV inhibition by different artemisinin derivatives all subsequent experiments of CMV inhibition were performed using the highly sensitive luciferase assay and the pp 28-luciferase expressing CMV.

The four monomers, artemisinin, artesunate, artemether and artefanilide (FIG. 1), were tested first for CMV inhibition in comparison with GCV. These monomers exhibited a similar degree of anti-CMV activity. At 10 μM, ganciclovir (GCV) was more potent in CMV inhibition than all four monomers (FIG. 2). Similar results were obtained by a plaque reduction assay performed in human embryonic lung cells (HEL) with the same luciferase virus; at 10 μM, monomers achieved 40-50% reduction in plaque formation, while GCV reached 80% reduction in plaque formation.

CMV inhibition by the four monomers and two dimmers was evaluated next. Artemisinin dimers (FIG. 1 (4) and (6)) were significantly more efficient than the monomers in inhibition of pp 28-driven luciferase activity (FIG. 3, P<0.0001) without associated cellular cytotoxicity (Table 1). The dimers were up to 500-fold more potent than monomers in achieving complete inhibition of CMV replication. Data presented in the figures was obtained from CMV infected HFF. The same phenomenon of CMV inhibition with dimers compared to monomers also was observed in HEL cells. Error bars presented in FIGS. 2 and 3 represent the standard deviation of six experiments, each with three replicates. Normalized luciferase activity is shown as the ratio of luminescence units measured in drug treated CMV-infected cells vs. non-treated CMV-infected cells.

TABLE 1

$EC_{50}$, $CC_{50}$ and selectivity index (SI) for monomers, dimers and GCV.

| Compound | $CC_{50}$ (μM) | $EC_{50}$ (μM) | Selectivity index (SI) |
| --- | --- | --- | --- |
| Dimer sulfone carbamate (6) | 28.1 ± 9.6 | 0.06 ± 0.00 | 508 ± 173 |
| Dimer primary alcohol (4) | 57 ± 2.3 | 0.15 ± 0.02 | 380 ± 53 |
| GCV | 247 ± 33.4 | 5.6 ± 0.2 | 44 ± 6.2 |
| Artemisinin (1) | 72.4 ± 15.7 | 16.8 ± 4.0 | 4.3 ± 1.4 |
| Artesunate (2d) | 77.5 ± 14.4 | 18.5 ± 5.2 | 4.2 ± 2.2 |
| Artemether (2c) | 18.4 ± 7.5 | 5.3 ± 2.7 | 3.5 ± 2.2 |
| Artefanilide (3) | 44.9 ± 3.4 | 8.1 ± 2.2 | 5.5 ± 1.6 |

Dimer primary alcohol (4) and dimer sulfone carbamate (6) were reproducibly associated with dramatic inhibition of CMV replication using different batches and passages of HFF, and HEL cells.

To confirm that dimers did not block the luciferase enzyme in the recombinant virus, which could have resulted in low luciferase values, whole cell extracts of CMV-infected cells were treated with either dimer primary alcohol or DMSO only. Luciferase activity, measured after 30 minutes of incubation, revealed that luminescence was similar between the dimer-treated (83,200±1,670 units) and the DMSO-treated cells (86,300±2,490), supporting the observation that dimers did not affect the luciferase enzyme itself, but rather inhibited CMV replication.

Differences in anti-CMV activity between artemisinin monomers and artemisinin dimers were evaluated using a clinical isolate, SB. Cells were treated with either artemisinin monomers or dimers and DNA was extracted from cell extracts 10 days post infection. Real-time PCR showed that DNA copy number decreased 20- to 35-fold more with dimers as compared to monomers at 10 M, and 4-fold more as compared to GCV (FIG. 4).

The selectivity index (SI) of all artemisinin derivatives and GCV was calculated based on the effective drug concentration that results in 50% virus inhibition, $EC_{50}$, and the drug concentration that leads to 50% cellular cytotoxicity, $CC_{50}$ (Table 1). SI was determined as the ratio between $CC_{50}$ and $EC_{50}$. For $EC_{50}$ and $CC_{50}$ reported values represent the mean and SD of data derived from at least five independent experiments performed in triplicates. The concentrations of monomers used for calculating $EC_{50}$ were 1, 5, 10, 25, 50, and 100 M. The concentrations of dimers used for $EC_{50}$ calculations were 1 nM, 10 nM, 100 nM, 250 nM, 1 μM and 10 μM. The curve fitting toolbox, Matlab software (v7.5), Mathworks (Natick, Mass.) was used to determine $EC_{50}$ values using a four-parameter logistic regression. GCV was approximately 10 times more selective than the monomers. The dimer sulfone carbamate (6) had the highest selectivity, approximately 10 times more than GCV (Table 1).

To confirm that the difference in anti-CMV activity between monomers and dimers was not a result of instability of the monomers in tissue culture, the anti-toxoplasmosis activity of these compounds was determined in the supernatants of CMV infected cells at 3-5 days post infection. Monomers used in CMV-infected cells proved to inhibit toxoplasmosis in concentrations that correlated with previous reports (Table 2). Jones-Brando L, D'Angelo J, Posner G H, Yolken R. In vitro inhibition of *Toxoplasma gondii* by four new derivatives of artemisinin. *Antimicrob Agents Chemother.* 2006; 50:4206-4208.

TABLE 2

$EC_{50}$ of monomers and dimer primary alcohol for CMV and Toxoplasmosis.

| Compound | $EC_{50}$ (μM) - CMV | $EC_{50}$ (μM) - Toxoplasmosis |
| --- | --- | --- |
| Artemisinin | 15.7 ± 4.5 | 4.1 ± 1.1 |
| Artesunate | 17.2 ± 3.4 | 3.2 ± 0.8 |
| Artemether | 5.1 ± 2.1 | 0.58 ± 0.22 |
| Dimer Primary Alcohol | 0.16 ± 0.04 | 0.40 ± 0.15 |

The expression of CMV immediate early (IE) protein was tested by western blot to determine whether artemisinins' inhibition of CMV replication occurs early in the virus life cycle. The expression of immediate early 1 (IE1) and GFP in cell lysates treated with artemisinin and infected with Towne-GFP was decreased with 100 M artemisinin (MOI of 0.5), and undetectable using MOI of 0.1 (FIG. 5a). Further evidence for the early effect of artemisinins on IE1 protein expression was obtained with the clinical isolate (SB, FIG. 5b). IE1 expression was significantly reduced in CMV infected cells (MOI=1) treated with 1-μM dimer primary alcohol at 24 and 48 hr, but was not affected by 10 μM GCV. The inhibition of IE1 expression with dimer primary alcohol was observed as early as 12 hours post infection (SB, MOI=3), prior to onset of DNA replication. Stinski M F. Sequence of protein synthesis in cells infected by human cytomegalovirus: early and late virus-induced polypeptides. *J Virol.* 1978; 26:686-701.

To determine whether pretreatment with artemisinin monomers or dimers was necessary to achieve CMV inhibition, all experiments were repeated with infection followed by treatment. HFF were infected with pp 28-luciferase expressing CMV (MOI=1). After 90 minute incubation, unadsorbed virus was removed, and appropriate concentrations of artemisinin monomers or dimers were added. The data obtained with these sets of experiments revealed that pretreatment with the compounds is not required for their anti-CMV activity, and that the exact same degree of CMV inhibition is achieved even when the compounds are added after viral adsorption (FIG. 6).

Further, eight representative artemisinin-derived dimers were evaluated for their anti-CMV activity. Dimer isobu-OP (O)(OPh)$_2$ was the most potentCMV inhibitor with a selectivity index of >1000 (FIGS. 7 and 8).

TABLE 3
Representative Dimers.
| Dimer | MW | Structure |
|---|---|---|
| Dimer primary alcohol | 606 | 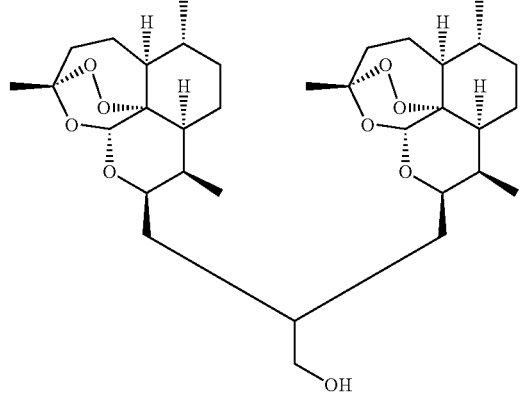 |
| Dimer isobu-OP(O)(OPh)$_2$ | 838 | 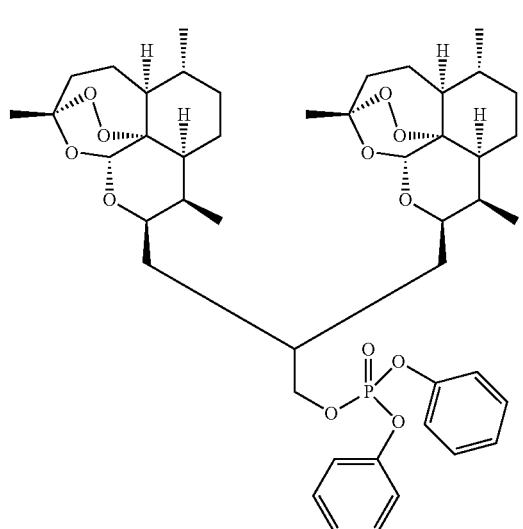 |
| ASR isobu-SO$_2$PhCH$_2$OC(O)NMe$_2$ | 832 | 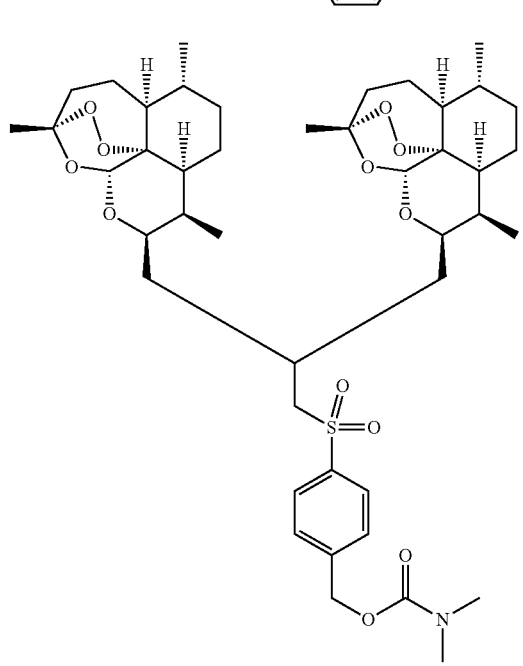 |

TABLE 3-continued

Representative Dimers.

| Dimer | MW | Structure |
|---|---|---|
| ASR isobu-SO$_2$PhCH$_2$OH Sulfone benzylic alcohol (4b) | 760 | 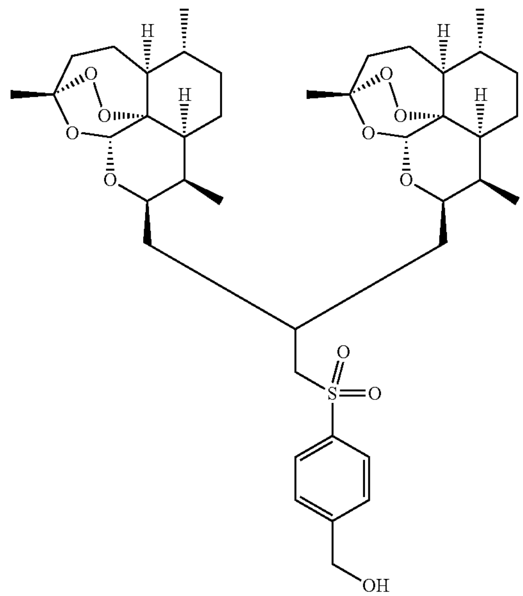 |
| DKM 5c dimer OH | 644 | 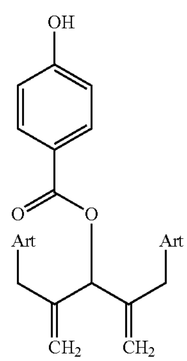 |
| DKM 5c dimer OC(O)Ph-4-SO$_2$Me | 826 | 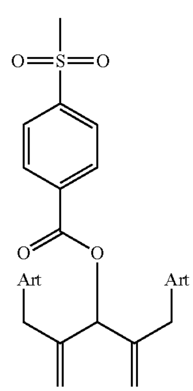 |

TABLE 3-continued

Representative Dimers.

| Dimer | MW | Structure |
|---|---|---|
| DRL, 5c dimer OC(O)NH—Ph-4-SO₂Me | 842 | 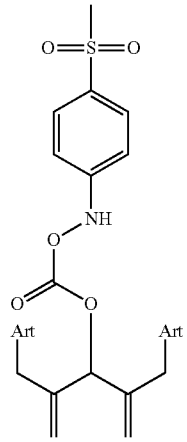 |
| DRL, 5c-dimer OC(O)NH—Ph-4-NO₂ | 808 | 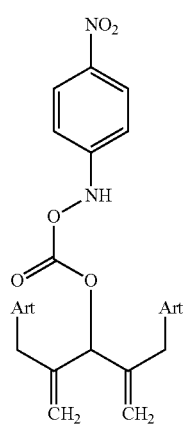 |

Initial data reveal decreased transcription of the MIE and IE1 two hours after CMV infection and treatment with dimers, followed by inhibition of IE1 protein expression. The enhancer of the MIE regulatory region consists of multiple different binding sites for cellular transcription factors (TF) that are repeated several times in its distal and proximal components. Multiple pathways are utilized by CMV for regulation of TF necessary for maintenance of the viral life cycle. Dimers may affect several pathways at different times during CMV replication, resulting in abortive CMV replication. Transactivation of the MIE following infection is required for generation of the major IE transcripts, viral replication and production of infectious virus. The MIE responds to signal transduction events and to cellular differentiation, and regulates the expression of the downstream MIE genes IE1 (UL23) and 1E2 (UL122]. Cellular TF that are induced rapidly after infection are responsible for up regulation of the MIE. NF-kB plays a critical role in the efficient transactivation of MIE, but the CRES site in the proximal enhancer also was reported to have the greatest independent effect on viral replication in different cell types. MAPKs phosphorylate and activate CREB which facilitates an interaction with the CREB binding protein (CBP). CSP interacts with other TF such as API, NF-kB, and Sp1. Although CREB and NF-kB sites are considered key components of the MIE, mutation of all CREB sites or all NF-kB sites had only little or no effect on CMV replication. Thus, either other sites compensate for the loss, or viral glycoproteins facilitate a strong activation of the MIE. CMV induces an increase in Sp-I DNA binding activity and its replication is greatly diminished with deletion of one or two Sp-1 sites. Sp-1 interacts with other Tf. Sp1 is phosphorylated by various kinases at different sites within the protein. These include cyclin dependent kinase (CD K), atypical protein kinase C-s, extracellular signal regulated kinase (ERK), case in kinase II, and DNA-dependent protein kinase. SpI phosphorylation can both positively and negatively influence transcriptional activity, for example, native Sp-I activates PDGFRα, but its phosphorylation by fibroblast growth factor (FGF-2) increases its interaction with the PDG-FRα promoter and reduces its activity.

Other methods to inhibit expression of the NF-kB pathway and the other artemisinin targets mentioned above can be envisioned in the therapy of CMV infection, including antisense constructs, antisense oligonucleotides, RNAi constructs, or siRNA duplex RNA molecules, blocking antibodies and other techniques commonly known in the art.

Further, the presently disclosed dimers were tested against Herpes simplex virus 1 (HSV1) and Herpes simplex virus 2 (HSV2) and exhibited no activity at concentrations of 100 nM, 1 μM, and 10 μM. In contrast, the presently disclosed dimers were tested against HHV8, the virus that causes Kaposi sarcoma herpes virus (KSHV), and at 100 nM exhibited a strong inhibition of latency (expression of latency-associated nuclear antigen (LANA)), but exhibited no apparent effect on lytic replication.

Example 7

Chemical Syntheses of Artemisinin-Derived Dimers

Experimental Procedures

All reactions were performed under argon in oven-dried or flame-dried glassware. Microwave reactions were performed in a Biotage Initiator microwave. Dichloromethane was dispensed from an LC Technology Solutions SPBT-1 bench top solvent purification system. All commercially available reagents were purchased from Sigma Aldrich and used as received. All experiments were monitored by thin layer chromatography (TLC) performed on Silicycle silica gel 60 Å glass supported plates with 0.25 mm thickness. Flash chromatography was performed with EMD silica gel (40-63 µM). Yields are not optimized. Infrared (IR) spectra were recorded on a Perkin Elmer 1600 FT-IR spectrometer. Nuclear magnetic resonance (NMR) spectra were recorded on a Bruker Avance 400 MHz FT-NMR spectrometer (400 MHz for $^1$H, 100 MHz for $^{13}$C). The following abbreviations are used in the experimental section for the description of $^1$H NMR spectra: singlet (s), doublet (d), triplet (t), quartet (q), multiplet (m), broad singlet (bs), doublet of doublets (dd), doublet of triplets (dt), and doublet of quartets (dq). High resolution mass spectral data was collected at the NIH Chemical Genomics Center using and Agilent 6210 time-of-flight mass spectrometer, also coupled to an Agilent Technologies 1200 series HPLC system.

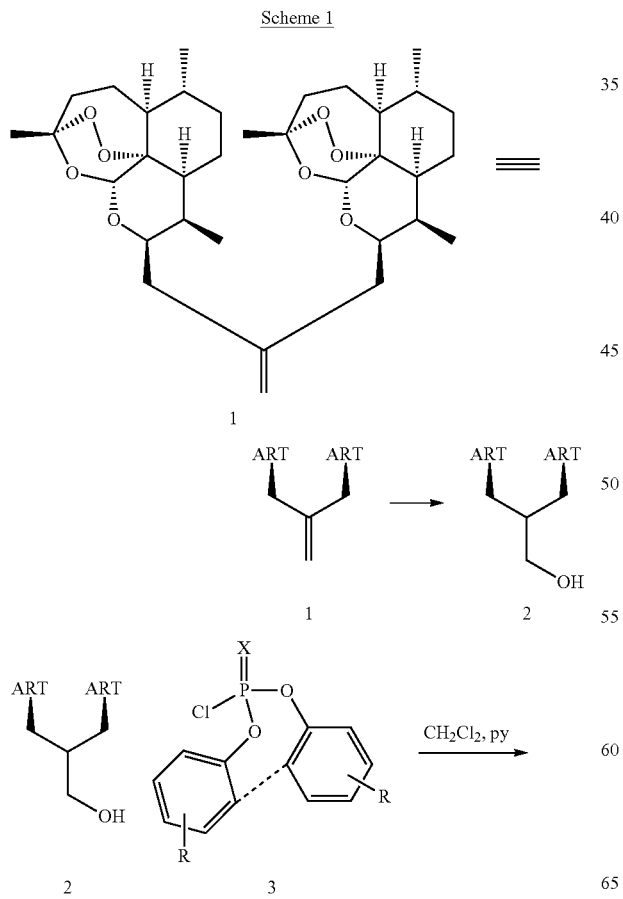

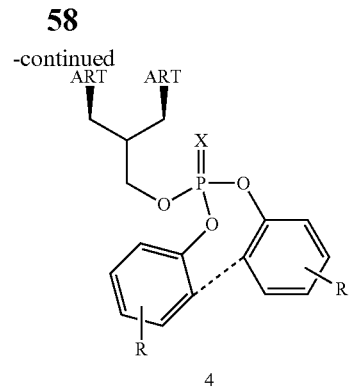

In Scheme 1, the olefinic trioxane dimer 1 and primary alcohol 2 may be prepared according to the procedures in *J Med. Chem.*, 2004, 47, 1299-1301. Further treatment of primary alcohol 2 with diaryl phosphorochloridates (where X=O) or diaryl phosphorochloridothioates (where X=S) of general structure 3 (whose synthesis is described herein) in the presence of pyridine provide new dimer diaryl phosphate esters or dimer diaryl thiophosphate esters of general structure 4.

Scheme 2

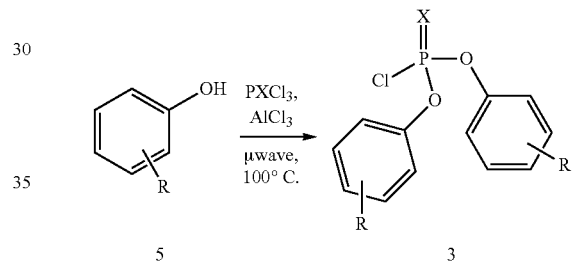

In Scheme 2, diaryl phosphorochloridates or diaryl phosphorochloridothioates 3 may be prepared by heating phenols 5 with phosphorus oxychloride or thiophosphoryl chloride in the presence of catalytic aluminum trichloride and in the absence of solvent to 100° C. in the microwave.

Synthesis of bis(2,6-dimethylphenyl)phosphorochloridate (6)

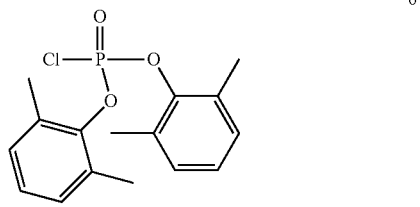

2,6-dimethylphenol (1 g, 8.18 mmol) and aluminum trichloride (109 mg, 0.818 mmol, 0.1 eq) were added to a microwave vial. Phosphorus oxychloride (0.375 mL, 4.09 mmol, 0.5 eq) was added, the vial was sealed and subsequently heated in the microwave for 1 h. Reaction progress was monitored by TLC, and the reaction was quenched before going to completion. The reaction mixture was diluted with dicholoromethane, washed with water and brine, dried over MgSO$_4$, and filtered through celite. The filtrate was concentrated under reduced pressure providing an oily residue that was taken directly to the next step without further purification.

Synthesis of bis(4-chlorophenyl)phosphorochloridate (7)

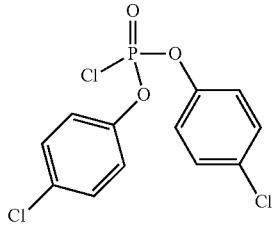

7

The title compound was prepared in similar fashion as compound 6, substituting 4-chlorophenol for 2,6-dimethylphenol. The resulting oily residue was taken to the next step without further purification.

Synthesis of bis(4-methylphenyl)phosphorochloridate (8)

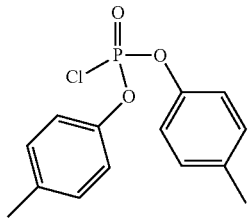

8

The title compound was prepared in similar fashion as compound 6, substituting 4-methylphenol for 2,6-dimethylphenol. The resulting oily residue was taken to the next step without further purification.

Synthesis of bis(4-isopropylphenyl)phosphorochloridate (9)

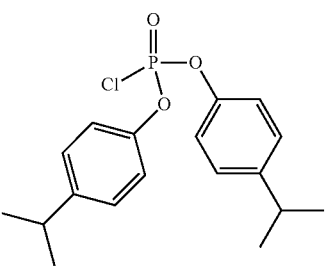

9

The title compound was prepared in similar fashion as compound 6, substituting 4-isopropylphenol for 2,6-dimethylphenol. The resulting oily residue was taken to the next step without further purification.

Synthesis of bis(2,4,6-trimethylphenyl)phosphorochloridate (10)

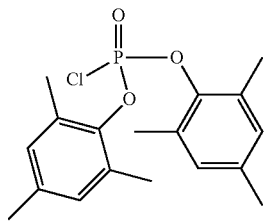

10

The title compound was prepared in similar fashion as compound 6, substituting 2,4,6-trimethylphenol for 2,6-dimethylphenol. The resulting oily residue was taken to the next step without further purification.

Synthesis of Biphenyl Phosphorochloridate (11)

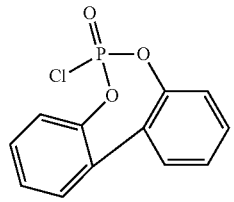

11

Biphenol (1 g, 5.37 mmol), pyridine (0.434 mg, 5.37 mmol, 1.0 eq) and benzene (20 mL) were added to a round bottom flask. Phosphorus oxychloride (0.492 mL, 5.37 mmol, 1.0 eq) was added, and the reaction mixture was refluxed for 2 h. Reaction progress was monitored by TLC. Upon completion, the reaction mixture was filtered through celite. The filtrate was concentrated under reduced pressure providing an oily residue that was taken directly to the next step without further purification.

Synthesis of Biphenyl Phosphorochloridothioate (12)

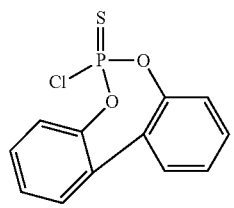

12

The title compound was prepared in similar fashion as compound II, substituting thiophosphoryl chloride for phos-

Synthesis of O,O-diphenyl phosphorochloridothioate (13)

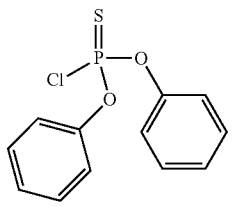

13

The title compound was prepared in similar fashion as compound 6, substituting phenol for 2,6-dimethylphenol and thiophosphoryl chloride for phosphorus oxychloride. The resulting oily residue was taken to the next step without further purification.

Synthesis of BTM-isobu-OP(O)(OPh-2,6-dimethyl)₂ (14)

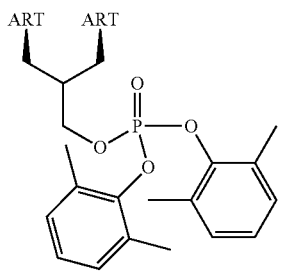

14

Primary alcohol 2 (20 mg, 0.033 mmol) was dissolved in dichloromethane (2 mL) under argon at room temperature. To the stirring solution were added pyridine (0.013 mL, 0.165 mmol, 5.0 eq), and bis(2,6-dimethylphenyl)phosphorochloridate 6 (53.5 mg, 0.165 mmol, 5.0 eq) in that order. The reaction mixture was allowed to stir at rt for 3 hr, at which point the reaction was deemed complete by TLC. The reaction mixture was diluted with dicholoromethane and washed consecutively with 10% citric acid and brine. The organic layer was dried over MgSO₄, filtered, and concentrated in vacuo. The residue was purified directly on silica gel. Gradient elution (10-40% ethyl acetate in hexanes) afforded BTM-isobu-OP(O)(OPh-2,6-dimethyl)₂ 14 (MW=895) as a colorless, amorphous solid: (18 mg, 0.02 mmol, 61%); ¹H NMR (400 MHz, CDCl₃) δ 7.07-6.91 (m, 6H), 5.29 (s, 1H), 5.25 (s, 1H), 4.53-4.44 (m, 1H), 4.42-4.30 (m, 2H), 4.19-4.11 (m, 1H), 2.72-2.62 (m, 1H), 2.56-2.46 (m, 1H), 2.34 (s, 6H), 2.32 (s, 6H), 2.29-2.18 (m, 2H), 2.02-1.93 (m, 2H), 1.92-1.79 (m, 5H), 1.72 (d, J=15.54 Hz, 4H), 1.66-1.49 (m, 6H), 1.36 (d, J=8.46 Hz, 8H), 1.34-1.16 (m, 8H), 0.94 (d, J=6.00 Hz, 3H), 0.88 (d, J=4.67 Hz, 3H), 0.79 (t, J=6.41 Hz, 4H); ¹³C NMR (100 MHz, CDCl₃) δ 157.7, 148.5, 148.4, 130.4, 129.0, 125.1, 103.2, 102.8, 89.4, 88.6, 81.2, 81.1, 74.0, 72.1, 72.0, 70.9, 52.5, 52.2, 44.6, 44.2, 37.5, 37.3, 36.7, 36.6, 35.4, 35.4 34.6, 34.5, 30.5, 30.4, 30.2, 29.2, 26.1, 26.1, 24.9, 24.7, 20.2, 20.1, 17.2, 13.3, 12.7; ESI-HRMS m/z (M+Na)⁺ calc.= 917.4594, found=917.4589; [α]$_D^{25}$ +60.33 (c=0.69, CHCl₃); FT-IR (cm⁻¹) 2937, 2925, 1585, 1471, 1376, 1281, 1159, 1092, 1009, 953, 878, 753.

Synthesis of BTM-isobu-OP(O)(OPh-4-Cl)₂ (15)

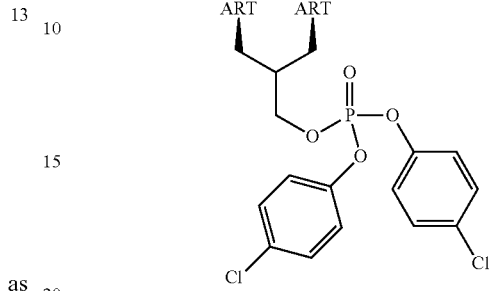

15

The title compound was prepared in similar fashion as compound 14, substituting bis(4-chlorophenyl)phosphorochloridate 7 for bis(2,6-dimethylphenyl) phosphorochloridate 6. Gradient elution (10-40% ethyl acetate in hexanes) afforded BTM-isobu-OP(O)(OPh-4-Cl)₂ 15 (MW=907) as a colorless, amorphous solid: (21.3 mg, 0.023 mmol, 71%); ¹H NMR (400 MHz, CDCl₃) δ 7.28 (d, J=8.65 Hz, 4H), 7.15-7.21 (m, 4H), 5.28 (s, 1H), 5.25 (s, 1H), 4.45-4.54 (m, 2H), 4.41 (dd, J=9.28, 6.76 Hz, 1H), 4.26 (dd, J=9.38, 6.54 Hz, 1H), 2.57-2.71 (m, 1H), 2.39-2.51 (m, 2H), 2.29 (t, J=13.80 Hz, 4H), 1.96-2.04 (m, 2H), 1.82-1.94 (m, 2H), 1.70-1.80 (m, 4H), 1.55-1.68 (m, 4H), 1.39-1.50 (m, 4H), 1.36 (d, J=10.74 Hz, 6H), 1.16-1.31 (m, 8H), 0.93 (dd, J=9.54, 4.93 Hz, 6H), 0.80 (t, J=8.27 Hz, 4H); ¹³C NMR (100 MHz, CDCl₃) δ 149.2, 149.1, 130.7, 129.8, 121.6, 121.5, 121.5, 103.1, 102.8, 89.7, 89.0, 81.2, 77.4, 77.1, 76.8, 73.5, 72.3, 72.2, 70.2, 52.3, 52.1, 44.4, 44.0, 37.5, 37.4, 36.7, 36.6, 35.4, 35.4, 34.5, 34.4, 30.6, 30.5, 30.3, 29.7, 26.1, 26.1, 24.9, 24.9, 24.8, 24.7, 20.2, 20.1, 13.0, 12.5; ESI-HRMS m/z (M+Na)⁺ calc.=929.3188, found=929.3186; [α]$_D^{25}$ +60.09 (c=0.27, CHCl₃); FT-IR (cm⁻¹) 2923, 2918, 1580, 1486, 1375, 1301, 1197, 1092, 1009, 949, 878, 834, 754.

Synthesis of BTM-isobu-OP(O) (OPh-4-Me)₂ (16)

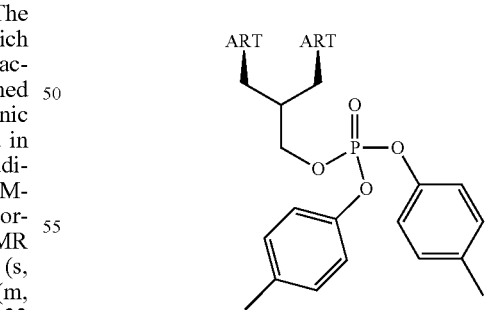

16

The title compound was prepared in similar fashion as compound 14, substituting bis(4-methylphenyl)phosphorochloridate 8 for bis(2,6-dimethylphenyl) phosphorochloridate 6. Gradient elution (10-40% ethyl acetate in hexanes) afforded BTM-isobu-OP(O)(OPh-4-Me)₂ 16 as a colorless, amorphous solid: (6.2 mg, 0.007 mmol, 36%), ¹H NMR (400 MHz, CDCl₃) δ 7.10-7.00 (m, 8H), 5.29 (s, 1H), 5.27 (s, 1H), 4.52-4.47 (m, 1H), 4.43-4.39 (m, 2H), 4.24-4.20 (m, 1H), 2.71-2.65 (m, 1H), 2.57-2.48 (m, 1H), 2.38-2.24 (m, 10H, including singlet at 2.30), 2.04-1.98 (m, 4H) 1.93-1.82 (m, 4H), 1.78-1.70 (m, 2H), 1.68-1.54 (m, 4H), 1.49-1.35 (m, 9H, including singlets at 1.39 and 1.36), 1.31-1.22 (m, 6H), 1.00-0.92 (m, 6H), 0.85-0.80 (m, 6H); $^{13}$C NMR (100 MHz, CDCl$_3$) δ 149.2, 149.1, 130.7, 129.8, 121.6, 121.5, 121.5, 103.1, 102.8, 89.7, 89.0, 81.2, 77.4, 77.1, 76.8, 73.5, 72.3, 70.2, 52.3, 44.2, 44.1, 37.5, 37.4, 36.7, 36.6, 35.4, 35.4, 34.5, 34.4, 30.6, 30.5, 29.9, 29.7, 26.1, 26.1, 25.2, 24.9, 24.8, 24.3, 20.1, 13.0, 12.5; FAB-HRMS m/z (M+H)$^+$ calcd=867.4448, found=867.4418; [α]$_D^{23}$=44 (c=0.41, CHCl$_3$); FT-IR (cm$^{-1}$) 2930, 2928, 1560, 1475, 1375, 1301, 1165, 1092, 1009, 949, 878, 834, 754.

Synthesis of BTM-isobu-OP(O)(OPh-4-iPr)$_2$ (17)

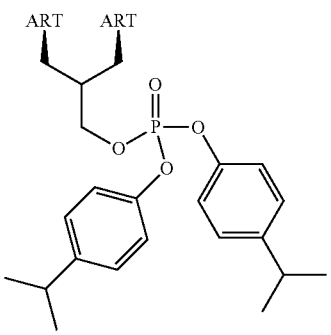

The title compound was prepared in similar fashion as compound 14, substituting bis(4-isopropylphenyl)phosphorochloridate 9 for bis(2,6-dimethylphenyl)phosphorochloridate 6. Gradient elution (10-40% ethyl acetate in hexanes) afforded BTM-isobu-OP(O)(OPh-4-iPr)$_2$ 17 as a colorless, amorphous solid: yield (8.6 mg, 0.009 mmol, 56%), $^1$H NMR (400 MHz, CDCl$_3$) δ 7.16-7.09 (m, 8H), 5.33 (s, 1H), 5.28 (s, 1H), 4.56-4.99 (m, 1H), 4.84-4.37 (m, 2H), 4.27-4.20 (m, 1H), 2.91-2.83 (m, 2H), 2.71-2.64 (m, 1H), 2.54-2.48 (m, 1H), 2.33-2.26 (m, 3H), 2.03-1.95 (m, 2H), 1.92-1.81 (m, 4H), 1.78-1.70 (m, 4H), 1.68-1.55 (m, 4H), 1.54-1.43 (m, 4H), 1.42-1.35 (m, 9H), 1.29-1.20 (m, 15H), 0.99-0.89 (m, 6H), 0.85-0.78 (m, 6H); $^{13}$C NMR (100 MHz, CDCl$_3$) δ 149.2, 149.1, 130.7, 129.8, 121.6, 121.5, 121.5, 103.1, 102.8, 89.7, 89.0, 81.2, 77.4, 77.1, 76.8, 73.5, 72.3, 72.2, 70.2, 52.3, 52.1, 52.1, 44.4, 37.5, 37.4, 36.7, 36.6, 35.4, 34.5, 34.4, 30.9, 30.3, 29.7, 26.3, 26.1, 24.9, 24.9, 24.8, 24.7, 20.2, 20.1, 13.0, 12.5; ESI-HRMS (M+H)$^+$ calcd=923.5074, found=923.5036; [α]$_D^{23}$=57 (c=0.14, CHCl$_3$); FT-IR (cm$^{-1}$) 2923, 2918, 1580, 1486, 1375, 1301, 1197, 1092, 1009, 949, 878, 834, 754.

Synthesis of BTM-isobu-OP(O) (OPh-2,4,6-triMe)$_2$ (18)

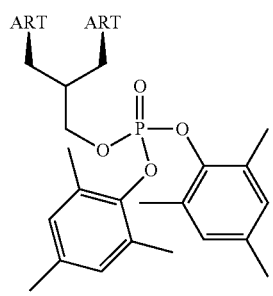

The title compound was prepared in similar fashion as compound 14, substituting bis(2,4,6-trimethylphenyl)phosphorochloridate 10 for bis(2,6-dimethylphenyl)phosphorochloridate 6. Gradient elution (10-40% ethyl acetate in hexanes) afforded BTM-isobu-OP(O)(OPh-4-iPr)$_2$ 18 as a colorless, amorphous solid: (12 mg, 0.013 mmol, 27%); $^1$H NMR (400 MHz, CDCl$_3$) δ 6.85-6.74 (m, 4H), 5.28 (s, 1H), 5.24 (s, 1H), 4.44 (ddd, J=10.14, 5.31, 5.15 Hz, 1H), 4.39-4.27 (m, 2H), 4.19-4.05 (m, 1H), 2.74-2.60 (m, 1H), 2.57-2.44 (m, 1H), 2.36-2.24 (m, 16H), 2.21 (s, 6H), 2.07-1.94 (m, 2H), 1.92-1.79 (m, 2H), 1.77-1.68 (m, 2H), 1.66-1.49 (m, 6H), 1.41-1.33 (m, 9H), 1.33-1.17 (m, 10H), 0.94 (d, J=6.00 Hz, 3H), 0.88 (d, J=5.24 Hz, 3H), 0.81-0.74 (m, 4H); $^{13}$C NMR (100 MHz, CDCl$_3$) δ 134.4, 129.9, 129.9, 129.6, 129.5, 103.3, 102.8, 89.3, 88.5, 81.2, 81.1, 74.1, 71.0, 52.5, 52.2, 44.6, 44.2, 37.4, 37.3, 34.5, 30.4, 26.1, 26.0, 24.8, 20.6, 20.2, 20.1, 17.1; ESI-HRMS m/z for (M+Na)$^+$ calcd=945.4920, found=945.4914; [α]$_D^{23}$=58.32 (c=0.635, CHCl$_3$); FT-IR (cm$^{-1}$) 2930, 2924, 2915, 1582, 1481, 1376, 1279, 1189, 1130, 1009, 965, 941, 878, 852, 752.

Synthesis of BTM-isobu-OP(O) (O,O-biphenyl) (19)

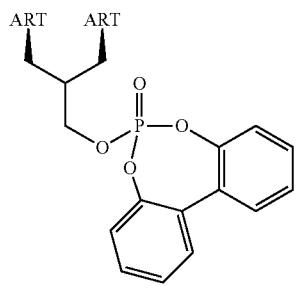

The title compound was prepared in similar fashion as compound 14, substituting biphenyl phosphorochloridate 11 for bis(2,6-dimethylphenyl) phosphorochloridate 6. Gradient elution (10-40% ethyl acetate in hexanes) afforded BTM-isobu-OP(O)(O,O-biphenyl) 19 as a colorless, amorphous solid: (7.0 mg, 0.008 mmol, 34%), $^1$H NMR (400 MHz, CDCl$_3$) δ 7.55-7.26 (m, 8H), 5.29 (s, 1H), 5.28 (s, 1H), 4.62-4.46 (m, 2H), 4.39-4.35 (m, 1H), 4.24-4.19 (m, 1H), 2.73-2.65 (m, 1H), 2.60-2.52 (m, 1H), 2.37-2.26 (m, 3H), 2.08-1.97 (m, 2H), 1.92-1.80 (m, 3H), 1.79-1.70 (m, 2H), 1.68-1.55 (m, 5H), 1.50-1.35 (m, 12H, including singlets at 1.40 and 1.36), 1.31-1.27 (m, 6H), 1.00-0.92 (m, 6H), 0.89-0.80 (m, 6H); $^{13}$C NMR (100 MHz, CDCl$_3$) δ 134.4, 129.9, 129.6, 129.5, 105.3, 102.8, 89.3, 88.5, 81.2, 81.1, 74.1, 72.0, 52.5, 52.2, 43.6, 43.4, 37.4, 37.3, 34.5, 31.0, 26.1, 26.0, 24.8, 20.6, 20.2, 20.1, 17.1, 13.5; ESI-HRMS (M+Na)$^+$ calcd=859.3822, found=859.3814; [α]$_D^{23}$=73 (c=0.42, CHCl$_3$); FT-IR (cm$^{-1}$) 2930, 2927, 1582, 1489, 1376, 1175, 1130, 1009, 965, 941, 878, 852, 752.

Synthesis of BTM-isobu-OP(S)(O, O-biphenyl) (20)

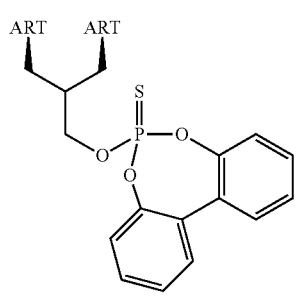

The title compound was prepared in similar fashion as compound 14, substituting biphenyl phosphorochloridothioate 12 for bis(2,6-dimethylphenyl) phosphorochloridate 6. Gradient elution (10-40% ethyl acetate in hexanes) afforded BTM-isobu-OP(S)(O,O-biphenyl) 20 as a colorless, amorphous solid: yield (5.5 mg, 0.006 mmol, 26%), $^1$H NMR (400 MHz, CDCl$_3$) δ 7.54-7.31 (m, 8H), 5.30 (s, 1H), 5.28 (s, 1H), 4.57-4.54 (m, 2H), 4.41-4.38 (m, 1H), 4.24-4.20 (m, 1H), 2.71-2.65 (m, 1H), 2.59-2.51 (m, 1H), 2.37-2.28 (m, 2H), 2.07-1.98 (m, 4H), 1.96-1.81 (m, 4H), 1.79-1.60 (m, 4H), 1.60-1.42 (m, 12H, including singlets at 1.40 and 1.39), 1.35-1.24 (m, 6H), 1.00-0.92 (m, 6H), 0.88-0.80 (m, 6H); $^{13}$C NMR (100 MHz, CDCl$_3$) δ 134.4, 131.6, 131.9, 129.6, 103.3, 102.8, 89.3, 81.2, 81.1, 73.1, 71.0, 55.5, 52.2, 44.6, 44.2, 38.4, 37.4, 34.5, 30.4, 26.1, 26.0, 24.8, 20.6, 20.2, 17.1; ESI-HRMS (M+Na)$^+$ calcd=853.3760, found=853.3747; $[α]_D^{23}$=124 (c=0.40, CHCl$_3$); FT-IR (cm$^{-1}$) 2930, 2924, 2915, 1582, 1481, 1376, 1279, 1189, 1130, 1009, 965, 941, 878, 852, 752.

Synthesis of BTM-isobu-OP(S)(OPh)$_2$ (21)

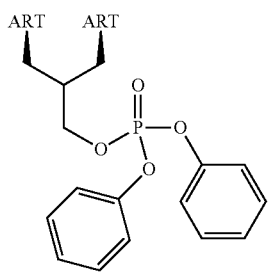

21

The title compound was prepared in similar fashion as compound 14, substituting O,O-diphenyl phosphorochloridothioate 13 for bis(2,6-dimethylphenyl) phosphorochloridate 6. Gradient elution (10-40% ethyl acetate in hexanes) afforded BTM-isobu-OP(S)(OPh)$_2$ 21 as a colorless, amorphous solid: yield (7.5 mg, 0.009 mmol, 27%), $^1$H NMR (400 MHz, CDCl$_3$) δ 7.36-7.17 (m, 12H), 5.33 (s, 1H), 5.30 (s, 1H), 4.55-4.37 (m, 3H), 4.27-4.24 (m, 1H), 2.73-2.65 (m, 1H), 2.59-2.52 (m, 1H), 2.37-2.28 (m, 3H), 2.04-1.98 (m, 3H), 1.94-1.82 (m, 3H), 1.79-1.63 (m, 6H), 1.52-1.35 (m, 12H, including singlets at 1.40 and 1.38), 1.31-1.23 (m, 4H), 1.00-0.82 (m, 12H); $^{13}$C NMR (100 MHz, CDCl$_3$) δ 150.7, 129.7, 125.1, 120.2, 120.1, 103.1, 102.4, 89.9, 89.0, 81.2, 81.0, 74.2, 72.1, 70.8, 52.4, 52.1, 44.5, 44.2, 38.8, 38.0, 36.6, 36.5, 35.0, 34.5, 30.0, 30.0, 29.9, 29.4, 26.1, 25.9, 24.9, 24.9, 24.7, 20.2, 20.1, 13.2, 12.6; ESI-HRMS (M+Na)$^+$ calcd=877.3741, found=877.3741; $[α]_D^{23}$=62 (c=0.39, CHCl$_3$); FT-IR (cm$^{-1}$) 2919, 2861, 1589, 1485, 1455, 1376, 1290, 1225, 1194, 1110, 1009, 943, 760.

Scheme 3

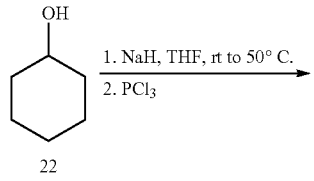

22

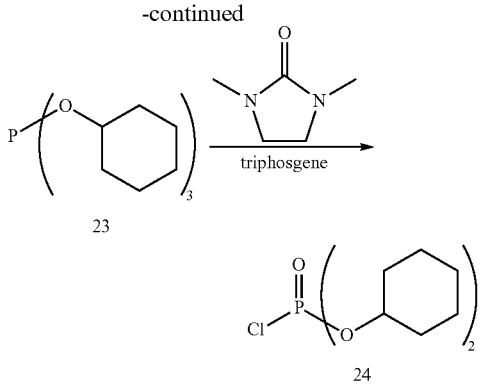

Synthesis of Tricyclohexyl Phosphite (23)

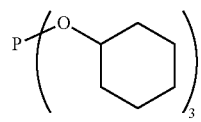

23

Cyclohexanol (22, 2.26 g, 22.57 mmol, 3.1 eq) and THF (40 mL) were added to a round bottom flask. Sodium hydride (NaH, 542 mg, 22.57 mmol, 3.1 eq) was added and the reaction mixture was heated to 50° C. for 3 h. The heat was turned off, allowing the reaction to slowly cool to rt, and the reaction mixture was stirred at rt overnight. The reaction was deemed complete by TLC, and the solvent was removed under reduced pressure and the residue was dissolved in hexanes (50 mL). The solution was filtered through celite and the solvent was again removed under reduced pressure. The resulting crude oil was taken on to the next step without further purification.

Synthesis of Dicyclohexyl Phosphorochloridate (24)

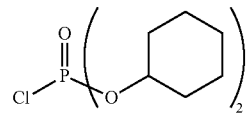

24

Tricyclohexyl phosphite 23 (2.3 g, 7.0 mmol, 1.0 eq) and 1,3-dimethylimidazolidin-2-one (24 mg, 0.21 mmol, 0.13 eq) and dichloromethane (30 mL) were added to a round bottom flask, and the stirring solution was cooled to 0° C. in an ice bath. A separate solution of triphosgene (706 mg, 2.38 mmol, 0.34 eq) in dichloromethane (5 mL) was prepared and added dropwise to the original stirring solution over 10 mins. The reaction mixture was stirred at 0° C. for 30 mins, the ice bath was removed, and the mixture was heated to 35° C. for 3 h. The reaction was deemed complete by TLC, and the solvent was removed under reduced pressure. The residue was distilled in a Buchi Kugelrohr, affording a colorless oil: (1.68 g, 5.98 mmol, 85%).

Synthesis of BTM-isobu-OP(O)(O—C$_6$H$_{11}$)$_2$ (25)

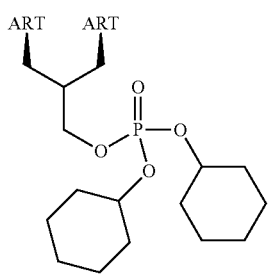

25

The title compound was prepared in similar fashion as compound 14, substituting dicyclohexyl phosphorochloridate 24 for bis(2,6-dimethylphenyl) phosphorochloridate 6. Gradient elution (10-40% ethyl acetate in hexanes) afforded BTM-isobu-OP(O)(O—C$_6$H$_{11}$)$_2$ 25 as a colorless, amorphous solid: (7.1 mg, 0.008 mmol, 25%); $^1$H NMR (400 MHz, CDCl$_3$) δ 5.30 (s, 2H), 4.63-4.53 (m, 1H), 4.50-4.34 (m, 2H), 4.30 (d, J=4.86 Hz, 2H), 4.24 (dd, J=9.76, 6.16 Hz, 1H), 2.74-2.64 (m, 1H), 2.63-2.54 (m, 1H), 2.38-2.25 (m, 2H), 2.25-2.18 (m, 1H), 2.04-1.97 (m, 3H), 1.95-1.85 (m, 7H), 1.82-1.69 (m, 8H), 1.68-1.59 (m, 6H), 1.58-1.47 (m, 6H), 1.47-1.38 (m, 10H), 1.37-1.29 (m, 6H), 1.28-1.19 (m, 6H), 0.95 (d, J=6.06 Hz, 6H), 0.85 (t, J=7.14 Hz, 4H); $^{13}$C NMR (100 MHz, CDCl$_3$) δ 154.8, 103.2, 102.9, 89.37, 81.1, 81.1, 73.8, 71.4, 52.5, 52.2, 44.6, 44.2, 37.4, 36.6, 34.5, 34.4, 31.6, 30.6, 30.3, 29.7, 26.1, 25.3, 25.0, 24.7, 23.8, 23.6, 20.2, 13.2, 12.8; ESI-HRMS m/z for (M+Na)$^+$ calcd=873.4894, found=873.4890; [α]$_D^{23}$=49.95 (c=0.355, CHCl$_3$); FT-IR (cm$^{-1}$) 2936, 2925, 1737, 1451, 1376, 1254, 1105, 1038, 1008, 963, 880.

Scheme 4

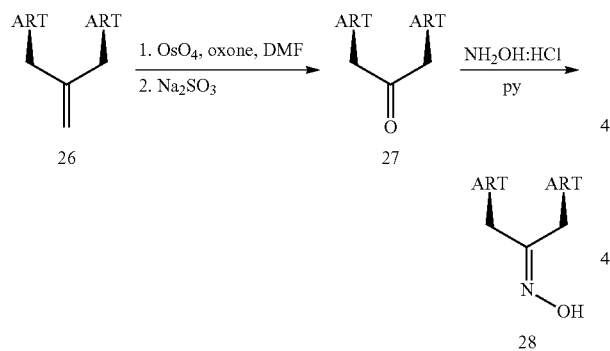

In Scheme 4, dimer oxime 28 is prepared in two steps from isobutylene dimer 26 via dimer ketone 27, which can be prepared according to the procedure described in *J. Med. Chem*, 2003, 46, 1060-1065.

Synthesis of Dimer Oxime (28)

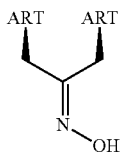

28

Dimer ketone 27 (110 mg, 0.186 mmol, 1.0 eq), hydroxylamine hydrochloride (64.7 mg, 0.931 mmol, 5.0 eq) and pyridine (5 mL) were added to a round bottom flask. The reaction mixture was stirred at rt for 1 h, at which point the reaction was deemed complete by TLC. The reaction mixture was diluted with dichloromethane and washed with 10% aq. citric acid. The organic layer was dried over MgSO$_4$, filtered, and the solvent was removed under reduced pressure. The residue was purified directly on silica. Gradient elution (30-50% ethyl acetate in hexanes) afforded dimer oxime 28 as a colorless, amorphous solid: yield (94 mg, 0.155 mmol, 84%); $^1$H NMR (400 MHz, CDCl$_3$) δ 8.53 (bs, 1H), 5.49 (s, 1H), 5.43 (s, 1H), 4.29-4.16 (m, 2H), 3.00-2.87 (m, 2H), 2.85-2.71 (m, 6H), 2.41-2.25 (m, 4H), 2.04-1.92 (m, 4H), 1.88-1.74 (m, 5H), 1.61 (m, 4H), 1.55-1.41 (m, 4H), 1.40-1.30 (m, 6H), 1.26-1.15 (m, 2H), 0.96-0.84 (m, 9H).

Scheme 5

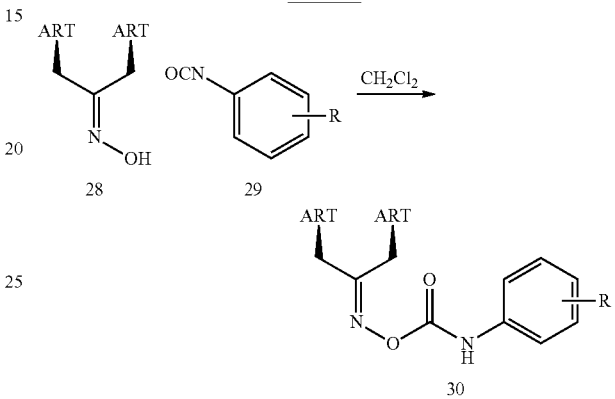

Dimer oxime 28 can be reacted with various isocyanates of general structure 29, providing O-arylcarbamoyl oxime dimers of general structure 30 (Scheme 5).

Synthesis of BTM-isobu-C=NOC(O)NHPh (31)

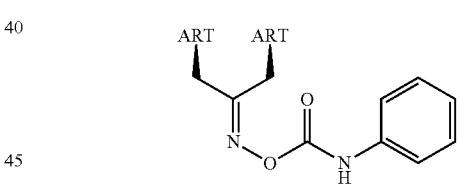

31

To a round bottom flask were added dimer oxime 28 (20 mg, 0.04 mmol, 1.0 eq), phenyl isocyanate (8 mg, 0.066 mmol, 2.0 eq) and dichloromethane (2 mL). The reaction mixture was allowed to stir for 2 h. Upon completion by TLC, the reaction mixture was concentrated under reduced pressure, and the residue was purified directly on silica. Gradient elution (10-50% ethyl acetate in hexanes) afforded BTM-isobu-C=NOC(O)NHPh 31 as a colorless, amorphous solid: (17 mg, 0.023 mmol, 71%); $^1$H NMR (400 MHz, CDCl$_3$) δ 8.32 (brs, 1H), 7.50 (d, J=8.40 Hz, 2H), 7.33 (t, J=7.74 Hz, 2H), 7.10 (t, J=7.39 Hz, 1H), 5.44 (s, 1H), 5.43 (s, 1H), 4.59-4.51 (m, 1H), 4.41 (ddd, J=11.65, 5.75, 1.55 Hz, 1H), 3.24 (t, J=12.63 Hz, 1 H), 2.92-2.69 (m, 4H), 2.61 (dd, J=14.84, 2.15 Hz, 1H), 2.34 (td, J=13.96, 3.73 Hz, 2H), 2.06-1.97 (m, 2H), 1.96-1.79 (m, 4H), 1.71-1.64 (m, 4H), 1.60 (dt, J=13.82, 4.78 Hz, 2H), 1.51-1.40 (m, 6H), 1.39-1.32 (m, 12H), 1.31-1.20 (m, 4H), 1.00-0.92 (m, 6H); $^{13}$C NMR (100 MHz, CDCl$_3$) δ 166.2, 152.2, 137.3, 129.0, 124.0, 119.7, 103.5, 103.2, 89.1, 88.7, 81.1, 81.1, 73.8, 72.3, 52.5, 52.2, 44.4, 44.0, 37.3, 37.1, 36.6, 36.6, 34.5, 34.4, 34.2, 30.6, 30.5, 28.5, 26.2, 26.0, 24.7, 24.7, 24.6, 24.6, 20.3, 20.1, 13.4, 13.0; ESI-HRMS m/z for (M+H)$^+$ calcd=724.3947, found=724.4004; $[\alpha]_D^{23}$=69.22 (c=0.58, CHCl$_3$); FT-IR (cm$^{-1}$) 2939, 2930, 2922, 1747, 1684, 1670, 1521, 1489, 1473, 1457, 1091, 1053, 1009, 877, 753.

Synthesis of BTM-isobu-C=NOC(O)NHPh-3-Cl (32)

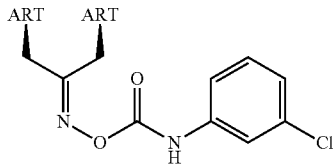

32

The title compound was prepared in similar fashion as compound 31, substituting 3-chlorophenyl isocyanate for phenyl isocyante. Gradient elution (10-50% ethyl acetate in hexanes) afforded BTM-isobu-C=NOC(O)NHPh-3-Cl 32 as a colorless, amorphous solid: (17 mg, 0.022 mmol, 68%); $^1$H NMR (400 MHz, CDCl$_3$) δ 8.39 (s, 1H), 7.59 (s, 1H), 7.41 (d, J=8.15 Hz, 1H), 7.25-7.20 (m, 1H), 7.07 (d, J=7.96 Hz, 1H), 5.42 (s, 2H), 4.62-4.51 (m, 1H), 4.42 (dd, J=10.29, 5.43 Hz, 1H), 3.29-3.18 (m, 1H), 2.89-2.78 (m, 2H), 2.78-2.67 (m, 2H), 2.67-2.57 (m, 1H), 2.33 (td, J=13.96, 3.73 Hz, 4H), 2.04-1.97 (m, 4H), 1.96-1.79 (m, 3H), 1.72-1.56 (m, 6H), 1.48-1.39 (m, 4H), 1.39-1.33 (m, 6H), 1.32-1.21 (m, 4H), 0.99-0.93 (m, 9H); $^{13}$C NMR (100 MHz, CDCl$_3$) δ 166.4, 151.9, 138.6, 134.6, 130.0, 124.0, 119.7, 117.6, 103.5, 103.2, 89.2, 88.8, 81.1, 81.1, 73.4, 71.9, 60.4, 52.4, 52.1, 44.3, 44.0, 37.3, 37.1, 36.6, 34.5, 34.4, 34.1, 30.5, 30.4, 28.7, 26.1, 26.0, 24.8, 24.7, 24.6, 24.6, 20.3, 20.1, 14.2, 13.4, 13.0; ESI-HRMS m/z for (M+H)$^+$ calcd=759.3641, found=759.3642; $[\alpha]_D^{23}$=52.44 (c=0.89, CHCl$_3$); FT-IR (cm$^{-1}$) 2940, 2938, 2925, 1771, 1597, 1510, 1440, 1375, 1198, 1173, 1097, 1053, 1012, 940, 876, 752.

Synthesis of BTM-isobu-C=NOP(O)(OPh)$_2$ (33)

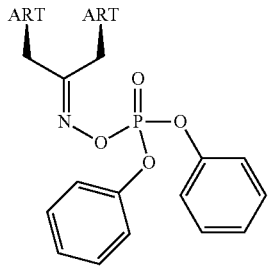

33

The title compound was prepared in similar fashion as compound 14, substituting diphenyl phosphorochloridate for bis(2,6-dimethylphenyl) phosphorochloridate 6 and dimer oxime 28 for primary alcohol 2. Gradient elution (10-40% ethyl acetate in hexanes) afforded BTM-isobu-C=NOP(O)(OPh)$_2$ 33 as a colorless, amorphous solid: (16 mg, 0.019 mmol, 77%); $^1$H NMR (400 MHz, CDCl$_3$) δ7.41-7.26 (m, 8H), 7.23-7.14 (m, 2H), 5.45 (s, 1H), 5.43 (s, 1H), 4.33-4.14 (m, 2H), 3.09-2.91 (m, 2H), 2.89-2.71 (m, 3H), 2.58 (d, J=14.27 Hz, 1H), 2.45-2.27 (m, 2H), 2.00 (dd, J=14.06, 3.51 Hz, 2H), 1.92-1.74 (m, 4H), 1.71-1.52 (m, 5H), 1.50-1.33 (m, 12H), 1.33-1.18 (m, 4H), 0.97-0.89 (m, 9H), 0.80 (d, J=7.49 Hz, 2H); $^{13}$C NMR (100 MHz, CDCl$_3$) δ 129.7, 129.7, 125.3, 120.5, 120.4, 103.6, 103.6, 88.1, 88.0, 81.0, 81.0, 75.1, 75.0, 52.5, 52.5, 44.5, 37.0, 36.8, 36.7, 34.4, 30.6, 30.6, 27.4, 26.2, 24.6, 20.3, 20.2, 13.5, 13.4; ESI-HRMS m/z for (M+Na)$^+$ calcd=860. 3760, found=860.3754; $[\alpha]_D^{23}$=99.57 (c=0.37, CHCl$_3$); FT-IR (cm$^{-1}$) 2361, 2340, 1698, 1683, 1590, 1489, 1376, 1298, 1189, 1091, 1054, 1009, 958, 824, 753.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Weller T H. The cytomegaloviruses: ubiquitous agents with protean clinical manifestations. II. *N Engl J Med.* 1971; 285:267-274.

Weller T H. The cytomegaloviruses: ubiquitous agents with protean clinical manifestations. I. *N Engl J Med.* 1971; 285:203-214.

Griffiths P D, Clark D A, Emery V C. Betaherpesviruses in transplant recipients. *J Antimicrob Chemother.* 2000; 45(Suppl T3):29-34.

Kovacs A, Schluchter M, Easley K, Demmler G, Shearer W, et al. Cytomegalovirus infection and HIV-1 disease progression in infants born to HIV-1-infected women. Pediatric Pulmonary and Cardiovascular Complications of Vertically Transmitted HIV Infection Study Group. *N Engl J Med.* 1999; 341:77-84.

Demmler G J. Infectious Diseases Society of America and Centers for Disease Control. Summary of a workshop on surveillance for congenital cytomegalovirus disease. *Rev Infect Dis.* 1991; 13:315-329.

Osawa R, Singh N. Cytomegalovirus infection in critically ill patients: a systematic review. *Crit Care.* 2009; 13:R68.

Limaye A P, Kirby K A, Rubenfeld G D, Leisenring W M, Bulger E M, et al. Cytomegalovirus reactivation in critically ill immunocompetent patients. *JAMA.* 2008; 300: 413-422.

Cheng J, Ke Q, Jin Z, Wang H, Kocher O, et al. Cytomegalovirus infection causes an increase of arterial blood pressure. *PLoS Pathog.* 2009; 5:e1000427.

Mitchell D A, Xie W, Schmittling R, Learn C, Friedman A, et al. Sensitive detection of human cytomegalovirus in tumors and peripheral blood of patients diagnosed with glioblastoma. *Neuro Oncol.* 2008; 10:10-18.

Matthews T, Boehme R. Antiviral activity and mechanism of action of ganciclovir. *Rev Infect Dis.* 1988; 10(Suppl 3):S490-S494.

Chrisp P, Clissold S P. Foscarnet. A review of its antiviral activity, pharmacokinetic properties and therapeutic use in immunocompromised patients with cytomegalovirus retinitis. *Drugs.* 1991; 41:104-129.

Neyts J, Snoeck R, Schols D, Balzarini J, De C E. Selective inhibition of human cytomegalovirus DNA synthesis by (S)-1-(3-hydroxy-2-phosphonylmethoxypropyl)cytosine [(S)-HPMPC] and 9-(1,3-dihydroxy-2-propoxymethyl) guanine (DHPG). *Virology.* 1990; 179:41-50.

Schreiber A, Harter G, Schubert A, Bunjes D, Mertens T, et al. Antiviral treatment of cytomegalovirus infection and resistant strains. *Expert Opin Pharmacother.* 2009; 10:191-209.

Biron K K. Antiviral drugs for cytomegalovirus diseases. *Antiviral Res.* 2006; 71:154-163.

Chou S. Antiviral drug resistance in human cytomegalovirus. *Transpl Infect Dis.* 1999; 1:105-114.

Adjuik M, Babiker A, Garner P, Olliaro P, Taylor W, et al. Artesunate combinations for treatment of malaria: meta-analysis. *Lancet.* 2004; 363:9-17.

Efferth T, Dunstan H, Sauerbrey A, Miyachi H, Chitambar C R. The anti-malarial artesunate is also active against cancer. *Int J Oncol.* 2001; 18:767-773.

Kaptein S J, Efferth T, Leis M, Rechter S, Auerochs S, et al. The anti-malaria drug artesunate inhibits replication of cytomegalovirus in vitro and in vivo. *Antiviral Res.* 2006; 69:60-69.

Efferth T, Marschall M, Wang X, Huong S M, Hauber 1, et al. Antiviral activity of artesunate towards wild-type, recombinant, and ganciclovir-resistant human cytomegaloviruses. *J Mol Med.* 2002; 80:233-242.

Posner G H, Paik I H, Sur S, McRiner A J, Borstnik K, et al. Orally active, antimalarial, anticancer, artemisinin-derived trioxane dimers with high stability and efficacy. *J Med Chem.* 2003; 46:1060-1065.

Alagbala A A, McRiner A J, Borstnik K, Labonte T, Chang W, et al. Biological mechanisms of action of novel C-10 non-acetal trioxane dimers in prostate cancer cell lines. *J Med Chem.* 2006; 49:7836-7842.

Marchini A, Liu H, Zhu H. Human cytomegalovirus with IE-2 (UL122) deleted fails to express early lytic genes. *J Virol.* 2001; 75:1870-1878.

Ahn J H, Hayward G S. Disruption of PML-associated nuclear bodies by IE1 correlates with efficient early stages of viral gene expression and DNA replication in human cytomegalovirus infection. *Virology.* 2000; 274:39-55.

Woodard L E, Chang W, Chen X, Liu J O, Shapiro T A, et al. Malaria-Infected Mice Live until at Least Day 30 after a New Monomeric Trioxane Combined with Mefloquine Are Administered Together in a Single Low Oral Dose. *J Med Chem.* 2009; 52:7458-7462.

Rosenthal A S, Chen X, Liu J O, West D C, Hergenrother P J, et al. Malaria-infected mice are cured by a single oral dose of new dimeric trioxane sulfones which are also selectively and powerfully cytotoxic to cancer cells. *J Med Chem.* 2009; 52:1198-1203.

Tanaka Y, Kanda Y, Kami M, Mori S, Hamaki T, et al. Monitoring cytomegalovirus infection by antigenemia assay and two distinct plasma real-time PCR methods after hematopoietic stem cell transplantation. *Bone Marrow Transplant.* 2002; 30:315-319.

Jones-Brando L, D'Angelo J, Posner G H, Yolken R. In vitro inhibition of *Toxoplasma gondii* by four new derivatives of artemisinin. *Antimicrob Agents Chemother.* 2006; 50:4206-4208.

Stinski M F. Sequence of protein synthesis in cells infected by human cytomegalovirus: early and late virus-induced polypeptides. *J Virol.* 1978; 26:686-701.

Sia I G, Patel R. New strategies for prevention and therapy of cytomegalovirus infection and disease in solid-organ transplant recipients. *Clin Microbiol Rev.* 2000; 13:83-121.

Yust I, Fox Z, Burke M, Johnson A, Turner D, et al. Retinal and extraocular cytomegalovirus end-organ disease in HIV-infected patients in Europe: a EuroSIDA study, 1994-2001. *Eur J Clin Microbiol Infect Dis.* 2004; 23:550-559.

Krosky P M, Baek M C, Coen D M. The human cytomegalovirus UL97 protein kinase, an antiviral drug target, is required at the stage of nuclear egress. *J Virol.* 2003; 77:905-914.

Williams S L, Hartline C B, Kushner N L, Harden E A, Bidanset D J, et al. In vitro activities of benzimidazole D- and L-ribonucleosides against herpesviruses. *Antimicrob Agents Chemother.* 2003; 47:2186-2192.

Winston D J, Young J A, Pullarkat V, Papanicolaou G A, Vij R, et al. Maribavir prophylaxis for prevention of cytomegalovirus infection in allogeneic stem cell transplant recipients: a multicenter, randomized, double-blind, placebo-controlled, dose-ranging study. *Blood.* 2008; 111:5403-5410.

Schang L M, St Vincent M R, Lacasse J J. Five years of progress on cyclin-dependent kinases and other cellular proteins as potential targets for antiviral drugs. *Antivir Chem Chemother.* 2006; 17:293-320.

Chou S, Van Wechel L C, Marousek G I. Effect of cell culture conditions on the anticytomegalovirus activity of maribavir. *Antimicrob Agents Chemother.* 2006; 50:2557-2559.

Posner G H, Ploypradith P, Parker M H, O'Dowd H, Woo S H, et al. Antimalarial, antiproliferative, and antitumor activities of artemisinin-derived, chemically robust, trioxane dimers. *J Med Chem.* 1999; 42:4275-4280.

Firestone G L, Sundar S N. Anticancer activities of artemisinin and its bioactive derivatives. *Expert Rev Mol Med.* 2009; 11:e32.

Efferth T, Romero M R, Wolf D G, Stamminger T, Marin J J, et al. The antiviral activities of artemisinin and artesunate. *Clin Infect Dis.* 2008; 47:804-811.

Shapira M Y, Resnick I B, Chou S, Neumann A U, Lurain N S, et al. Artesunate as a potent antiviral agent in a patient with late drug-resistant cytomegalovirus infection after hematopoietic stem cell transplantation. *Clin Infect Dis.* 2008; 46:1455-1457.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a cytomegalovirus infection in a subject in need of treatment thereof, the method comprising administering to the subject a therapeutically-effective amount of a compound selected from the group consisting of:

(a)

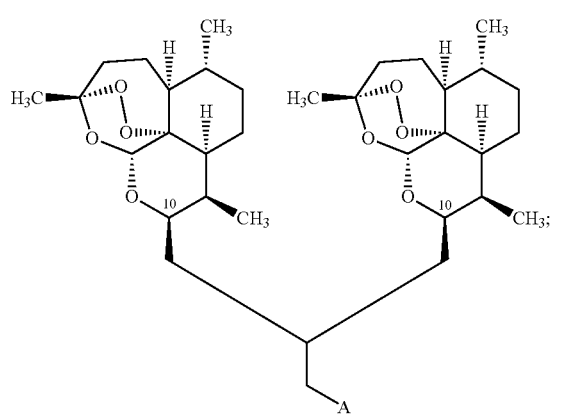

(III)

wherein:

A is —OH or S(O)$_n$—R$_1$, n is independently an integer from 0 to 2;

R$_1$ is selected from the group consisting of hydrogen, substituted or unsubstituted alkyl, substituted or unsubstituted heteroalkyl perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein R$_1$ is optionally substituted with 1 to 5 R$_2$ groups;

each R$_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$OR$_3$, —(CH$_2$)$_q$O(CH$_2$)$_t$O(CH$_2$)$_u$O(CH$_2$)$_j$OR$_3$, —(CH$_2$)$_j$C(O)R$_3$, —(CH$_2$)$_j$C(O)OR$_3$, —(CH$_2$)$_j$OC(O)R$_3$, —(CH$_2$)$_j$NR$_4$R$_5$, —(CH$_2$)$_j$C(O)NR$_4$R$_5$, —(CH$_2$)$_j$OC(O)NR$_4$R$_5$, —(CH$_2$)$_j$NR$_6$C(O)R$_3$, —(CH$_2$)$_j$NR$_6$C(O)OR$_3$, —(CH$_2$)$_j$NR$_6$C(O)NR$_4$R$_5$, —(CH$_2$)$_j$S(O)$_m$R$_7$, —(CH$_2$)$_j$S(O)$_2$NR$_4$R$_5$, —(CH$_2$)$_j$NR$_6$S(O)$_2$R$_7$, or —(CH$_2$)$_j$OP(O)(OR$_7$)$_2$, wherein q is independently an integer from 0 to 20, and j, t, and u are each independently an integer from 0 to 6, and each m is independently an integer from 0 to 2, wherein R; is optionally independently substituted with 1 to 5 R$_8$ groups;

R$_3$, R$_4$, R$_5$, R$_6$, and R$_7$ are each independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or R$_3$, R$_6$, and R$_7$ are as described above, and R$_4$ and R$_5$, together with the N atom to which they are attached, form substituted or unsubstituted heterocycloalkyl, or substituted or unsubstituted heteroaryl, wherein R$_3$, R$_4$, R$_5$, R$_6$, and R$_7$ are each optionally independently substituted with 1 to 5 R$_8$ groups; and R$_8$ is independently selected from the group consisting of halogen, hydroxyl, cyano, nitro, alkyl, perfluoroalkyl, oxo, NH$_2$, NH(alkyl), N(alkyl)$_2$, O-alkyl, S-alkyl, aryl, arylalkyl, heteroaryl, and heteroarylalkyl;

(b)

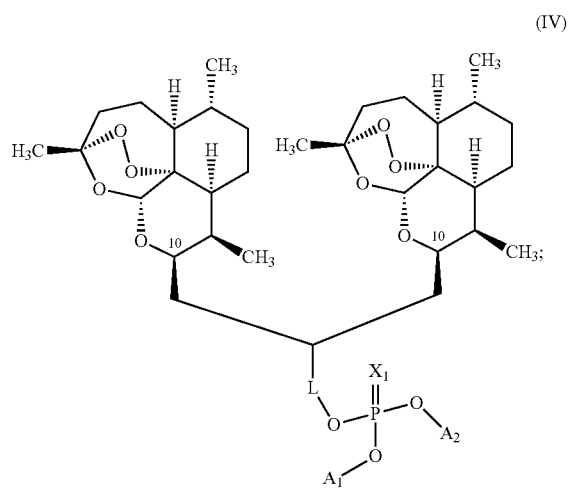

(IV)

wherein:

L is a linking group selected from (=N)— or —(CH$_2$)$_m$—, wherein m is an integer from 0 to 3;

X$_1$ is O or S;

A$_1$ and A$_2$ can be the same or different and are each independently selected from the group consisting of hydrogen, substituted or unsubstituted cycloalkyl, substituted or unsubstituted aryl, and substituted or unsubstituted heteroaryl, or A$_1$ and A$_2$ together form a substituted or unsubstituted biphenyl moiety; and (c)

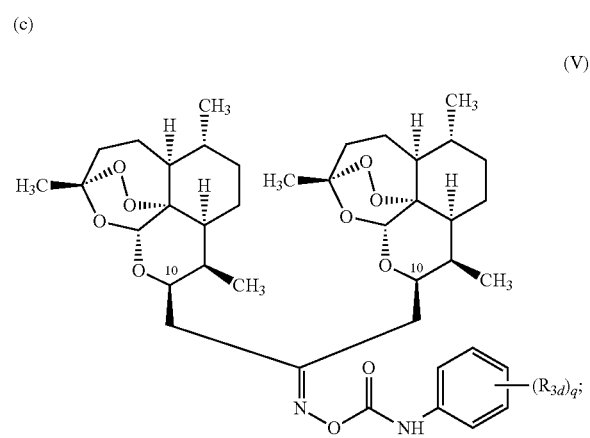

(V)

wherein:

q is an integer from 0 to 5;

each occurrence of R$_{3d}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl; or an enantiomer, diastereomer, racemate or pharmaceutically acceptable salt, prodrug, or solvate thereof.

2. The method of claim 1, wherein the compound of Formula (III) has the following structure:

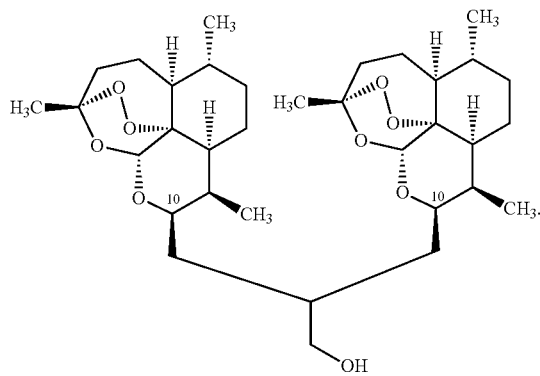

3. The method of claim 1, wherein the compound of Formula (III) has the following structure:

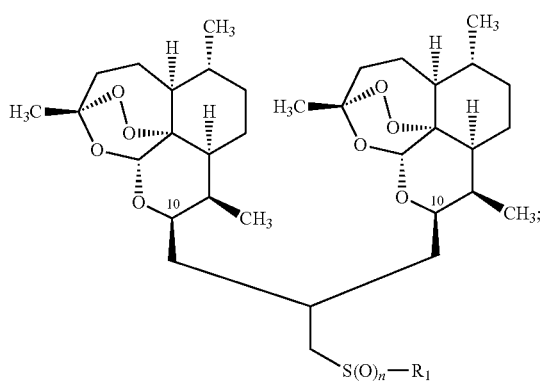

wherein:
n is independently an integer from 0 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein $R_1$ is optionally substituted with 1 to 5 $R_2$ groups;
each $R_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —$(CH_2)_jCN$, —$(CH_2)_jOR_3$, —$(CH_2)_qO(CH_2)_tOR_3$, —$(CH_2)_qO(CH_2)_tO(CH_2)_jOR_3$, —$(CH_2)_qO(CH_2)_tO(CH_2)_uO(CH_2)_jOR_3$, —$(CH_2)_jC(O)R_3$, —$(CH_2)_jC(O)OR_3$, —$(CH_2)_jOC(O)R_3$, —$(CH_2)_jNR_4R_5$, —$(CH_2)_jC(O)NR_4R_5$, —$(CH_2)_jOC(O)NR_4R_5$, —$(CH_2)_jNR_6C(O)R_3$, —$(CH_2)_jNR_6C(O)OR_3$, —$(CH_2)_jNR_6C(O)NR_4R_5$, —$(CH_2)_jS(O)_mR_7$, —$(CH_2)_jS(O)_2NR_4R_5$, —$(CH_2)_jNR_6S(O)_2R_7$, or —$(CH_2)_jOP(O)(OR_7)_2$, wherein q is independently an integer from 0 to 20, and j, t, and u are each independently an integer from 0 to 6, and each m is independently an integer from 0 to 2, wherein $R_2$ is optionally independently substituted with 1 to 5 $R_8$ groups;
$R_3$, $R_4$, $R_5$, $R_6$, and $R_7$ are each independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or
$R_3$, $R_6$, and $R_7$ are as described above, and $R_4$ and $R_5$, together with the N atom to which they are attached, form substituted or unsubstituted heterocycloalkyl, or substituted or unsubstituted heteroaryl, wherein $R_3$, $R_4$, $R_5$, $R_6$, and $R_7$ are each optionally independently substituted with 1 to 5 $R_8$ groups; and
$R_8$ is independently selected from the group consisting of halogen, hydroxyl, cyano, nitro, alkyl, perfluoroalkyl, oxo, $NH_2$, NH(alkyl), N(alkyl)$_2$, O-alkyl, S-alkyl, aryl, arylalkyl, heteroaryl, and heteroarylalkyl.

4. The method of claim 3, wherein
n is 2;
$R_1$ is independently selected from the group consisting of substituted or unsubstituted ($C_1$-$C_{20}$)alkyl, substituted or unsubstituted ($C_1$-$C_{20}$)heteroalkyl, substituted or unsubstituted ($C_3$-$C_7$)cycloalkyl substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl;
each $R_2$ is independently selected from the group consisting of hydrogen, halogen, nitro, cyano, hydroxyl, substituted or unsubstituted ($C_1$-$C_6$)alkyl, substituted or unsubstituted ($C_1$-$C_6$)heteroalkyl, perfluoroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, substituted or unsubstituted quinoxalinyl, $-(CH_2)_jCN$, $-(CH_2)_jOR_3$, $-(CH_2)_qO(CH_2)_jOR_3$, $-(CH_2)_qO(CH_2)_tO(CH_2)_jOR_3$, $-(CH_2)_qO(CH_2)_tO(CH_2)_uO(CH_2)_jOR_3$, $-(CH_2)_jC(O)R_3$, $-(CH_2)_jC(O)OR_3$, $-(CH_2)_jOC(O)R_3$, $-(CH_2)_jNR_4R_5$, $-(CH_2)_jC(O)NR_4R_5$, $-(CH_2)_jOC(O)NR_4R_5$, $-(CH_2)_jNR_6C(O)R_3$, $-(CH_2)_jNR_6C(O)OR_3$, $-(CH_2)_jNR_6C(O)NR_4R_5$, $-(CH_2)_jS(O)_mR_7$, $-(CH_2)_jS(O)_2NR_4R_5$, $-(CH_2)_jNR_6S(O)_2R_7$, or $-(CH_2)_jOP(O)(OR_7)_2$;

$R_3$, $R_4$, $R_5$, $R_6$, and $R_7$ are each independently selected from the group consisting of hydrogen, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, substituted or unsubstituted $(C_3-C_7)$heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl, or $R_3$, $R_6$, and $R_7$ are as described above, and $R_4$ and $R_5$, together with the N atom to which they are attached, form substituted or unsubstituted pyrrolidinyl, substituted or unsubstituted imidazolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl; and each $R_8$ is independently selected from the group consisting of halogen, hydroxyl, cyano, nitro, perfluoroalkyl, oxo, $NH_2$, $NH((C_1-C_6)alkyl)$, $N((C_1-C_6)alkyl)_2$, $O(C_1-C_6)alkyl$, $S(C_1-C_6)alkyl$, phenyl, biphenyl, naphthyl, benzyl, pyrrolyl, pyrazolyl, imidazolyl, furyl, thienyl, oxazolyl, isooxazolyl, thiazolyl, pyridinyl, pyridazinyl, pyridinyl, pyrazinyl, indolyl, indazolyl, benzimidazolyl, benzofuryl, benzothienyl, benzoxazolyl, benzoisooxazolyl, benzthiazolyl, quinolinyl, isoquinolinyl, phthalazinyl, quinazolinyl, and quinoxalinyl.

5. The method of claim 4, wherein
$R_1$ is substituted or unsubstituted $(C_1-C_{20})$alkyl; and
$R_2$ is selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, and substituted or unsubstituted $(C_3-C_7)$heterocycloalkyl.

6. The method of claim 4, wherein:
$R_1$ is substituted or unsubstituted $(C_1-C_{20})$alkyl; and
each $R_2$ is independently selected from the group consisting of substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl.

7. The method of claim 4, wherein:
$R_1$ is substituted or unsubstituted $(C_1-C_{20})$alkyl; and
each $R_2$ is independently selected from the group consisting of $-(CH_2)_jCN$, $-(CH_2)_jOR_3$, $-(CH_2)_qO(CH_2)_jOR_3$, $-(CH_2)_qO(C_2)_tO(CH_2)_jOR_3$, $-(CH_2)_qO(CH_2)_tO(CH_2)_uO(CH_2)_jOR_3$, $-(CH_2)_jC(O)R_3$, $-(CH_2)_jC(O)OR_3$, $-(CH_2)_jOC(O)R_3$, $-(CH_2)_jNR_4R_5$, $-(CH_2)_jC(O)NR_4R_5$, $-(CH_2)_jOC(O)NR_4R_5$, $-(CH_2)_jNR_6C(O)R_3$, $-(CH_2)_jNR_6C(O)OR_3$, $-(CH_2)_jNR_6C(O)NR_4R_5$, $-(CH_2)_jS(O)_mR_7$, $-(CH_2)_jS(O)_2NR_4R_5$, $-(CH_2)_jNR_6S(O)_2R_7$, or $-(CH_2)_jOP(O)(OR_7)_2$.

8. The method of claim 7, wherein:
each $R_2$ is independently selected from the group consisting of $-(CH_2)_jOR$, $-(CH_2)_qO(CH_2)_jOR_3$, $-(CH_2)_qO(CH_2)_tO(CH_2)_jOR_3$, and $-(CH_2)_qO(CH_2)_tO(CH_2)_uO(CH_2)_jOR_3$.

9. The method of claim 8, wherein $R_3$ is hydrogen.

10. The method of claim 4, wherein:
$R_1$ is substituted or unsubstituted phenyl; and
each $R_2$ is independently selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloakyl, and substituted or unsubstituted $(C_3-C_7)$heterocycloalkyl.

11. The method of claim 4, wherein:

$R_1$ is substituted or unsubstituted phenyl; and each $R_2$ is independently selected from the group consisting of substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl.

12. The method of claim 4, wherein:

$R_1$ is substituted or unsubstituted phenyl; and each $R_2$ is independently selected from the group consisting of $-(CH_2)_j CN$, $-(CH_2)_j OR_3$, $-(CH_2)_q O(CH_2)_j OR_3$, $-(CH_2)_q O(CH_2)_t O(CH_2)_j OR_3$, $-(CH_2)_q O(CH_2)_t O(CH_2)_u O(CH_2)_j OR^3$, $-(CH_2)_j C(O)R^3$, $-(CH_2)_j C(O)OR_3$, $-(CH_2)_j OC(O)R_3$, $-(CH_2)_j NR_4 R_5$, $-(CH_2)_j C(O)NR_4 R_5$, $-(CH_2)_j OC(O)NR_4 R_5$, $-(CH_2)_j NR_6 C(O)R_3$, $-(CH_2)_j NR_6 C(O)OR_3$, $-(CH_2)_j NR_6 C(O)NR_4 R_5$, $-(CH_2)_j S(O)_m R_7$, $-(CH_2)_j S(O)_2 NR_4 R_5$, $-(CH_2)_j NR_6 S(O)_2 R_7$, or $-(CH_2)_j OP(O)(OR_7)_2$.

13. The method of claim 3, wherein each $R_2$ is independently selected from the group consisting of $-(CH_2)_j OR_3$, $-(CH_2)_q O(CH_2)_j OR_3$, $-(CH_2)_q O(CH_2)_t O(CH_2)_j OR_3$, and $-(CH_2)_q O(CH_2)_t O(CH_2)_u O(CH_2)_j OR_3$.

14. The method of claim 13, wherein $R_3$ is hydrogen; $R_4$ and $R_5$ are $(C_1-C_6)$alkyl; and $R_7$ is $(C_1-C_6)$alkyl or phenyl.

15. The method of claim 12, wherein each $R_2$ is independently selected from the group consisting of $-(CH_2)_j OR_3$; $R_3$ is arylalkyl; and $R_8$ is halogen.

16. The method of claim 3, wherein the compound has the following chemical structure:

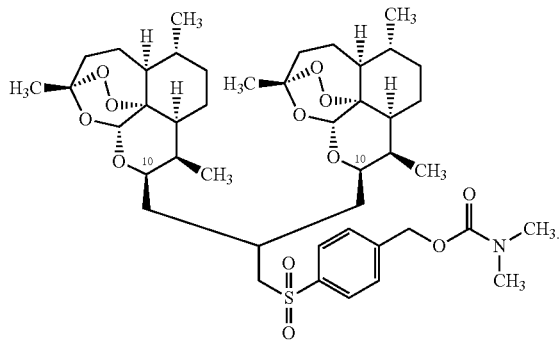

17. The method of claim 1, wherein the compound is a compound of Formula (IV), wherein $A_1$ and $A_2$ are each independently selected from the group consisting of hydrogen, substituted or unsubstituted cyclohexyl, substituted or unsubstituted phenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl or $A_1$ and $A_2$ together form a substituted or unsubstituted biphenyl moiety.

18. The method of claim 17, wherein $A_1$ and $A_2$ are each independently substituted or unsubstituted phenyl or $A_1$ and $A_2$ together form a substituted or unsubstituted biphenyl moiety and the compound of Formula (IV) has the following chemical structure:

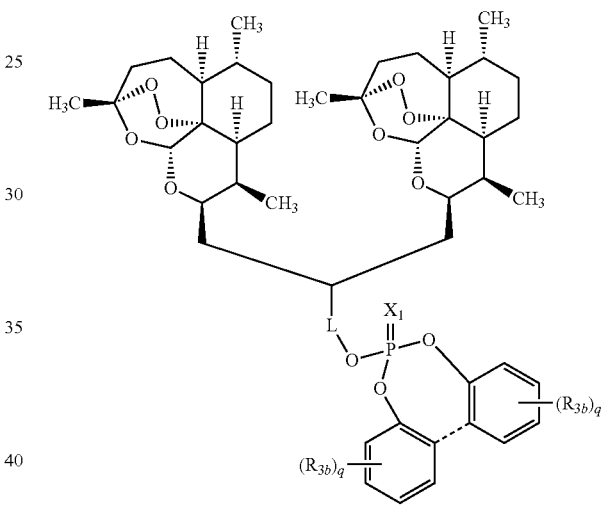

wherein:

each q is independently an integer from 0 to 5, provided that at least one occurrence of q is not 0;

the dashed line is a bond that can be present or absent; and each occurrence of $R_{3b}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

19. The method of claim 18, wherein $R_{3b}$ is halogen or alkyl.

20. The method of claim 18, wherein $A_1$ and $A_2$ together form a biphenyl moiety.

21. The method of claim 17, wherein the compound of Formula (IV) is selected from the group consisting of:

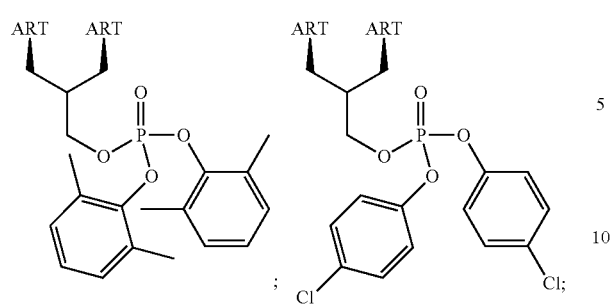
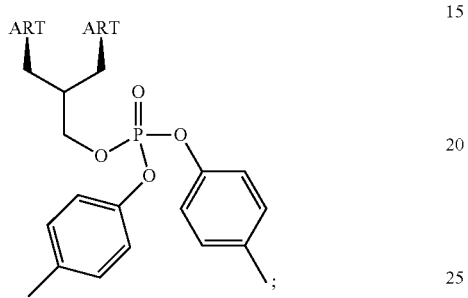
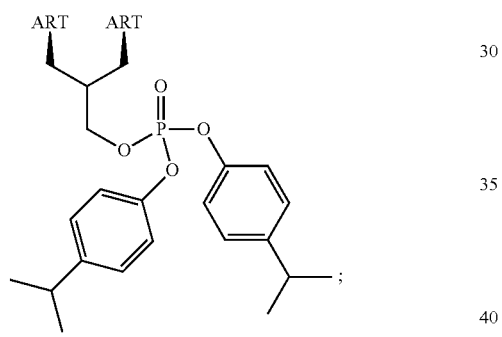
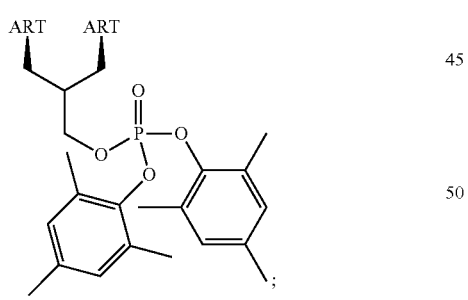
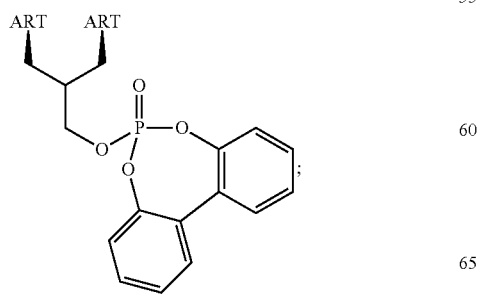
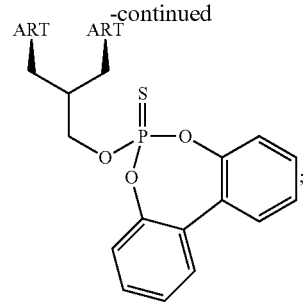
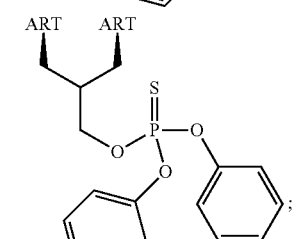
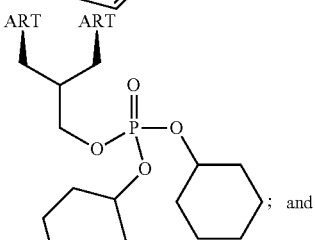
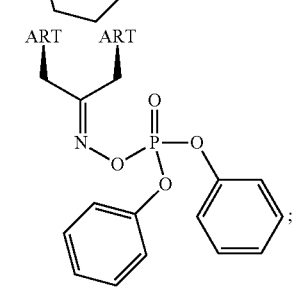
wherein the term ART represents the following formula:
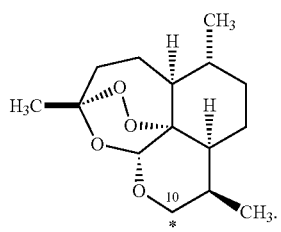
22. The method of claim 1, wherein the compound is a compound of Formula (V), and the compound of Formula (V) is selected from the group consisting of:
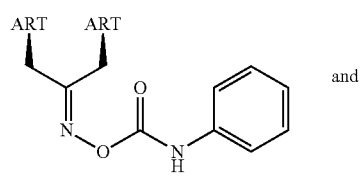
and

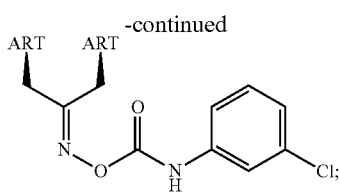

wherein the term ART represents the following formula:

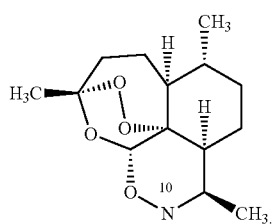

23. A method for inhibiting cytomegalovirus (CMV) replication in a cell, the method comprising contacting the cell with a compound selected from the group consisting of:

(a)

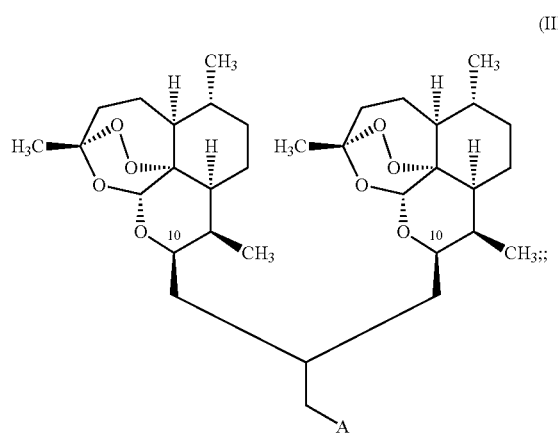

(III)

wherein:
A is —OH or $S(O)_n$—$R_1$;
n is independently an integer from 0 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein $R_1$ is optionally substituted with 1 to 5 $R_2$ groups;
each $R_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —$(CH_2)_j$CN, —$(CH_2)_j$OR$_3$, —$(CH_2)_q$O$(CH_2)_j$OR$_3$, —$(CH_2)_q$O$(CH_2)_j$O$(CH_2)_j$OR$_3$, —$(CH_2)_q$O$(CH_2)_t$O$(CH_2)_u$O$(CH_2)_j$OR$_3$, —$(CH_2)_j$C(O)R$_3$, —$(CH_2)_j$C(O)OR$_3$, —$(CH_2)_j$OC(O)R$_3$, —$(CH_2)_j$NR$_4$R$_5$, —$(CH_2)_j$C(O)NR$_4$R$_5$, —$(CH_2)_j$OC(O)NR$_4$R$_5$, —$(CH_2)_j$NR$_6$C(O)R$_3$, —$(CH_2)_j$NR$_6$C(O)OR$_3$, —$(CH_2)_j$NR$_6$C(O)NR$_4$R$_5$, —$(CH_2)_j$S(O)$_m$R$_7$, —$(CH_2)_j$S(O)$_2$NR$_4$R$_5$, —$(CH_2)_j$NR$_6$S(O)$_2$R$_7$, or —$(CH_2)_j$OP(O)(OR$_7$)$_2$, wherein q is independently an integer from 0 to 20, and j, t, and u are each independently an integer from 0 to 6, and each m is independently an integer from 0 to 2, wherein $R_2$ is optionally independently substituted with 1 to 5 $R_8$ groups;

$R_3$, $R_4$, $R_6$, and $R_7$ are each independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or $R_3$, $R_6$, and $R_7$ are as described above, and $R_4$ and $R_5$, together with the N atom to which they are attached, form substituted or unsubstituted heterocycloalkyl, or substituted or unsubstituted heteroaryl, wherein $R_3$, $R_4$, $R_5$, $R_6$, and $R_7$ are each optionally independently substituted with 1 to 5 $R_8$ groups; and $R_8$ is independently selected from the group consisting of halogen, hydroxyl, cyano, nitro, alkyl, perfluoroalkyl, oxo, $NH_2$, NH(alkyl), N(alkyl)$_2$, O-alkyl, S-alkyl, aryl, arylalkyl, heteroaryl, and heteroarylalkyl;

(b)

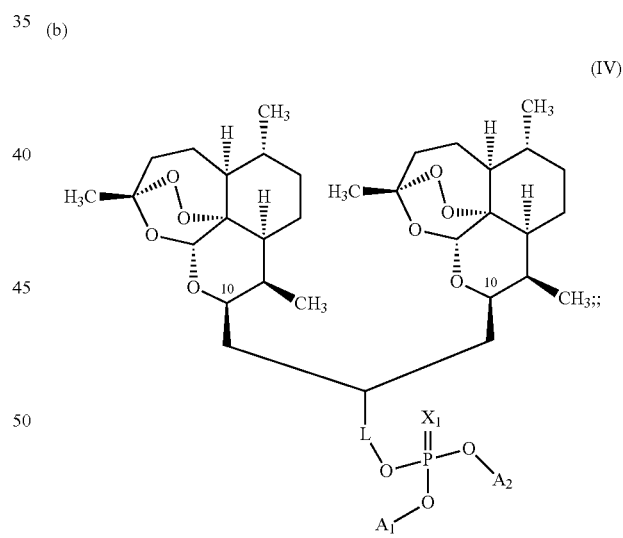

(IV)

wherein:
L is a linking group selected from (=N)— or —$(CH_2)_m$—, wherein m is an integer from 0 to 3;
$X_1$ is O or S;
$A_1$ and $A_2$ can be the same or different and are each independently selected from the group consisting of hydrogen, substituted or unsubstituted cycloalkyl, substituted or unsubstituted aryl, and substituted or unsubstituted heteroaryl, or $A_1$ and $A_2$ together form a substituted or unsubstituted biphenyl moiety; and (c)

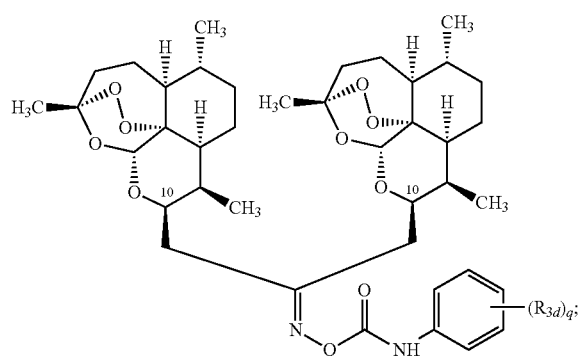

(V)

wherein:
q is an integer from 0 to 5;
each occurrence of $R_{3d}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl; or
an enantiomer, diastereomer, racemate or pharmaceutically acceptable salt, prodrug, or solvate thereof.

24. The method of claim 23, wherein the compound of Formula (III) has the following structure:

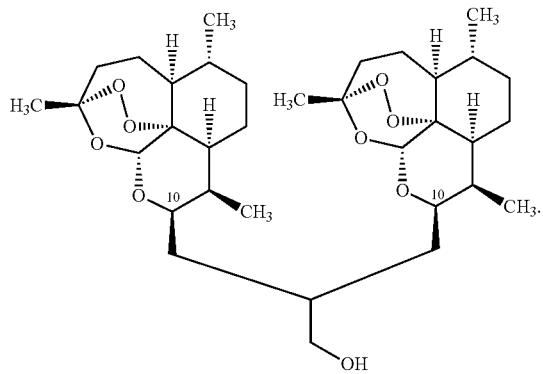

25. The method of claim 23, wherein the compound of Formula (III) has the following structure:

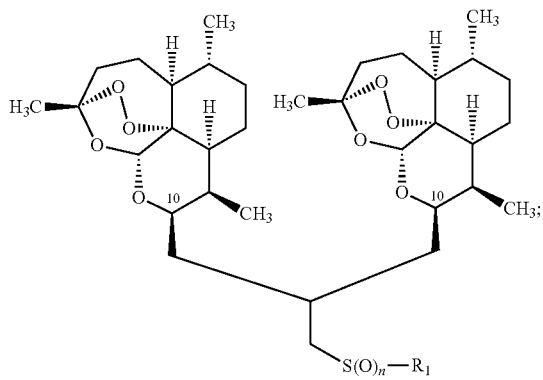

wherein:
n is independently an integer from 0 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein $R_1$ is optionally substituted with 1 to 5 $R_2$ groups;
each $R_2$ is independently selected from the group consisting of hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$OR$_3$, —(CH$_2$)$_q$O(CH$_2$)$_t$O(CH$_2$)$_u$O(CH$_2$)$_j$OR$_3$, —(CH$_2$)$_j$C(O)R$_3$, —(CH$_2$)$_j$C(O)OR$_3$, —(CH$_2$)$_j$OC(O)R$_3$, —(CH$_2$)$_j$NR$_4$R$_5$, —(CH$_2$)$_j$C(O)NR$_4$R$_5$, —(CH$_2$)$_j$OC(O)NR$_4$R$_5$, —(CH$_2$)$_j$NR$_6$C(O)R$_3$, —(CH$_2$)$_j$NR$_6$C(O)OR$_3$, —(CH$_2$)$_j$NR$_6$C(O)NR$_4$R$_5$, —(CH$_2$)$_j$S(O)$_m$R$_7$, —(CH$_2$)$_j$S(O)$_2$NR$_4$R$_5$, —(CH$_2$)$_j$NR$_6$S(O)$_2$R$_7$, or —(CH$_2$)$_j$OP(O)(OR$_7$)$_2$, wherein q is independently an integer from 0 to 20, and j, t, and u are each independently an integer from 0 to 6, and each m is independently an integer from 0 to 2, wherein $R_2$ is optionally independently substituted with 1 to 5 $R_8$ groups;
$R_3$, $R_4$, $R_5$, $R_6$, and $R_7$ are each independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, or
$R_3$, $R_6$, and $R_7$ are as described above, and $R^4$ and $R_5$, together with the N atom to which they are attached, form substituted or unsubstituted heterocycloalkyl, or substituted or unsubstituted heteroaryl, wherein $R_3$, $R_4$, $R_5$, $R_6$, and $R_7$ are each optionally independently substituted with 1 to 5 $R_8$ groups; and
$R_8$ is independently selected from the group consisting of halogen, hydroxyl, cyano, nitro, alkyl, perfluoroalkyl, oxo, NH$_2$, NH(alkyl), N(alkyl)$_2$, O-alkyl, S-alkyl, aryl, arylalkyl, heteroaryl, and heteroarylalkyl.

26. The method of claim 25, wherein
n is 2;
$R_1$ is independently selected from the group consisting of substituted or unsubstituted (C$_1$-C$_{20}$)alkyl, substituted or unsubstituted (C$_1$-C$_{20}$)heteroalkyl, substituted or unsubstituted (C$_3$-C$_7$)cycloalkyl, substituted or unsubstituted C$_3$-C$_7$)heterocycoaky, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl;

each $R_2$ is independently selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, substituted or unsubstituted $(C_3-C_7)$heterocycloalkyl, substituted or unsubstituted phenyl, substituted or unsubstituted biphenyl, substituted or unsubstituted naphthyl, substituted or unsubstituted benzyl, substituted or unsubstituted pyrroyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, substituted or unsubstituted quinoxalinyl, $-(CH_2)_j CN$, $-(CH_2)_j OR_3$, $-(CH_2)_q(CH_2)_j OR_3$, $-(CH_2)_q O(CH_2)_t O(CH_2)_j OR_3$, $-(CH_2)_q O(CH_2)_t O(CH_2)_u O(CH_2)_j OR_3$, $-(CH_2)_j C(O)R_3$, $-(CH_2)_j C(O)OR_3$, $-(CH_2)_j OC(O)R_3$, $-(CH_2)_j NR_4 R_5$, $-(CH_2)_j C(O)N R_4 R_5$, $-(CH_2)_j OC(O)NR_4 R_5$, $-(CH_2)_j NR_6 C(O)R_3$, $-(CH_2)_j NR_6 C(O)OR_3$, $-(CH_2)_j NR_6 C(O)NR_4 R_5$, $-(CH_2)_j S(O)_m R_7$, $-(CH_2)_j S(O)_2 NR_4 R_5$, $-(CH_2)_j NR_6 S(O)_2 R_7$, or $-(CH_2)_j OP(O)(OR_7)_2$;

$R_3$, $R_4$, $R_5$, $R_6$, and $R_7$ are each independently selected from the group consisting of hydrogen, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, substituted or unsubstituted $(C_3-C_7)$heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazoly, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl, or $R_3$, $R_6$, and $R_7$ are as described above, and $R_4$ and $R_5$, together with the N atom to which they are attached, form substituted or unsubstituted pyrrolidinyl, substituted or unsubstituted imidazolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl; and each $R_8$ is independently selected from the group consisting of halogen, hydroxyl, cyano, nitro, perfluoroalkyl, oxo, $NH_2$, $NH((C_1-C_6)alkyl)$, $N((C_1-C_6)alkyl)_2$, $O(C_1-C_6)alkyl$, $S(C_1-C_6)alkyl$, phenyl, biphenyl, naphthyl, benzyl, pyrrolyl, pyrazolyl, imidazolyl, furyl, thienyl, oxazolyl, isooxazolyl, thiazolyl, pyridinyl, pyridazinyl, pyrimidinyl, pyrazinyl, indolyl, indazolyl, benzimidazolyl, benzofuryl, benzothienyl, benzoxazolyl, benzoisooxazolyl, benzthiazolyl, quinolinyl, isoquinolinyl, phthalazinyl, quinazolinyl, and quinoxalinyl.

27. The method of claim 26, wherein
$R_1$ is substituted or unsubstituted $(C_1-C_{20})$alkyl; and
$R_2$ is selected from the group consisting of hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, and substituted or unsubstituted $(C_3-C_7)$heterocycloalkyl.

28. The method of claim 26, wherein:
$R_1$ is substituted or unsubstituted $(C_1-C_{20})$alkyl; and
each $R_2$ is independently selected from the group consisting of substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl.

29. The method of claim 26, wherein:
$R_1$ is substituted or unsubstituted $(C_1-C_{20})$alkyl; and
each $R_2$ is independently selected from the group consisting of —(CH$_2$)$_j$CN, —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$OR$_3$, —(CH$_2$)$_q$O(CH$_2$)$_t$(CH$_2$)$_u$O(CH$_2$)$_j$OR$_3$, —(CH$_2$)$_j$C(O)R$_3$, —(CH$_2$)$_j$C(O)OR$_3$, —(CH$_2$)$_j$OC(O)R$_3$, —(CH$_2$)$_j$NR$_4$R$_5$, —(CH$_2$)$_j$C(O)NR$_4$R$_5$, —(CH$_2$)$_j$OC(O)NR$_4$R$_5$, —(CH$_2$)$_j$NR$_6$C(O)R$_3$, —(CH$_2$)$_j$NR$_6$C(O)OR$_3$, —(CH$_2$)$_j$NR$_6$C(O)NR$_4$R$_5$, —(CH$_2$)$_j$S(O)$_m$R$^7$, —(CH$_2$)$_j$S(O)$_2$NR$_4$R$_5$, —(CH$_2$)$_j$NR$_6$S(O)$_2$R$_7$, or —(CH$_2$)$_j$OP(O)(OR$_7$)$_2$.

30. The method of claim 29, wherein:
each R$_2$ is independently selected from the group consisting of —(CH$_2$)$_j$OR, —(CH$_2$)$_q$O(CH$_2$)$_j$OR$_3$, —(CH$_2$)$_q$O(CH$_2$)$_t$O(CH$_2$)$_j$OR$_3$, and —(CH$_2$)$_q$O(CH$_2$)$_t$O(CH$_2$)$_u$O(CH$_2$)$_j$OR$_3$.

31. The method of claim 30, wherein R$_3$ is hydrogen.

32. The method of claim 26, wherein:
R$_1$ is substituted or unsubstituted phenyl; and
each R$_2$ is independently selected from the group consisting of hydrogen, halogen, nitro, cyano, hydroxyl, substituted or unsubstituted (C$_1$-C$_6$)alkyl, substituted or unsubstituted (C$_1$-C$_6$)heteroalkyl, perfluoroalkyl, substituted or unsubstituted (C$_3$-C$_7$)cycloalkyl, and substituted or unsubstituted (C$_3$-C$_7$)heterocycloalkyl.

33. The method of claim 26, wherein:
R$_1$ is substituted or unsubstituted phenyl; and
each R$_2$ is independently selected from the group consisting of substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, and substituted or unsubstituted quinoxalinyl.

34. The method of claim 26, wherein:
R$_1$ is substituted or unsubstituted phenyl; and
each R$_2$ is independently selected from the group consisting
of —(CH$_2$)$_j$CN, —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$O(CH$_2$)$_j$OR$_3$, —(CH$_2$)$_q$O(CH$_2$)$_t$O(CH$_2$)$_u$O(CH$_2$)$_j$OR$^3$, —(CH$_2$)$_j$C(O)R$^3$, —(CH$_2$)$_j$C(O)OR$_3$, —(CH$_2$)$_j$OC(O)R$_3$, —(CH$_2$)$_j$NR$_4$R$_5$, —(CH$_2$)$_j$C(O)NR$_4$R$_5$, —(CH$_2$)$_j$OC(O)NR$_4$R$_5$, —(CH$_2$)$_j$NR$_6$C(O)R$_3$, —(CH$_2$)$_j$NR$_6$C(O)OR$_3$, —(CH$_2$)$_j$NR$_6$C(O)NR$_4$R$_5$, —(CH$_2$)$_j$S(O)$_m$R$_7$, —(CH$_2$)$_j$S(O)$_2$NR$_4$R$_5$, —(CH$_2$)$_j$NR$_6$S(O)$_2$R$_7$, or —(CH$_2$)$_j$OP(O)(OR$_7$)$_2$.

35. The method of claim 25, wherein each R$_2$ is independently selected from the group consisting of —(CH$_2$)$_j$OR$_3$, —(CH$_2$)$_q$O(CH$_2$)$_j$OR$_3$, —(CH$_2$)$_q$O(CH$_2$)$_t$O(CH$_2$)$_j$OR$_3$, and —(CH$_2$)$_q$O(CH$_2$)$_t$O(CH$_2$)$_u$O(CH$_2$)$_j$OR$_3$.

36. The method of claim 35, wherein R$_3$ is hydrogen; R$_4$ and R$_5$ are (C$_1$-C$_6$)alkyl; and R$_7$ is (C$_1$-C$_6$)alkyl or phenyl.

37. The method of claim 34, wherein each R$_2$ is independently selected from the group consisting of —(CH$_2$)$_j$OR$_3$; R$_3$ is arylalkyl; and R$_8$ is halogen.

38. The method of claim 25, wherein the compound has the following chemical structure:

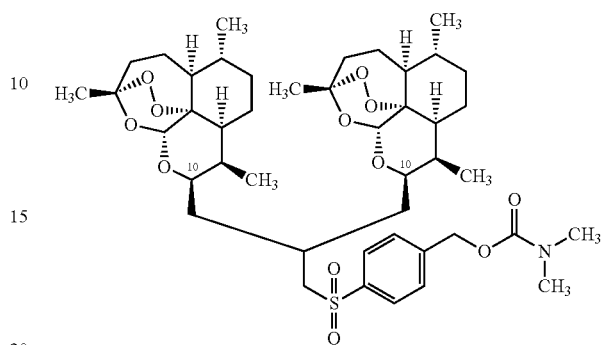

39. The method of claim 23, wherein the compound is a compound of Formula (IV), and wherein A$_1$ and A$_2$ are each independently selected from the group consisting of hydrogen, substituted or unsubstituted cyclohexyl, substituted or unsubstituted phenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl or A$_1$ and A$_2$ together form a substituted or unsubstituted biphenyl moiety.

40. The method of claim 39, wherein A$_1$ and A$_2$ are each independently substituted or unsubstituted phenyl or A$_1$ and A$_2$ together form a substituted or unsubstituted biphenyl moiety and the compound of Formula (IV) has the following chemical structure:

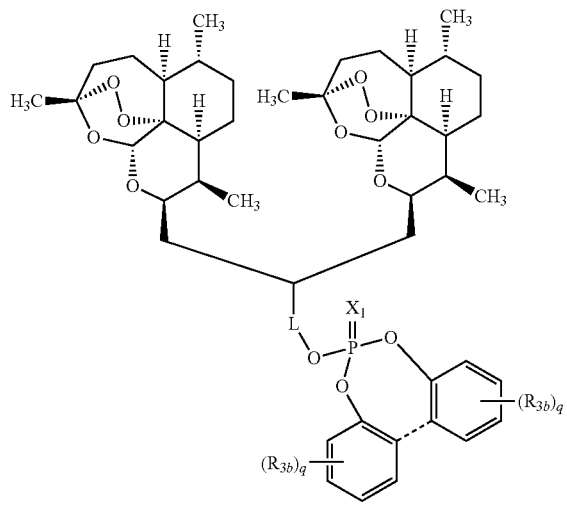

wherein:
each q is independently an integer from 0 to 5, provided that at least one occurrence of q is not 0;
the dashed line is a bond that can be present or absent; and each occurrence of $R_{3b}$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

41. The method of claim 40, wherein $R_{3b}$ is halogen or alkyl.

42. The method of claim 40, wherein $A_1$ and $A_2$ together form a biphenyl moiety.

43. The method of claim 39, wherein the compound of Formula (IV) is selected from the group consisting of:

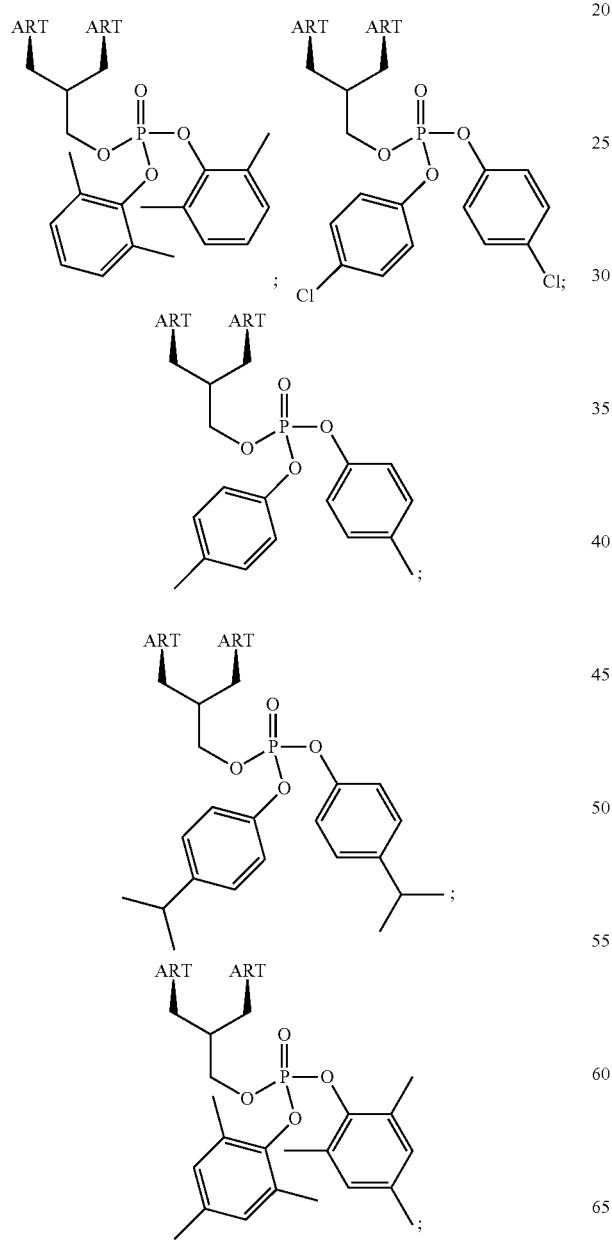

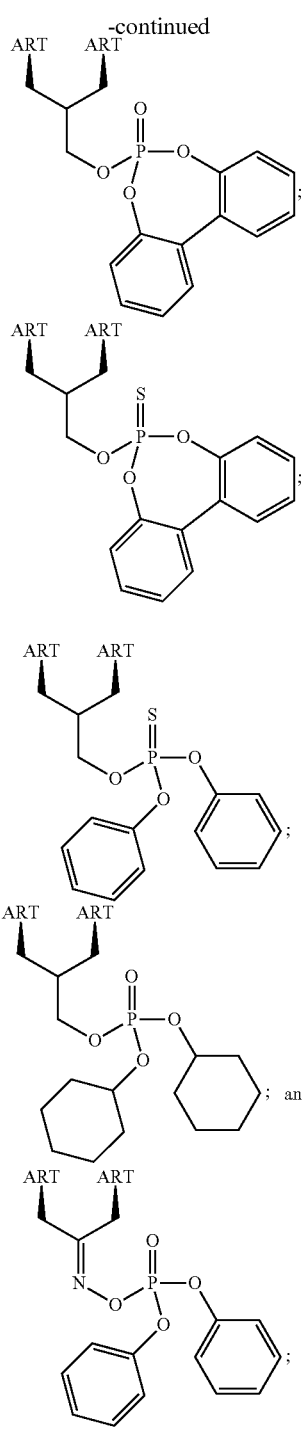

wherein the term ART represents the following formula:

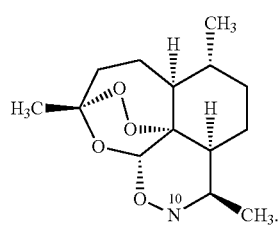

44. The method of claim 23, wherein the compound is a compound of Formula (V), and the compound of Formula (V) is selected from the group consisting of:

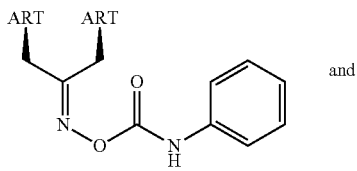

and

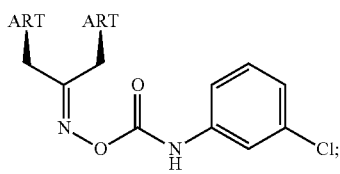

wherein the term ART represents the following formula:

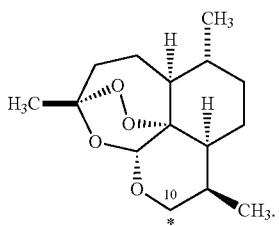

45. The method of claim 1, wherein the method further comprises the administration of at least one additional therapeutic agent.

46. The method of claim 45, wherein the at least one additional therapeutic agent is selected from the group consisting of ganciclovir, cidofovir and foscarnet.

47. The method of claim 23, wherein the method further comprises the administration of at least one additional therapeutic agent.

48. The method of claim 47, wherein the at least one additional therapeutic agent is selected from the group consisting of ganciclovir, cidofovir and foscarnet.

* * * * *